US012569437B2

(12) United States Patent (10) Patent No.: US 12,569,437 B2

Sawa et al. (45) Date of Patent: Mar. 10, 2026

(54) DISEASE-SITE-SPECIFIC LIPOSOMAL FORMULATION

(71) Applicants:Osaka University, Osaka (JP); Cuorips Inc, Tokyo (JP)

(72) Inventors: Yoshiki Sawa, Osaka (JP); Shigeru Miyagawa, Osaka (JP); Yoshiki Sakai, Osaka (JP); Yasuhiro Yanagi, Hyogo (JP)

(73) Assignees: Osaka University, Osaka (JP); Cuorips Inc., Tokyo (JP)

( * ) Notice: Subject to any disclaimer, the term of this patent is extended or adjusted under 35 U.S.C. 154(b) by 12 days.

(21) Appl. No.: 18/491,953

(22) Filed: Oct. 23, 2023

(65) Prior Publication Data

US 2024/0082154 A1 Mar. 14, 2024

Related U.S. Application Data

(63) Continuation of application No. 16/766,992, filed as application No. PCT/JP2017/042350 on Nov. 27, 2017, now abandoned.

(51) Int. Cl.
*A61K 9/127* (2025.01)
*A61K 9/1277* (2025.01)
*A61K 31/4406* (2006.01)

(52) U.S. Cl.
CPC ............ *A61K 9/127* (2013.01); *A61K 9/1277* (2013.01); *A61K 31/4406* (2013.01)

(58) Field of Classification Search
CPC .................................................. A61K 9/127
See application file for complete search history.

(56) References Cited

U.S. PATENT DOCUMENTS

| | | | |
|---|---|---|---|
| 5,480,998 | A | 1/1996 | Hamanaka et al. |
| 2006/0069018 | A1 | 3/2006 | Nishiura et al. |
| 2010/0323026 | A1 | 12/2010 | Sakai et al. |
| 2011/0262548 | A1 | 10/2011 | Mizushima et al. |
| 2014/0050690 | A1 | 2/2014 | Ishihara et al. |
| 2015/0157610 | A1 | 6/2015 | Asai et al. |
| 2015/0272874 | A1 | 10/2015 | Miyagawa et al. |
| 2016/0250395 | A1 | 9/2016 | Fukushima et al. |
| 2017/0202780 | A1 | 7/2017 | Egashira |

FOREIGN PATENT DOCUMENTS

| | | | | |
|---|---|---|---|---|
| EP | 2465537 A1 | * | 6/2012 | ............ A61K 31/19 |
| JP | H0687811 A | | 3/1994 | |
| JP | 2012/171883 A | | 9/2012 | |

(Continued)

OTHER PUBLICATIONS

Nagaya, Noritoshi. PGI2 derivates. Clinic All-Round. Nov. 2009. vol. 58, No. 11. pp. 2301-2306.

(Continued)

*Primary Examiner* — Benjamin J Packard

(74) *Attorney, Agent, or Firm* — Cesari and McKenna, LLP

(57) ABSTRACT

The present invention provides clinically applicable, safe and convenient, pharmaceutical compositions and methods for disease site-specific treatment. The pharmaceutical composition for disease site-specific treatment methods comprises a stealth liposome having a prostaglandin I2 receptor agonist encapsulated therein.

14 Claims, 17 Drawing Sheets

Blank liposome (Formulation)

Mixing ratio of 1/10 (Formulation 2)

Mixing ratio of 1/2 (Formulation 3)

Mixing ratio of 1/4 (Formulation 4)

(56)                    References Cited

FOREIGN PATENT DOCUMENTS

| | | | |
|---|---|---|---|
| JP | 2016/501233 | A | 1/2016 |
| JP | 2016/512550 | A | 4/2016 |
| WO | WO-2004/032965 | A1 | 4/2004 |
| WO | WO-2008/047863 | A1 | 4/2008 |
| WO | WO-2010/058669 | A1 | 5/2010 |
| WO | WO-2013/176223 | A1 | 11/2013 |
| WO | WO-2014/069401 | A1 | 5/2014 |
| WO | WO-2014/085813 | A1 | 6/2014 |
| WO | WO-2014/159760 | A1 | 10/2014 |
| WO | WO-2015/056504 | A1 | 4/2015 |
| WO | WO-2016/006577 | A1 | 1/2016 |

OTHER PUBLICATIONS

Notice of Termination of Reconsideration. Japanese Patent Office. Oct. 5, 2021. For the related JP patent application No. 2016-211126.

Nina et al. (Pancreatology 14 (2014) 201-2010) (Year: 2014).

Dos Santos et al "Improved Retention of Idarubicin After Intravenous Injection Obtained for Cholesterol-Free Liposomes" Biochimica et aBiophysica Acta vol. 1561, pp. 188-201, 2002.

Horisawa et al "Size-Dependency of DL-Lactide/Glycolide Copolymer Particulates for Intra-Articular Delivery System on Phagocytosis in Rat Synovium" Pharmaceutical Research vol. 19, pp. 132-139, 2002.

Ishihara et al "Prostaglandin $E_1$-Containing Nanoparticles Improve Walking Activity in an Experimental Rat Model of Intermittent Claudication" Journal of Pharmacy and Pharmacology vol. 65, pp. 1187-1194, 2013.

Jain et al "Liposomal Nanoparticles Encapsulating Iloprost Exhibit Enhanced Vasodilation in Pulmonary Arteries" International Journal of Nanomedicine vol. 9, pp. 3249-3261, 2014.

Kasaoka et al "Stealth Liposome for Delivery System" Membrane vol. 28, pp. 135-144, 2003.

Kawashima et al "Mucoadhesive DL-Lactide/Glycolide Copolymer Nanospheres Coated with Chitosan to Improve Oral Delivery of Elcatonin" Pharmaceutical Development and Technology vol. 5, pp. 77-85, 2000.

Miyagawa "Development and Practice of the In Situ Induced Regeneration Therapy Using New Oxime Derivatives Sustained-Release Formulation (YS-1402), Aiming for Life Prognosis Improvement and Artificial Heart Device Removal in Cardiomyopathy Patients with Severe Heart Failure Dilated" Rinsho Hyoka (Clinical Evaluation) vol. 43, pp. 464-471, 2016.

Mizushima "Development of a Therapeutic Agent for Pulmonary Hypertension Using a Stealth-Type Nanoparticle" The $31^{st}$ Annual Meeting of the Japan Society of Drug Delivery System, p. 168, 2015.

Notice of Reasons for Refusal Issued in Corresponding Japanese Patent Application No. 2016-211,126 on Aug. 31, 2020.

Paolino et al "Interaction Between PEG Lipid and DSPE/DSPC Phospholipids: An Insight of PEGylation Degree and Kinetics of de-PEGylation" Colloids and Surfaces B: Biointerfaces vol. 155, pp. 266-275, 2017.

2-[[5-[2-[(E)-[phenyl(pyridine-3-yl) methylidene]amino]oxyethyl]-7, 8-dihydronaphthalen-1-yl]oxy]acetic acid, National Library of Medicine, National Center for Biotechnology Information, 12 pages, May 4, 2006.

Office Action for European Patent Application No. 17 932 885.1, European Patent Office, Jan. 19, 2024, 6 pages, Rijswijk, Netherlands.

* cited by examiner

Fig. 11
(A)    Magnification:   x 10000
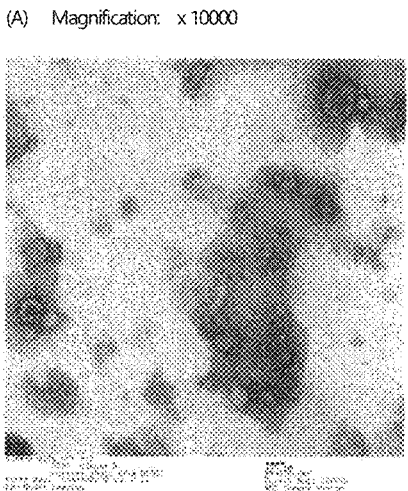
(B)    Magnification:   x 25000
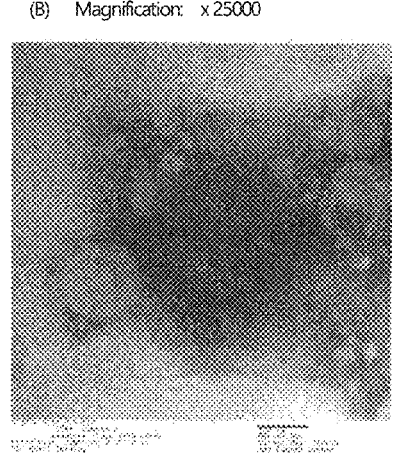

Fig. 12

Sample 1: Oxide-producing sample

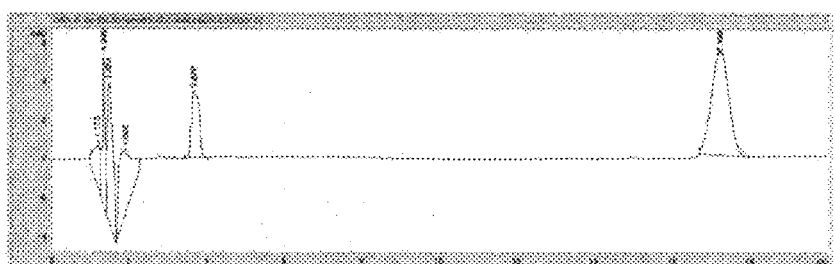

* : An oxide of compound (A) was confirmed at a retention time of around 4 minutes (Journal of Microcapsulation, 2012, 1-12)

Sample 2: Control sample

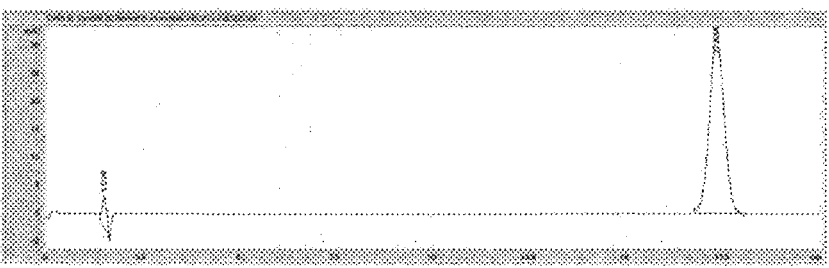

Sample 3: Compound (A) control sample

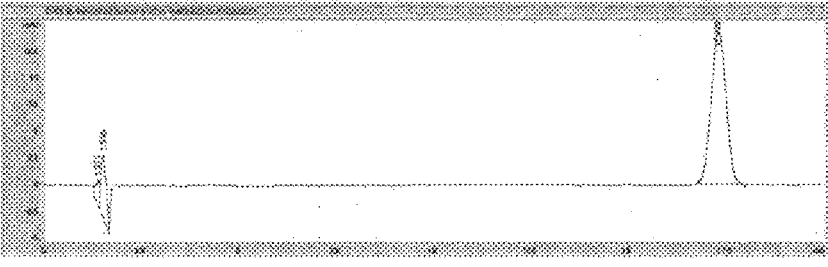

* : No production of an oxide of compound (A) was confirmed in an environment of 37°C.

Sample 4: Lipid control sample

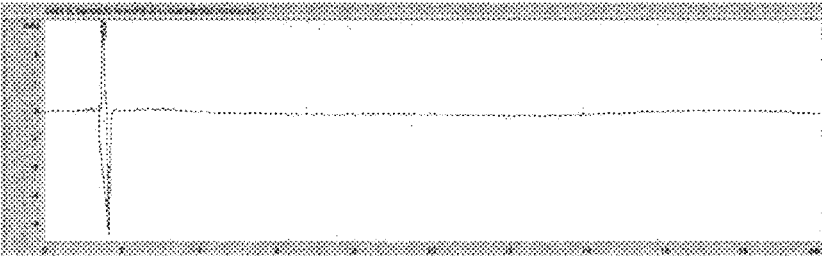

* : No influence of lipid on assay was confirmed.

Sample 5: Liposome sample

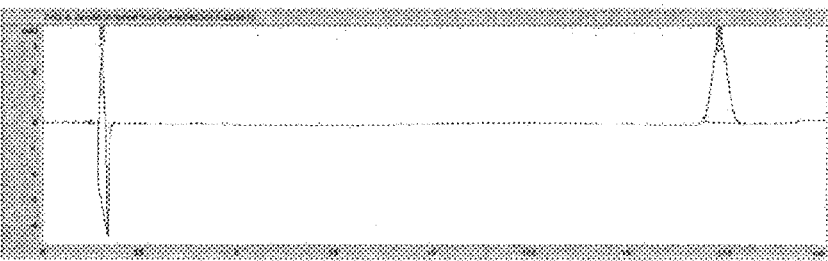

* : No production of an oxide of compound (A) was confirmed, even under liposomal conditions.

(A)  Magnification:  x 10000

(B)  Magnification:  x 25000

(A)   Magnification:   x 10000          (B)   Magnification:   x 25000

Fig. 19
Before ultrafiltration (Formulation 24)
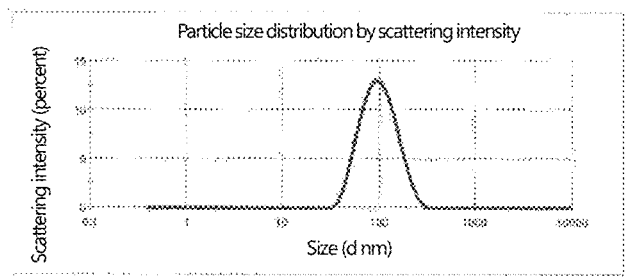
After ultrafiltration (Formulation 25)
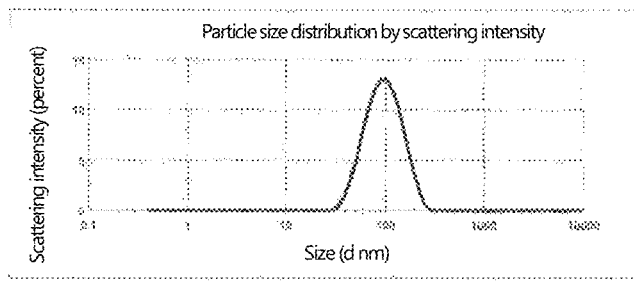

Fig. 20
Before ultrafiltration
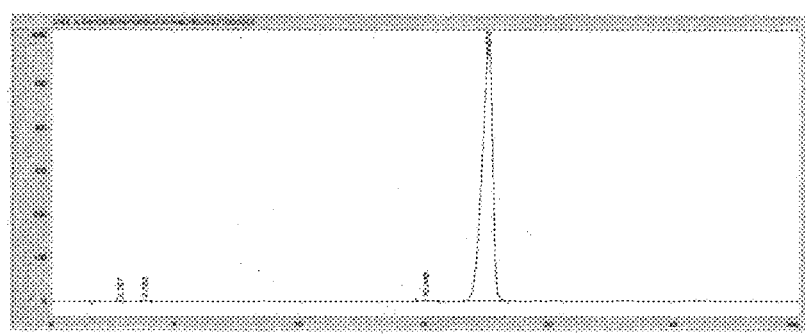
| No. | Time | Area | Height | Width | Symmetry | Area % |
|---|---|---|---|---|---|---|
| 1 | 3.756 | 13.2 | 1.8 | 0.1137 | 0.823 | 0.072 |
| 2 | 15.067 | 71 | 3 | 0.3472 | 0.933 | 0.389 |
| 3 | 17.683 | 18178 | 615.6 | 0.4565 | 1.893 | 99.599 |
After ultrafiltration
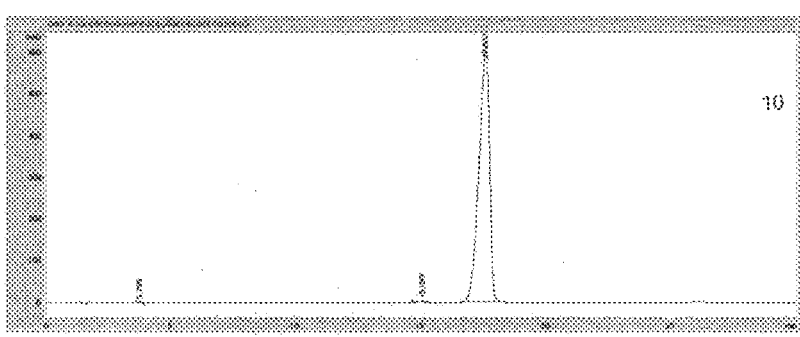
| No. | Time | Area | Height | Width | Symmetry | Area % |
|---|---|---|---|---|---|---|
| 1 | 2.797 | 9.7 | 1.8 | 0.0951 | 0.896 | 0.055 |
| 2 | 3.783 | 33 | 3.3 | 0.1692 | 0.923 | 0.186 |
| 3 | 15.046 | 67.6 | 2.8 | 0.3694 | 0.876 | 0.380 |
| 4 | 17.57 | 17692.8 | 593.1 | 0.458 | 1.784 | 99.380 |

The dose is shown in terms of ONO-1301.
** P <0.05   vs Group 1

Bleomycin was intratracheally administered in an amount of 10 μg/animal (day 0)
a): Physiological saline was intratracheally administered in an amount of 40 μg/animal.

Bleomycin was intratracheally administered in an amount of 10 μg/animal (day 0)
a): Physiological saline was intratracheally administered in an amount of 40 μg/animal.

Fig. 30

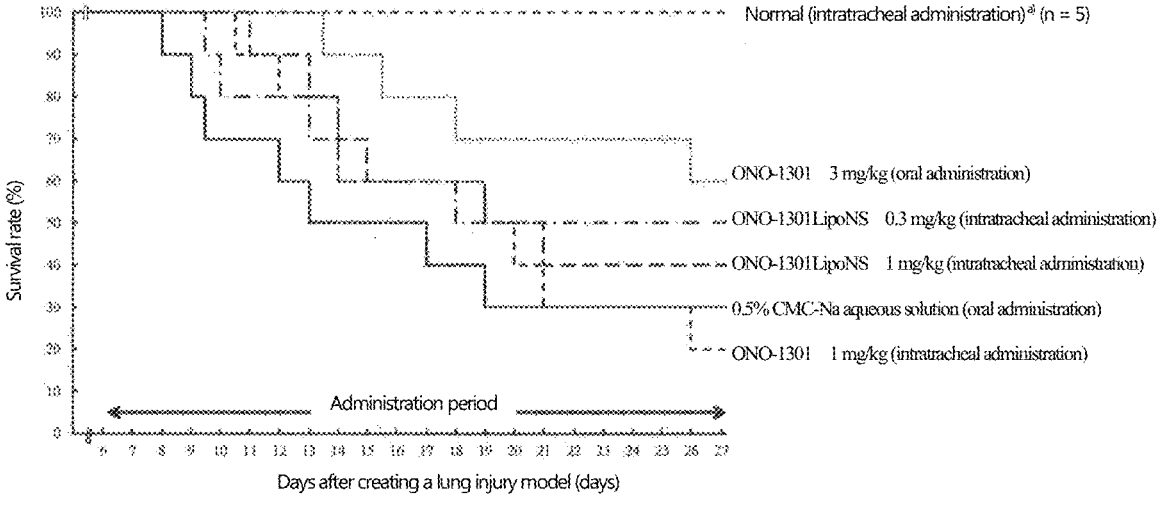

Days after creating a lung injury model (days)

Bleomycin was intratracheally administered in an amount of 10 μg/animal (day 0).
a): Physiological saline was intratracheally administered in an amount of 40 μg/animal.

Fig. 31

Sectioning of isolated heart          Left ventricle wall thickness and area extraction method

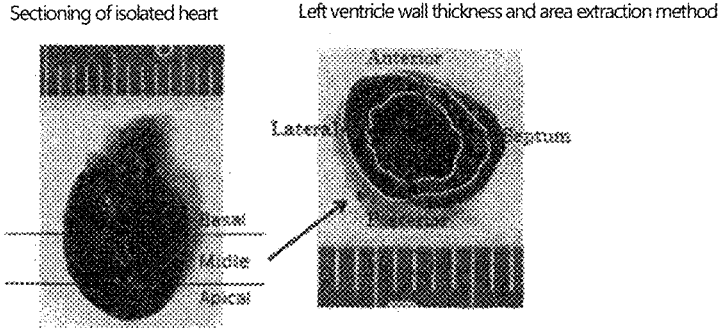

Fig. 32

Sectioning of isolated heart          Area ratio evaluation          Left ventricular outer diameter
                                                                     ratio evaluation

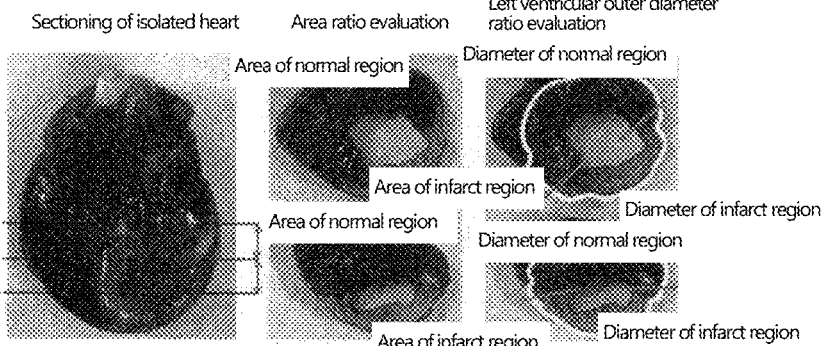

DISEASE-SITE-SPECIFIC LIPOSOMAL FORMULATION

CROSS REFERENCE TO RELATED APPLICATIONS

This application is a continuation of U.S. application Ser. No. 16/766,992, filed May 26, 2020, which is a 35 U.S.C. § 371 National Stage Entry of PCT/JP2017/042350, filed Nov. 27, 2017, the content of each of which is incorporated herein by reference in its entirety.

TECHNICAL FIELD

The present invention relates to a disease-site-specific liposomal formulation.

BACKGROUND ART

Compound (A) (ONO-1301) is a low-molecular-weight compound having both PGI2 receptor (IP) agonism and thromboxane (TX) A2 synthase inhibitory activity. Compound (A), which has PGI2 agonistic activity, is known to be useful for prevention and/or treatment of thrombosis, arteriosclerosis, ischemic heart disease, gastric ulcer, hypertension, etc. (Patent Literature (PTL) 1).

On the other hand, prostaglandin (PG) I2 receptor (IP) agonists, prostaglandin EP2 agonists, and prostaglandin EP4 agonists, such as ONO-1301, can be used as endogenous repair factor production promoters for many diseases at low doses by inducing many body regeneration factors, such as a hepatocyte growth factor (HGF), a vascular endothelial cell growth factor (VEGF), a stromal cell-derived factor (SDF-1), and a high-mobility group box protein 1 (HMGB1); and these agonists are known to be useful as regenerative therapies (Patent Literature (PTL) 2).

However, since there are concerns about side effects of compound (A), such as diarrhea following oral administration, and vasodilation and hypotensive effects in intravenous administration, the development of a dosage form that is capable of preventing exposure to a high concentration in the gastrointestinal tract or a rapid increase of the blood concentration, placing less burden on the patient, and maximizing drug efficacy is strongly desired. In the development of long-term sustained-release injectable formulations, many studies have been conducted on methods for controlling drug release by microspheres (hereinafter sometimes abbreviated as MS) with an average particle diameter of about 30 μm, containing a drug and using a poorly water-soluble polymer. A biodegradable polymer is used as the polymer so that the base does not remain at the site of administration after drug release. In particular, for example, polylactic acid polymers (hereinafter sometimes abbreviated as PLA) and lactic acid-glycolic acid copolymers (hereinafter sometimes abbreviated as PLGA), which have been used in surgical sutures, bone-fixing bolts, etc., are used. These biodegradable polymers are used in the LH-RH derivative injectable formulation Leuplin (sold by Takeda Pharmaceutical Co., Ltd.) and the long-acting somatostatin derivative Sandostatin LAR (sold by Novartis Pharmaceuticals).

Drugs used in microspheres include bioactive peptides, various hormones, growth factors, antibodies, peptides such as genes and various cell growth/differentiation inducing factors, proteins, nucleic acids, and the like. Compound (A)

(Patent Literature (PTL) 3), and compound (B) and compound (C) (Patent Literature (PTL) 4) are known as low-molecular compounds.

These drugs can be administered, for example, by intramuscular administration, subcutaneous injection, or patch application to various organs, of an MS formulation; in a dosage form that can continuously maintain the drug concentration in the tissue at a disease site, or in a dosage form that can maintain the blood concentration, such as intravenous infusions. When administered at a disease site, these formulations for administration maintain a high drug concentration in the vicinity of an administration site, and exhibit intravenous infusion-like blood kinetics; and do not have a drug delivery system (DDS) effect, which is an effect of accumulating a drug at a disease site. Specifically, DDS is a technique for delivering a required amount of a drug to a required place at a required time.

On the other hand, there is a known lung disease site-specific therapeutic agent whose mechanism is such that intravenous injection of a small amount of an MS formulation accumulates the MS formulation in the lungs and allows gradual release of a drug in the lungs, thereby maintaining a high concentration of the drug in the lungs (Patent Literature (PTL) 4). However, this method has a risk such that mass administration may cause the development of a pulmonary embolism, and thus has a safety problem.

As a method for alleviating these problems and providing DDS effects in a disease site-specific manner, the production of a nanosphere (hereinafter sometimes abbreviated as NS) formulation containing, for example, a PGI2 receptor agonist, such as compound (A), has been considered. There are many known methods for producing NS formulations. NS formulations are known as DDS formulations, which are intravenously administered to utilize vascular permeability enhancement action at inflammatory sites, ischemic sites, and/or cancer tissues; and utilize disease site-specific drug accumulation. However, the production of a clinically applicable NS formulation comprising a PGI2 receptor agonist, such as compound (A), has been difficult due to the stability, content, yield, safety, sustained release rate, efficacy, etc., of the formulation. In addition, it was extremely difficult to produce an NS formulation containing compound (A) capable of accumulation at a disease site and exhibiting the effect.

Methods for producing an NS formulation are roughly classified into breakdown methods and build-up methods. Breakdown methods are methods of pulverizing particles by spray-drying or a like method to reduce the particle size to submicron size. Build-up methods are known to produce, for example, polymer capsule formulations comprising a lactic acid-glycolic acid copolymer (PLGA), a lactic acid polymer (PLA). etc.; drug-encapsulating micelle formulations comprising micellar nanoparticles (polymer micelles) that have a two-layer structure comprising a block copolymer (copolymer) formed by combining polyethylene glycol (PEG) and a polyamino acid; hydrogel formulations produced by cross-linking gelatin, collagen, or a polymer mixture of hyaluronic acid, alginic acid, and the like, to form a hydrogel, and immobilizing a cell growth factor or the like in the hydrogel; and liposomal formulations having a drug encapsulated in various phospholipids.

When fine particles have a size as small as several nanometers or less, the particles are excreted from the kidney into urine, and cannot be retained in the body. On the other hand, when fine particles have a size of 400 nm or more, the fine particles are quickly eliminated from the body due to the immune mechanism of eliminating foreign matter by macrophages or the like. Therefore, as an NS formulation containing a drug, an NS formulation of several nanometers to 400 nm is recommended due to its enhanced permeation and retention effect (EPR effect). More specifically, unlike normal vascular endothelial cells, there is a wide gap of about 200 nm between vascular endothelial cells in cancer tissue or at an inflammation or ischemic site; it is known that a microparticle formulation having a size controlled to about 100 nm, or a polymer formulation, can be accumulated in tissue of vascular lesions created by cancer, infectious disease, ischemia, inflammation, arteriosclerosis, rheumatism, or the like. Thus, as an NS formulation having a DDS effect, there is known a method of forming an NS formulation having a particle size adjusted to 50 nm to 200 nm to allow a drug to reach a lesion site and release the drug at the lesion site, thus enhancing its therapeutic effect. Further, as an endocytosis effect, NS formulations are known to pass through a cell membrane and exhibit effects in cells. It is known to produce, for example, an oral nanosphere formulation having calcitonin encapsulated in lactic acid-glycolic acid copolymer (PLGA) nanoparticles (Non-patent Literature (NPL 1)); a transpulmonary nanosphere formulation having calcitonin encapsulated in chitosan nanoparticles (NPL 2); a topical nanosphere formulation having steroid encapsulated in PLGA nanoparticles (NPL 3); and a nanosphere formulation having an anti-inflammatory agent or a mitochondrial injury inhibitor encapsulated in lactic acid-glycolic acid copolymer (PLGA) nanoparticles. Such nanosphere formulations are effective for treating ischemic reperfusion injury (Patent Literature (PTL) 5). Further, a nanosphere formulation having prostaglandin E1 or a derivative thereof encapsulated in lactic acid-glycolic acid copolymer (PLGA) nanoparticles is also known (PTL 6 and NPL 4). Further, a nanosphere formulation comprising beraprost encapsulated in lactic acid-glycolic acid copolymer (PLGA) nanoparticles is known to be effective for pulmonary hypertension (PTL 7).

Since an encapsulated drug is released from such a PLGA or PLA nanoparticle formulation by hydrolysis of a lactic acid-glycolic acid bond with water, a nanoparticle formulation having a large surface area has a very short drug-release time. In contrast, the liposomal formulation gradually releases the drug through enzymatic degradation by lipase etc. in vivo.

A pharmaceutical composition comprising, as an active ingredient, a liposome in which an immunosuppressive agent, such as FK506, FTY720, or cyclosporin A, is encapsulated is also known to be effective for treating cardiovascular inflammatory diseases, such as myocardial infarction, myocarditis, and vasculitis syndrome (PTL 8). Doxil (produced by Janssen Pharmaceutical K.K.) comprising doxorubicin (an anticancer antibiotic) encapsulated in liposomes has already been commercially available as an anticancer drug. This pharmaceutical composition is also commercially available for other purposes, such as an antifungal agent, a Kaposi's sarcoma inhibitor, a lymphomatous meningitis inhibitor, an age-related macular degeneration inhibitor, and a postoperative pain inhibitor. LipoPGE$_1$, which is encapsulated in lipid microspheres in the form of an o/w emulsion of prostaglandin E1 comprising egg yolk lecithin, oleic acid, olive oil, and glycerin, is already commercially available (Ripple, sold by Mitsubishi Tanabe Pharma Corporation) (NPL 4). LipoPGE$_1$, which has an average particle size as large as 200 to 300 nm and has no stealth property, is trapped by the liver and macrophages, and thus has a short blood retention time.

On the other hand, no stealth liposomal formulation comprising a prostaglandin I2 receptor agonist and having an average particle size of 50 to 200 nm has been reported.

CITATION LIST

Patent Literature

PTL 1: JPH6-87811A
PTL 2: WO2004/032965
PTL 3: WO2008/047863
PTL 4: WO2014/069401
PTL 5: WO2016/006577
PTL 6: WO2010/058669
PTL 7: JP2012-171883A
PTL 8: WO2013/176223

Non-Patent Literature

NPL 1: Y. Kawashima, H. Yamamoto, H. Takeuchi and Y. Kuno, Pharm. Develop. Technol., 5, 77-85, (2000)
NPL 2: Y. Kawashima, 6th US-Japan Symposium on Drug Delivery Systems, Dec. 16-21, (2001), Maui
NPL 3: E. Horisawa et al., Pharm. Res., 19, 132-139, (2002)
NPL 4: J Pharm Pharmacol., 2013 August; 65(8):1187-94

SUMMARY OF INVENTION

Technical Problem

An object of the present invention is to provide a disease site-specific stealth liposomal formulation that is effective for treating a cardiovascular disease, such as ischemic and dilated cardiomyopathy, obstructive arteriosclerosis, vasculitis syndrome, valvular disease, aortic stenosis, chronic heart failure, or diastolic dysfunction; a respiratory disease, such as pulmonary hypertension, pulmonary fibrosis, asthma, or chronic obstructive pulmonary disease; a gastrointestinal or urinary disease, such as chronic kidney disease, chronic hepatitis, or chronic pancreatitis; and a neurodegenerative disease, such as cerebral infarction chronic stage, Alzheimer's disease, diabetic neuropathy, Parkinson's disease, or amyotrophic lateral sclerosis.

More specifically, an object of the present invention is to provide a clinically applicable, safe and convenient, stealth liposomal formulation, which is a liposome (LP) formulation containing, for example, a PGI2 receptor agonist compound (A), and which is intermittently administered by intravenous injection, inhalation, or the like; and thereby specifically accumulated at a disease site, thus exhibiting a DDS effect.

Solution to Problem

The present inventors conducted extensive research on the production of NS formulations having a PGI2 receptor (IP) agonist encapsulated therein. As a result, the inventors found that a stealth liposome (hereinafter sometimes abbreviated as LP) formulation is the optimum formulation to achieve this object. Through the research of many production methods, the inventors found an LP formulation that is clinically applicable in terms of stability, content percentage, yield, safety, efficacy, release, stealth properties, and the like, from among LP formulations containing compound (A) or the like. More specifically, the inventors found that a liposomal formulation that is a microparticle drug carrier coated with, for example, PEG-modified phosphoethanolamine and phospholipids can improve drug release control and stability, as well as exhibit new functions, such as accumulation at a disease site (targeting) and adhesion to tissue; thus significantly improving bioavailability (BA) and drug efficacy and thereby providing an increased effect at a lower dose than each component used alone, and reducing side effects.

The present inventors conducted intensive research to solve the above problems, and found for the first time that in a liposomal formulation containing a PGI2 receptor (IP) agonist, such as compound (A), an appropriate combination of: the types and composition ratio of lipids such as a phospholipid component and PEG-modified phosphoethanolamine having stealth properties; the average particle size of the liposomal formulation; the weight ratio of compound (A) or the like to the phospholipid; etc., surprisingly allows for the control of the release rate of a PGI2 receptor agonist, such as compound (A), which is a low molecular compound, and thus improves accumulation at a disease site, thereby exhibiting a DDS effect.

The present inventors further found that a specific combination of lipids allows the liposomal formulation to retain stealth properties, so that liposomes can escape capture by macrophages or the like. Further, the inventors found that the method of the present invention can reliably produce a stealth liposomal formulation with a high yield. The present invention has been accomplished through further trial and error based on these findings, and includes the following inventions.

Item 1

A pharmaceutical composition for disease site-specific treatment, comprising a stealth liposome having a prostaglandin I2 receptor agonist encapsulated therein.

Item 2

The pharmaceutical composition according to Item 1, wherein the prostaglandin I2 receptor agonist includes at least a compound represented by formula (I):

$$ \text{(I)} $$

wherein is (i)

-continued (ii)

(iii)

or (iv)

(wherein e represents an integer of 3 to 5, f represents an integer of 1 to 3, p represents an integer of 1 to 4, q represents 1 or 2, and r represents an integer of 1 to 3);

$R^1$ represents a hydrogen atom or a $C_{1-4}$ alkyl group;

$R^2$ represents (i) a hydrogen atom, (ii) a $C_{1-8}$ alkyl group, (iii) a phenyl group or a $C_{4-7}$ cycloalkyl group, (iv) a 4- to 7-membered monocyclic ring containing one nitrogen atom, (v) a $C_{1-4}$ alkyl group substituted with a benzene ring or a $C_{4-7}$ cycloalkyl group, or (vi) a $C_{1-4}$ alkyl group substituted with a 4- to 7-membered monocyclic ring containing one nitrogen atom; and $R^3$ represents (i) a $C_{1-8}$ alkyl group, (ii) a phenyl group or a $C_{4-7}$ cycloalkyl group, (iii) a 4- to 7-membered monocyclic ring containing one nitrogen atom, (iv) a $C_{1-4}$ alkyl group substituted with a benzene ring or a $C_{4-7}$ cycloalkyl group, or (v) a $C_{1-4}$ alkyl group substituted with a 4- to 7-membered monocyclic ring containing one nitrogen atom;

(provided that when is a group represented by (iii) or (iv), $-(C-(CH_2)_p-$ and $=CH-(CH_2)_s-$ are bound to position a or b on the ring, and cyclic structures in $R^2$ and $R^3$ are optionally substituted with one to three $C_{1-4}$ alkyl groups, $C_{1-4}$ alkoxy groups, halogen atoms, nitro groups, or trihalomethyl groups); or a salt thereof.

Item 3

The pharmaceutical composition according to Item 1, wherein the prostaglandin I2 receptor agonist includes at least the following compound (A):

(A)    ({5-[2-({[(1E)-phenyl(pyridin-3-yl)methylene]amino}oxy)ethyl]-7,8-dihydronaphthalen-1-yl}oxy)acetic acid (ONO-1301) represented by formula (II):

(II)

or a salt of compound (A).

Item 4

The pharmaceutical composition according to Item 1, wherein the prostaglandin I2 receptor agonist includes at least one of the following compounds (B) to (E):

(B) sodium (±)-(1R,2R,3aS,8bS)-2,3,3a,8b-tetrahydro-2-hydroxy-1-[(E)-(3S,4RS)-3-hydroxy-4-methyl-1-octen-6-ynyl]-1H-cyclopenta[b]benzofuran-5-butano-ate (beraprost); or a derivative thereof that is a carbacyclic PGI2 derivative, (C) MRE-269, (D) (2E)-7-{(1R,2R,3R)-3-hydroxy-2-[(1E,3S,5S)-3-hydroxy-5-methylnon-1-en-1-yl]-5-oxycyclopentyl}hept-2-enoic acid (limaprost), omoprostil, enprostil, or misoprostol; or a derivative of any of these compounds that is a PEF derivative, and (E) NS-304 (selexipag);

or a salt of any of compounds (B) to (E).

Item 5

The pharmaceutical composition according to Item 1, wherein the prostaglandin I2 receptor agonist includes at least one member selected from the group consisting of ONO-1301, beraprost, limaprost, and NS-304.

Item 6

The pharmaceutical composition according to any one of Items 1 to 5, wherein the stealth liposome is obtainable by using at least a prostaglandin I2 receptor agonist and a phospholipid by the Bangham method, hydration dispersion method, reverse phase evaporation method, ethanol injection method, ethanol dilution method, homogenization method, mechanochemical method, direct dispersion method, extruder method, French press method, remote loading method, dehydration-rehydration method, freeze-thaw method, ultrasonic method, or lipid-compound film method; or a modified method of any of these methods.

Item 7

The pharmaceutical composition according to any one of Items 1 to 6, wherein the stealth liposome has an average particle size of 50 to 200 nm, and comprises 5 to 50 parts by weight of the phospholipid and 0.05 to 5 parts by weight of PEG-modified phosphoethanolamine, per part by weight of the prostaglandin I2 receptor agonist.

Item 8

The pharmaceutical composition according to any one of Items 1 to 7, wherein the stealth liposome comprises 0.05 to 5 parts by weight of MPEG2000-DSPE per part by weight of the prostaglandin I2 receptor agonist; the prostaglandin I2 receptor agonist includes at least one member selected from the group consisting of ONO-1301, beraprost, limaprost, and NS-304; and the stealth liposome releases the prostaglandin I2 receptor agonist over a period of 3 hours to 4 weeks.

Item 9

The pharmaceutical composition according to any one of Items 1 to 8, wherein the stealth liposome comprises a prostaglandin I2 receptor agonist, a phospholipid, a PEG-modified phosphoethanolamine, and a water-miscible organic solvent, and does not comprise a sterol;

the liposome is obtainable by a production method comprising the following steps (1) to (8):

(1) mixing the prostaglandin I2 receptor agonist, the phospholipid, and the PEG-modified phosphoethanolamine in the solvent in amounts such that at least 5 mg of the phospholipid and at least one 0.05 mg of the PEG-modified phosphoethanolamine are present per mg of the prostaglandin receptor agonist, (2) heating the mixture obtained in step (1) to prepare a melt, (3) instantly freezing the melt obtained in step (2), (4) freeze-drying the frozen product obtained in step (3) to remove the solvent, (5) heating the freeze-dried product obtained in step (4) to disperse the heated product in an aqueous phosphate buffer solution, (6) sizing the dispersion obtained in step (5) with an extruder, (7) ultrafiltrating the dispersion obtained in step (6) to remove unencapsulated material, and (8) adding a sugar to the dispersion obtained in step (7) and freeze-drying the dispersion; and the liposome contains at least 0.001 mg of the prostaglandin I2 receptor agonist per 1.0 mg of the phospholipid and has an average particle size of 50 to 200 nm.

Item 10

The pharmaceutical composition according to any one of Items 1 to 9, wherein the composition is for intravenous administration, intracoronary administration, inhalation, intramuscular injection, subcutaneous administration, oral administration, transmucosal administration, transdermal administration, or an internal organ; and is in the form of an injectable formulation, an oral preparation, an inhalant, a nebulizer, an ointment, a patch, or a spray.

Item 11

The pharmaceutical composition according to any one of Items 1 to 9, wherein a single intravenous dose of the composition is 0.001 to 100 mg in terms of the prostaglandin I2 receptor agonist.

Item 12

The pharmaceutical composition according to Item 11, wherein a disease to be treated with the composition is cardiovascular disease, respiratory disease, urinary disease, gastrointestinal disease, bone disease, neurodegenerative disease, vascular disease, dental disease, eye disease, skin disease, other inflammatory disease, ischemic organ disorder, diabetic complication, tissue fibrotic disease, tissue degenerative disease, or hair loss; and the composition comprises a liposome.

Item 13

The pharmaceutical composition according to Item 11, wherein the disease to be treated with the composition is a cardiovascular disease such as ischemic and dilated cardiomyopathy, atherosclerosis obliterans, vasculitis syndrome, valvular disease, aortic stenosis, chronic heart failure, or diastolic failure; a respiratory lung disease such as pulmonary hypertension, pulmonary fibrosis, asthma, or chronic obstructive pulmonary disease; a gastrointestinal or urinary disease such as chronic kidney disease, chronic hepatitis, or chronic pancreatitis; or a neurodegenerative disease such as chronic phase of cerebral infarction, Alzheimer's disease, diabetic neuropathy, Parkinson's disease, or amyotrophic lateral sclerosis; and the composition comprises a liposome.

Advantageous Effects of Invention

According to the present invention, there can be provided a pharmaceutical composition that is effective for, for example, cardiovascular diseases, respiratory diseases, gastrointestinal or urinary diseases, and inflammatory diseases such as neurodegenerative diseases, ischemic organ disorders, diabetic complications, tissue fibrotic diseases, tissue degenerative disease, or hair loss. The pharmaceutical composition of the present invention can have the effect of enhancing drug efficacy at a lower dose than a single use of a PGI2 receptor agonist, and also reducing side effects. Further, the present invention can provide a stealth liposomal formulation that allows for accumulation of a PGI2 receptor agonist in a high concentration at a disease site, and exhibit effects in a sustained manner; and provide a method for producing the stealth liposomal formulation.

The liposomal formulation of the present invention containing compound (A) or the like is effective for circulatory diseases, respiratory diseases, urinary diseases, gastrointestinal diseases, and neurodegenerative diseases, when intermittently administered by intravenous administration, intramuscular administration, subcutaneous administration, or inhalation administration. In particular, the liposomal formulation administered intravenously or by inhalation is accumulated at a disease site and topically exhibits an endogenous repair factor production-promoting action, thus being useful as a regenerative drug. Intravenous administration of the liposomal formulation is useful for heart diseases, such as myocardial infarction, angina, dilated cardiomyopathy, aortic stenosis, valvular disease, chronic heart failure, and diastolic dysfunction, due to its vasodilator action, angiogenesis action, stem cell differentiation-inducing action, antifibrotic action, antiapoptotic action, reverse remodeling action, etc. For pulmonary diseases or the like such as acute pneumonia, chronic pneumonia, pulmonary hypertension, pulmonary fibrosis, interstitial pneumonia, COPD, and ARDS, inhalation administration, in addition to intravenous administration, is useful. For neurodegenerative diseases such as amyotrophic lateral sclerosis (ALS), Parkinson's disease, Alzheimer's disease, and spinal cord injury, intramedullary administration, in addition to intravenous administration, is useful.

BRIEF DESCRIPTION OF DRAWINGS

FIG. 11 is transmission electron microscope images of Formulation 21.

FIG. 12 is charts of HPLC measurement of Samples 1 to 5.

FIG. 19 is diagrams showing the average particle size distribution of Formulations 24 and 25.

FIG. 20 shows the results of HPLC analysis.

FIG. 30 is a graph showing a comparison with intermittent intratracheal administration of Formulation 25 (ONO-1301Lipo).

FIG. 31 is a drawing showing a method for evaluating a left ventricle wall thickness and a left ventricle wall area.

FIG. 32 is photographs showing an infarct area evaluation method.

DESCRIPTION OF EMBODIMENTS

Figure 1:
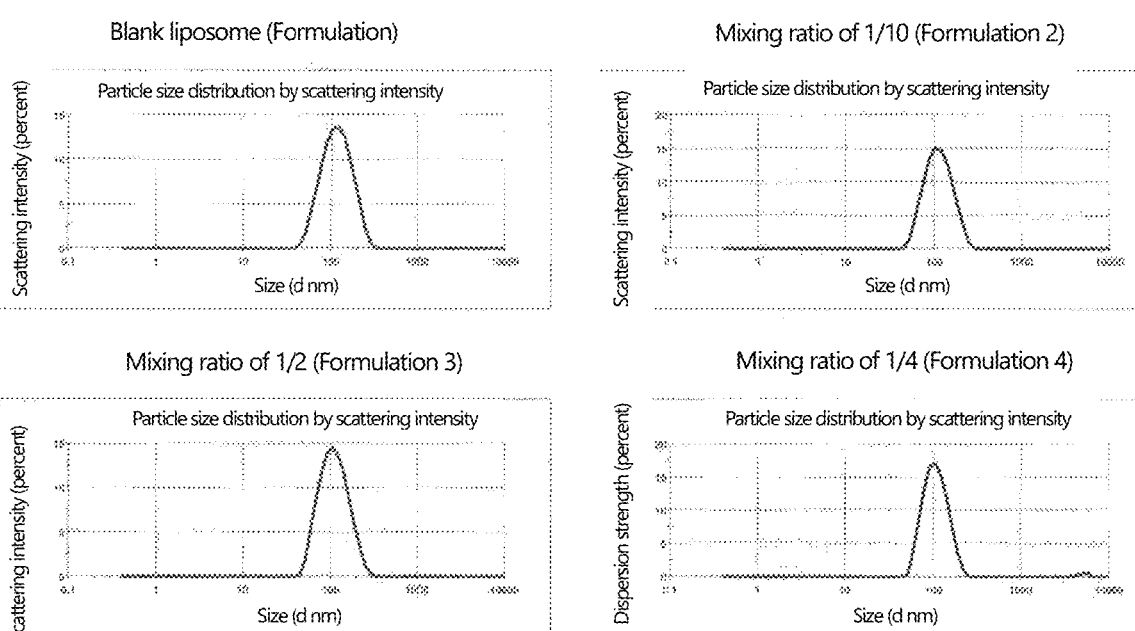
FIG. 1 is diagrams showing the average particle size distribution of Formulations 1 to 4.

The liposomes used in the pharmaceutical composition of the present invention are not limited, as long as they are closed vesicles surrounded by a lipid bilayer. The liposomes may be large unilamellar vesicle (LUV) liposomes, or small unilamellar vesicle (SUV) liposomes; and may be multilamellar vesicle (MLV) liposomes. The liposomes can be produced by known production methods.

There are three types of methods for producing liposomes. More specifically, the Bangham method is commonly used as a liposome production method. There are also methods comprising the Bangham method and some additional operations, which are called the simple hydration method, ultrasonic treatment method, and extrusion method. Examples of liposome production methods further include the direct dispersion method, organic solvent (e.g., ethanol) injection method, reverse phase evaporation method, calcium fusion method, surfactant removal method, static hydration method, hexane-span 80 dialysis method, organic solvent globule evaporation method, mechanochemical method, ultrasonic method, lipid-compound film method, and the like; and improved methods of these methods.

The method for adjusting the particle size includes the extrusion method, extrusion process, French press method, and the like. Examples of the extruder method or the French press method includes a method comprising passing particles several times through a nanopore membrane filter having an appropriate pore size, which is set in an extruder or a French press to adjust the liposome size.

Examples of the method for encapsulating the compound include the pH gradient (remote loading) method, counter ion concentration gradient (gelation) method, freeze-thaw method, supercritical carbon dioxide method, film loading method, and the like.

The methods that are superior in encapsulating a water-soluble drug include the reverse phase evaporation method and the freeze-thaw method. The methods that are superior in encapsulating fat-soluble drugs include the Bangham method, the mechanochemical method, the supercritical carbon dioxide method, and the film loading method. The methods that are superior in encapsulating dissociative drugs include the pH gradient (remote loading) method, the counterionization concentration gradient method, and the like.

The Bangham method includes, for example, a method comprising forming a lipid film; and then applying a mechanical vibration by vortexing, ultrasonic waves, or the like in an aqueous buffer to form liposomes (a hydration dispersion method). The reverse phase evaporation method includes, for example, a method comprising dissolving a lipid in an organic solvent that is immiscible with water; then adding an aqueous buffer and performing ultrasonic treatment to form a reverse micelle (a W/O emulsion), thereafter removing the organic solvent by vacuum treatment or the like and achieving a gel state; and then forming liposomes. The ethanol injection method or the ethanol dilution method includes, for example, a method comprising dissolving a lipid in ethanol, and injecting a lipid solution into an aqueous buffer to form liposomes.

The homogenization method or the mechanochemical method includes, for example, a method of forming liposomes by using a high-pressure emulsifier.

The direct dispersion method includes a method comprising directly dispersing a lipid or a mixture of a lipid and a compound in an aqueous buffer, without preparing a lipid film, to form liposomes.

Among the methods for adjusting the particle size, the extruder method or the French press method includes, for example, a method comprising passing the liposomes through a nanopore membrane set in an extruder or a French press to thereby adjust the liposome size.

Among the methods of encapsulating the compound, the remote loading method is an encapsulation method utilizing the difference in pH solubility of the compound. More specifically, after liposomes having as an inner aqueous phase a pH solution in which the compound is water-soluble are formed, the outer aqueous phase is replaced with a pH solution in which the compound is fat-soluble by ultrafiltration, dialysis, or the like; and adding a compound solution to the liposome dispersion to thereby encapsulate the compound in the aqueous phase of the liposomes. The dehydration-rehydration method is an encapsulation method in which liposomes are dehydrated by freeze-drying or the like; and then rehydrated with an aqueous buffer containing a compound to be encapsulated, thereby encapsulating the compound.

The freeze-thawing method includes, for example, a method comprising mixing a liposome dispersion and a compound solution to be encapsulated, and repeating freeze-thaw cycles to thereby encapsulate a compound at a high concentration.

The method for producing liposomes is not limited to the production methods described above. The method further includes improved methods of each of these methods, and the like.

The lipids that form liposomes are not particularly limited. Examples of lipids include soy lecithin, hydrogenated soy lecithin, egg yolk lecithin, phosphatidylcholines, phosphatidylserines, phosphatidylethanolamines, phosphatidylinositols, phosphasphingomyelins, phosphatidic acids, long-chain alkyl phosphates, gangliosides, glycolipids, phosphatidylglycerols, sterols, and the like. Lipids can be used singly, or in a combination of two or more. Examples of phosphatidylcholines include dimyristoylphosphatidylcholine, dipalmitoylphosphatidylcholine, distearoylphosphatidylcholine, and the like. Examples of phosphatidylserines include dipalmitoyl phosphatidylserine, sodium dipalmitoylphosphatidylserine, bovine brain-derived sodium phosphatidylserine, and the like. Examples of phosphatidylethanolamines include dimyristoyl phosphatidylethanolamine, dipalmitoylphosphatidylethanolamine, distearoylphosphatidylethanolamine, and the like. Examples of the phosphatidylinositols include wheat-derived phosphatidylinositol sodium, and the like. Examples of phosphasphingomyelins include bovine-derived sphingomyelin, and the like. Examples of phosphatidic acids and long-chain alkyl phosphates include dimyristoyl phosphatidic acid, dipalmitoyl phosphatidic acid, distearoyl phosphatidic acid, dicetyl phosphoric acid, and the like. Examples of gangliosides include ganglioside GM1, ganglioside GD1a, ganglioside GT1b, and the like. Examples of glycolipids include galactosylceramide, glucosylceramide, lactosylceramide, phosphatide, globoside, and the like. Examples of phosphatidyl glycerol include dimyristoyl phosphatidyl glycerol, dipalmitoyl phosphatidyl glycerol, distearoyl phosphatidyl glycerol, and the like. Examples of sterols include cholesterol, dihydrocholesterol, lanosterol, dihydrolanosterol, sitosterol, campesterol, stigmasterol, brassicasterol, ergosterol, and the like. When two or more lipids are used in combination, a phospholipid and cholesterol are preferably used in combination. The phospholipid is preferably a phosphatidylcholine. When liposomes are produced by using a phospholipid and cholesterol, the molar ratio of the phospholipid to cholesterol is preferably in the range of 1:0.1 to 1:1.5, and more preferably 1:0.5 to 1:1.25.

Examples of phospholipids that can be used in the present invention include the following commercially available products (sold by Nippon Fine Chemical Co., Ltd.).

In general, the phospholipid is preferably DOPC or DEPC, although it may vary depending on the substance to be encapsulated therein.

13

TABLE 1

| Abbreviated product name | IUPAC name | Cas Reg. No. |
|---|---|---|
| DPPC | 1,2-Dipalmitoyl-sn-glycero-3-phosphocholine | 63-89-8 |
| DSPC | 1,2-Distoaroyl-sn-glycero-3-phosphocholine | 816-94-4 |
| DMPC | 1,2-Dimyristoyl-sn-glycerol-3-phosphocholine | 18194-24-6 |
| DOPC | 1,2-Dioleoyl-sn-glycero-3-phosphocholine | 4235-96-4 |
| DBPC | 1,2-Dieracoyl-sn-Glycero-3-Phosphocholine | 51779-95-4 |
| POPC | 2-Oleoyl-1-palmitoyl-sn-glycero-3-phosphocholine | 26853-31-6 |
| PCS | 1,2-Diacyl-sn-Glycero-3-Phosphocholine (SOY) | 8002-43-5 |
| PCSH | 1,2-Diacyl-sn-Glycero-3-Phosphocholine (SOY) | 8002-43-5 |
| DPPG | 1,2-Dipalmitoyl-sn-Glycero-3-[Phospho-rac-(1-glycerol)] (Sodium Salt) | 67233-81-9 |
| DMPG | 1,2-Dimyristoyl-sn-Glycero-3-[Phospho-rac-(1-glycerol)] (Sodium Salt) | 67232-80-8 |
| DSPG | 1,2-Distearoyl-sn-Glycero-3-[Phospho-rac-(1-glycerol)] (Sodium Salt) | 4537-78-4 |
| DOPG | 1,2-Dioleoyl-sn-Glycero-3-[Phospho-rac-(1-glycerol)] (Sodium Salt) | 62706-09-0 |
| PGE | 1,2-Diacyl-sn-Glycero-3-[Phospho-rac-(1-glycerol)] (Sodium Salt, EGG) | N/A |
| PGS | 1,2-Diacyl-sn-Glycero-3-{Phospho-rac-(1-glycerol)] (Sodium Salt, SOY) | N/A |
| PGSH | 1,2-Diacyl-sn-Glycero-3-[Phospho-rac-(1-glycerol)] (Sodium Salt, SOY) | N/A |

Conventional liposomal formulations are liposomes comprising typical phospholipid and cholesterol. There are also stealth liposomes whose surface is modified with polyethylene glycol (PEG) or the like to increase the blood retention. These liposomes have the effect of accumulation specifically at a disease site due to their EPR effects.

To increase the stability (stealth properties) of liposomes in blood, the liposome membrane surface is preferably modified with a polyethylene glycol (PEG) derivative. The liposomes modified with a PEG derivative can be produced by using a covalent conjugate of PEG having a molecular weight of 500 to 20000 and a phospholipid. The covalent conjugate of PEG and phospholipid is preferably a PEG-modified phosphoethanolamine, which is a conjugate of PEG having a molecular weight of 200 to 5000 and distearoylphosphatidylethanolamine.

Examples of PEG-modified phosphoethanolamines include commercially available products, such as DMPE (1,2-dimyristoyl-sn-glycero-3-phosphoethanolamine), DPPE (1,2-dipalmitoyl-sn-glycero-3-phosphoethanolamine), DSPE (1,2-distearoyl-sn-glycero-3-phosphoethanolamine), DOPE (1,2-dioleoyl-sn-glycero-3-phosphoethanolamine), and the like (all produced by Nippon Fine Chemical Co., Ltd.), which comprise mPEG 350, mPEG 550, mPEG 750, mPEG 1000, mPEG 2000, mPEG 3000, or mPEG 5000 as a PEG-modifying group.

A preferable combination is, for example, a combination of mPEG2000-DSPE: N-(carbonyl-methoxypolyethyleneglycol 5000)-1,2 distearoyl-sn-glycero-3-phosphoethanolamine, sodium salt CAS No. 147867-65-0 (produced by Nippon Fine Chemical Co., Ltd.) and DEPC: 1,2-dierucoyl-sn-glycerol-3-phosphorylcholine CAS No. 51779-95-4 (produced by Nippon Fine Chemical Co., Ltd.).

The contents of the PEG-modified phosphoethanolamine and phospholipid are not particularly limited. The content of the PEG-modified phosphoethanolamine is preferably 0.01% to 10%, and more preferably 0.01% to 3%, relative to the phospholipid as 1.

There is also a method in which the liposome surface is modified with PEG and a targeting molecule, such as an antibody or a peptide, to increase blood retention and further enhance the transfer to a target site.

The present invention provides a stealth liposome characterized in that the liposome contains a PGI2 receptor agonist and a phospholipid, and further comprises PEG-modified phosphoethanolamine. The liposome is preferably formed into a liposomal formulation by combining a PGI2 receptor agonist and a phospholipid, and further EG-modified phosphoethanolamine, according to the purpose; and mixing these components at an appropriate ratio.

The stealth liposome comprises a prostaglandin I2 receptor agonist, a phospholipid, a PEG-modified phosphoethanolamine, and a water-miscible solvent; and can be produced, for example, by a production method comprising the following steps:

mixing a prostaglandin I2 receptor agonist, a phospholipid, and a PEG-modified phosphoethanolamine in a water-miscible solvent in amounts such that at least 5 mg of the phospholipid and at least 0.05 mg of the PEG-modified phosphoethanolamine are present per mg of the prostaglandin I2 receptor agonist, to prepare a mixture;

heating the mixture to prepare a melt;

instantly freezing the melt;

freeze-drying the frozen product to remove the solvent;

heating the freeze-dried product to disperse the heated product in an aqueous phosphate buffer solution;

sizing the dispersion with an extruder;

ultrafiltrating the dispersion to remove unencapsulated material; and adding a sugar to the dispersion, and freeze-drying the dispersion.

The liposomes produced by this method are a stealth liposomal formulation characterized by containing a PGI2 receptor agonist, and having an average particle size of 50 to 200 nm.

The mixture of the PGI2 receptor agonist, the phospholipid, PEG-modified phosphoethanolamine, and solvent may or may not contain a sterol, such as cholesterol. Conventional liposomes preferably comprise a combination of a phospholipid and cholesterol as constituent lipids. However, the present invention uses no cholesterol as a constituent lipid, and thereby makes it possible to produce liposomes in which a PGI2 receptor agonist is stably encapsulated at a high concentration.

The size (particle size) of the liposomes is not particularly limited. The liposomes preferably have an average particle size of about 10 to 1000 nm, more preferably about 20 to 500 nm, and even more preferably about 50 to 200 nm. The "particle size" referred to herein means the diameter of a particle determined by the dynamic light scattering method. A preferable polydispersity index (PDI) is 0.3 or less. The method for adjusting the particle size is not particularly limited.

The present invention provides a prophylactic and/or therapeutic agent for a cardiovascular disease, a respiratory disease, a urinary disease, a vascular disease, a gastrointestinal disease, a neurodegenerative disease, etc., which comprises, as an active ingredient, liposomes having a PGI2 receptor agonist encapsulated therein. The PGI2 receptor agonist used in the pharmaceutical composition of the present invention is not particularly limited; a known PGI2 receptor agonist can be preferably used. Examples of known PGI2 receptor agonists include, for example, pharmaceutical compositions, PGI2 derivatives, and PGE derivatives, which are compounds represented by the following formula (I):

(I)

wherein is (i)

(ii)

(iii)

or (iv)

(wherein e represents an integer of 3 to 5,
f represents an integer of 1 to 3,
p represents an integer of 1 to 4,
q represents 1 or 2, and
r represents an integer of 1 to 3);
$R^1$ represents a hydrogen atom or a $C_{1-4}$ alkyl group;
$R^2$ represents (i) a hydrogen atom, (ii) a $C_{1-8}$ alkyl group, (iii) a phenyl group or a $C_{4-7}$ cycloalkyl group, (iv) a 4- to 7-membered monocyclic ring containing one nitrogen atom, (v) a $C_{1-4}$ alkyl group substituted with a benzene ring or a $C_{4-7}$ cycloalkyl group, (vi) a $C_{1-4}$ alkyl group substituted with a 4- to 7-membered monocyclic ring containing one nitrogen atom; and $R^3$ represents (i) a $C_{1-8}$ alkyl group, (ii) a phenyl group or a $C_{4-7}$ cycloalkyl group, (iii) a 4- to 7-membered monocyclic ring containing one nitrogen atom, (iv) a $C_{1-4}$ alkyl group substituted with a benzene ring or a $C_{4-7}$ cycloalkyl group, (v) a $C_{1-4}$ alkyl group substituted with a 4- to 7-membered monocyclic ring containing one nitrogen atom;
(provided that when is a group represented by (iii) or (iv),
—(C—(CH$_2$)$_p$— and =CH—(CH$_2$)$_s$— are bound to position a or b on the ring, and cyclic structures in $R^2$ and $R^3$ are optionally substituted with one to three $C_{1-4}$ alkyl groups, $C_{1-4}$ alkoxy groups, halogen atoms, nitro groups, or trihalomethyl groups); and salts thereof.
Preferably, the PGI2 receptor agonist is one of the following compounds:

(A)    ({5-[2-({[(1E)-phenyl(pyridin-3-yl)methylene]amino}oxy)ethyl]-7,8-dihydronaphthalen-1-yl}oxy) acetic acid (CAS 176391-41-6; compound (A) (ONO-1301)) represented by formula (II):

(II)

(B) carbacyclic PGI2 derivatives such as sodium (±)-(1R, 2R,3aS,8bS)-2,3,3a,8b-tetrahydro-2-hydroxy-1-[(E)-(3S,4RS)-3-hydroxy-4-methyl-1-octene-6-ynyl]-1H-cyclopenta[b]benzofuran-5-butanoate (CAS: 88475-69-8; beraprost)(compound (B));
(C) [4-(5,6-diphenylpyrazinyl)(1-methylethyl)amino]butoxy]-acetic acid (CAS: 475085-57-5; MRE-269; compound (C));
(D) PGE derivatives such as (2E)-7{-(1R,2R,3R)-3-hydroxy-2[-(1E,3S,5S)-3-hydroxy-5-methylnon-1-en-1-yl]-5-oxocyclopentyl}-hept-2-enoic acid (CAS: 74397-12-9; limaprost), omoprostil; 17S,20-dimethyl-6-oxo-PGE$_1$ methyl ester, emprostil, and misoprostol (compound (D)); and
(E)    2-{4-[(5,6-diphenylpyrazin-2-)yl)(propan-2-yl)amino]butoxy}-N-(methanesulfonyl)acetamide (CAS: 475086-01-2; selexipag; NS-304 (compound (E)).
The subject to which the pharmaceutical composition of the present invention is administered is preferably a mammal having an inflammatory disease, ischemic organ disorder, diabetic complication, tissue fibrotic disease, tissue degenerative disease, or the like. Examples of mammals include humans, monkeys, cows, sheep, goats, horses, pigs, rabbits, dogs, cats, rats, mice, guinea pigs, and the like.

Humans that have developed an inflammatory disease, or humans suspected to have an inflammatory disease, are particularly preferable.

The method for administering the pharmaceutical composition of the present invention is not particularly limited, as long as the active ingredient can reach a disease site. Examples include injectable formulations, patches, inhalants, nebulizers, sprays, gels, creams, sprays, ointments, nasal drops, eye drops, and the like, which are for intravenous administration, intracoronary administration, drip/infusion, intracoronary administration, inhalation, intramuscular administration, subcutaneous administration, oral administration, suppositories, intraperitoneal administration, transmucosal administration, transdermal administration, or internal organs. For intraarterial administration, intracoronary administration is preferable. For intravenous administration, peripheral intravenous administration is preferable.

The injectable formulation may be either an aqueous injectable formulation or an oily injectable formulation. The aqueous injectable formulation can be prepared by a known method. For example, after liposomes having a drug encapsulated therein are mixed into a solution prepared by appropriately adding pharmaceutically acceptable additives to an aqueous solvent (e.g., water for injectable formulation or purified water), the resulting mixture is filtered through a filter or the like and sterilized, and the filtrate is filled into an aseptic container. Examples of pharmaceutically acceptable additives include isotonic agents such as sodium chloride, potassium chloride, glycerin, mannitol, sorbitol, boric acid, borax, glucose, and propylene glycol; buffers such as phosphoric acid buffer, acetic acid buffer, boric acid buffer, carbonic acid buffer, citric acid buffer, Tris buffer, glutamic acid buffer, and epsilon-aminocaproic acid buffer, preservatives such as methyl paraoxybenzoate, ethyl paraoxybenzoate, propyl paraoxybenzoate, butyl paraoxybenzoate, chlorobutanol, benzyl alcohol, benzalkonium chloride, sodium dehydroacetate, sodium edetate, boric acid, and borax; thickeners such as hydroxyethyl cellulose, hydroxypropyl cellulose, polyvinyl alcohol, and polyethylene glycol; stabilizers such as sodium bisulfite, sodium thiosulfate, sodium edetate, sodium citrate, ascorbic acid, and dibutylhydroxytoluene; pH adjusters such as hydrochloric acid, sodium hydroxide, phosphoric acid, and acetic acid; and the like. The injectable formulation may further comprise an appropriate solubilizing agent. Examples of the solubilizing agent include alcohols such as ethanol; polyalcohols such as propylene glycol and polyethylene glycol; nonionic surfactants such as polysorbate 80, polyoxyethylene (50) hydrogenated castor oil, lysolecithin, and pluronic polyol; and the like. The injectable preparation may comprise a protein such as bovine serum albumin or key hole limpet hemocyanin; a polysaccharide such as aminodextran; and the like. When an oily injectable formulation is to be produced, for example, sesame oil or soybean oil can be used as an oily solvent; and benzyl benzoate, benzyl alcohol, or the like can be added as a solubilizing agent. The prepared injectable formulation is usually placed in, for example, an appropriate ampoule or vial. Liquid formulations such as injectable formulations can also be preserved after removing water by cryopreservation, lyophilization, or the like. Lyophilized formulations are dissolved again at the time of use by adding distilled water for injectable formulations or the like; and then used.

The amount of the drug or the like contained in the pharmaceutical composition of the present invention varies depending on the dosage form, administration interval, or administration route. In the case of the injectable formulation for intravenous administration, the amount can be appropriately selected from the range of 0.001 ng/ml to 100 mg/mL. The administration period and administration method are appropriately determined according to the disease and the treatment method therefor, in consideration of safety, convenience, low invasiveness, patient's burden, compliance, and the like. Any administration interval may be used as long as the effect can be expected and the administration interval is convenient. The administration interval is preferably about twice a day, every day, once every two days, once every three days, once a week, once every two weeks, once every three weeks, or once every four weeks; and is more preferably in the range of once a day to once a week.

For example, when liposomes having compound (A) encapsulated therein are intravenously administered to a human that has developed a heart disease, a single dose in terms of ONO-1301 is preferably 500 mg or less, and more preferably 100 mg or less. The lower limit is not particularly limited, and can be any dose that provides the desired effect.

When a PGI2 receptor agonist alone is administered at a high dose, the PGI2 receptor exhibits a hypotensive effect due to its vasodilatory effect; therefore, there is little deviation from the effective amount. In contrast, the pharmaceutical composition of the present invention, which comprises, as an active ingredient, liposomes having a PGI2 receptor agonist encapsulated therein, is useful in that the liposomal formulation can exhibit effects on many diseases even at a low dose due to its accumulation at a disease site by the DDS effect. That is, vascular permeability at a lesion site, and nano-sized liposomes can be expected to specifically accumulate in the lesion site (EPR effect). Furthermore, the liposomal formulation is highly useful in that since the drug moves into cells due to the endocytosis effect, an increase in drug efficacy and a reduction in side effects can be expected. Further, the pharmaceutical composition of the present invention is useful in that an active ingredient can be delivered to a target lesion site by administration through a peripheral vein or the like, without the necessity of using a central venous catheter or the like. Another advantage is that the pharmaceutical composition is difficult to be delivered to sites other than the target site even when administered through a peripheral vein. In other words, the pharmaceutical composition of the present invention is highly useful in that the composition can provide an enhanced tissue repair effect at a low dose; and can reduce side effects by reducing the dose, suppressing delivery to sites other than the target site, and eliminating the necessity of using a central venous catheter or the like.

When a liposomal formulation is to be produced by the direct dispersion improvement method, and when a premix of lipids is produced, the solvent used must meet the following conditions: it is a solvent in which lipids and the substance to be encapsulated are soluble; it can be instantly frozen; and it can be removed by freeze-drying. Any solvent that satisfies the above conditions can be used.

In general, the solvent is preferably t-butanol, cyclohexane+ethanol, hexafluoropropanol, 1-propanol, isopropyl alcohol, 2-butoxyethanol, and the like. t-Butanol is more preferable.

In the freeze-drying of liposomes, it is generally necessary to add and disperse a sugar, such as maltose, sucrose, or trehalose, to thereby inhibit cell membrane collapse on freezing and perform freeze-drying.

Application to Pharmaceutical Products

PGI2 receptor agonists, such as compound (A), have, for example, an in vivo regeneration factor production-promoting action, stem cell differentiation-inducing action, anti-apoptotic action, reverse remodeling action, anti-fibrotic action, and angiogenesis-promoting action. Therefore, stealth liposomal formulations containing such a PGI2 receptor agonist are useful as therapeutic and/or prophylactic agents for the following various diseases:

various organ disorders, inflammatory diseases such as vascular diseases (e.g., atherosclerosis obliterans (ASO), Berger disease, Raynaud's disease, arteriosclerosis, vasculitis syndrome, etc.), cardiovascular diseases (e.g., myocardial infarction, myocarditis, angina, supraventricular tachyarrhythmia, congestive heart failure, coronary artery disease, idiopathic cardiomyopathy, dilated cardiomyopathy, ischemic cardiomyopathy, atrial fibrillation, chronic heart failure, diastolic dysfunction, systolic dysfunction, valvular disease, aortic stenosis, etc.), neurodegenerative diseases (e.g., ischemic encephalopathy, cerebrovascular disease, stroke, Parkinson's disease, Alzheimer's disease, diabetic neuropathy, spinal canal stenosis, dementia, moyamoya disease, spinal cord injury, muscle atrophy lateral sclerosis (ALS) etc.), respiratory diseases (e.g., acute pneumonia, pulmonary fibrosis, pulmonary hypertension, chronic obstructive pulmonary disease (COPD), systemic inflammatory response syndrome (SIRS), acute lung injury (ALI), acute respiratory distress syndrome (ARDS), Sarcoidosis, interstitial pneumonia, irritable pneumonia, asthma, refractory asthma, etc.), bone diseases (e.g., osteoarthritis (OA) of, for example, spine or knee, rheumatoid arthritis (RA), osteoporosis, fracture, spinal cord injury, periosteal injury, etc.), gastrointestinal liver diseases (e.g., fulminant hepatitis, acute hepatitis, cirrhosis, chronic hepatitis, fatty liver, steatohepatitis, gastric ulcer, gastritis, intestinal ulcer, etc.), urinary diseases (e.g., acute renal failure, chronic renal failure, glomerular disease, tubulointerstitial disease, renal vasculopathy, cystic kidney disease, toxic nephropathy, tubule transport abnormality, dialysis patient kidney disorders, nephropathy, nephrotic syndrome, IgA nephropathy, atypical hemolytic uremic syndrome, acute progressive nephritis syndrome, renal fibrosis, etc.), gastrointestinal pancreatic diseases (e.g., diabetes, chronic pancreatitis, acute pancreatitis, etc.), gastrointestinal diseases (e.g., esophagitis, gastritis, gastric ulcer, duodenal ulcer, ulcerative colitis, Crohn's disease, etc.), diabetic complications (e.g., diabetic neuropathy, skin ulcer, diabetic nephropathy, diabetic retinopathy, etc.), vascular endothelial cell damages (e.g., prevention of restenosis after percutaneous transluminal coronary angioplasty (PTCA)), dental diseases (e.g., periodontal diseases, tooth extraction wounds, oral wounds, periodontal tissue disorders, etc.), skin diseases (e.g., pressure ulcers, hair loss, etc.), ophthalmic diseases (e.g., glaucoma, etc.), organ/cell transplantation (e.g., heart, liver, kidneys, lungs, pancreas, pancreatic islet cells, bone marrow, etc.), chronic transplant rejection, and the like. In particular, the liposomal formulation of the present invention has shown promise as a prophylactic and/or therapeutic agent for heart diseases, lung diseases, kidney diseases, bone diseases, neurodegenerative diseases, liver diseases, pancreatic diseases, autoimmune diseases, allergic syndromes, and vascular diseases.

As body regeneration factors whose product is induced or promoted by a PGI2 receptor agonist, such as compound (A), for example, the following factors are known: a vascular endothelial cell growth factor (VEGF), a hepatocyte growth factor (HGF), various fibroblast growth factors (a/bFGF), transforming growth factor-β (TGF-β), a platelet-derived growth factor (PDGF), Angiopoietin, a hypoxia-inducible factor (HIF), an insulin-like growth factor (IGF), a bone morphogenetic protein (BMP), a connective tissue growth factor (CTGF), an epidermal growth factor (EGF), a stromal cell-derived factor (SDF-1), a high-mobility group box 1 (HMGB1), and the like; and growth factors of their families etc. Examples of other drugs that produce endogenous repair factors described above include other PGI2 receptor agonists, EP2 and EP4 receptor agonists of PGE2 receptors, and mixed receptor agonists thereof; and the like. To achieve the object of the present invention, the drugs mentioned above may be used in place of compound (A). Examples of the drug that can be used in place of compound (A) include PGI and PGE derivatives, IP, EP2 and EP4 receptor agonists, and the like. Specific examples include compound (B), aeroprost, ornoprostil, compound (C), compound (D) (limaprost), compound (E), enprostil, misoprostol, ONO-4232, ONO-8055, and the like.

These drugs and liposomes containing the drugs exhibit effects on the same diseases as those on which compound (A) has effects.

It is also preferable in the present invention that two or more drugs selected from compound (A) and drugs described above are combined according to the purpose, and formed into liposomes. The drugs may be commercially available, or can be easily produced in accordance with a known method.

The dosage form of the liposome of the present invention includes injectable formulations, ointments, patches, oral preparations, sprays, and the like, which are for intravenous administration, coronary artery administration, inhalation, intramuscular administration, subcutaneous administration, oral administration, transmucosal administration, and transdermal administration, or internal organs. In addition to the above, other examples include implants, transmucosal agents for administration through the rectum, uterus, oral cavity, or the like, nasal drops, and intravenous drip injections; or a method for continuous administration into coronary arteries.

Toxicity

As compared with the PGI2 receptor agonist alone, the liposomal formulation of the present invention is less toxic and fully safe for use as a medicament. Further, the PGI2 receptor agonist has been confirmed not to have carcinogenesis initiation and promotion effects in a long-term carcinogenicity test, a medium-term hepatocarcinogenicity test, etc., using mice and rats.

EXAMPLES

The present invention is described in detail below with reference to Examples; however, the present invention is not limited to these Examples.

The following are the reagents used. In the Examples, these reagents are referred to by the following abbreviations.

(1) HSPC (hydrogenated soybean phospholipid, hydrogenated lecithin), product name: COATSOME NC-21 (NOF corporation), CAS: 921228-87-5, 92128-87-5

(2) DSPE (1,2-Distearoyl-sn-glycero-3-phosphoethanolamine), CAS: 1069-79-0 (Nippon Fine Chemical Co., Ltd.)

(3) DEPC: 1,2-Dierucoyl-sn-glycerol-3-phosphorylcholine, CAS: 51779-95-4 (Nippon Fine Chemical Co., Ltd.)

(4) MPEG2000-DSPE: N-(carbonyl-methoxypolyethyleneglycol-5000)-1,2 distearoyl-sn-glycero-3-phosphoethanolamine, sodium salt, CAS: 147867-65-0 (Nippon Fine Chemical Co., Ltd.)

(5) DOPC: 1,2-Dioleoyl-sn-glycero-3-phosphocholine, CAS: 4235-95-4 (Nippon Fine Chemical Co., Ltd.)

(6) Cholesterol: Cholesterol HP (NOF Corporation)

(7) PBS(−): Dulbecco's phosphate buffered saline (without Ca and Mg), filtered and sterilized, tested for mycoplasma and endotoxin (product code: 14249-95) (Nacalai Tesque Inc.)

The PGI2 receptor agonists to be encapsulated in liposome are commercially available from the companies listed below, and can be purchased generally.

(i) Compound (A): (ONO-1301), Sigma-Aldrich, CAS: 176391-41-6

(ii) Compound (B): (Beraprost), Cayman Chemical Company, CAS: 88475-69-8

(iii) Compound (C): (MRE-269), Cayman Chemical Company, CAS: 475085-57-5

(iv) Compound (D): (Limaprost), Cayman Chemical Company, CAS: 74397-12-9

(v) Compound (E): (NS-304), Cayman Chemical Company, CAS: 475086-01-2

Below, examples of the production of liposomes of PGI2 receptor agonists are specifically described in detail.

1. Formulation Example 1 (Remote Loading Method) Preparation of Liposome

5) Compound (A) (56.5 mg) was weighed, and 1.41 mL of a 0.1N sodium hydroxide solution was added thereto. The mixture was dissolved by vortexing, and 5.65 mL of a 10 mM phosphate buffer (pH: 8.0) was added thereto to thus prepare a solution of 8 mg/mL (compound (A) solution).

6) The compound (A) solution was added to the liposome solution (three concentration conditions), and the mixtures were stirred at 60° C. for 1 hour.

7) The three concentration conditions (the solution volume: 3 mL) were a 1/10 mixing ratio: 3.29 mg of the compound and 32.9 mg of the lipids; a 2/10 mixing ratio: 6.58 mg of the compound and 32.9 mg of the lipids; and a 4/10 mixing ratio: 13.16 mg of the compound and 32.9 mg of the lipids.

8) Free compound (A) was removed by ultrafiltration (cutoff molecular weight: 300,000 Da) using a stirred cell (8000 series, a 10-mL cell): Model 8010 5121 produced by Merck & Co., Inc., and BioMax PBMK 02510 produced by Merck & Co., Inc. The external solution was a 10 mM phosphate buffer (pH: 7.4).

As a result, liposomal formulations having four different properties shown in Table 2 below were obtained. FIG. 1 is diagrams showing the average particle size distribution of these formulations.

TABLE 2

| | | Average particle size (Z-Ave, nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formulation 1 | Blank liposome | 109 | 0.121 | −67 | 8.44 | — | — | — |
| Formulation 2 | Mixing ratio of 1/10 | 105 | 0.105 | −29 | 5.40 | 0.12 | 0.02 | 2.2 |
| Formulation 3 | Mixing ratio of 2/10 | 102 | 0.126 | −23 | 5.46 | 0.14 | 0.03 | 2.6 |
| Formulation 4 | Mixing ratio of 4/10 | 103 | 0.148 | −27 | 5.62 | 0.16 | 0.03 | 2.8 |

\* Content = calculated from the concentration of compound (A) per mg of lipid.

\* Physical property testing was performed after filtration through a 0.22 μm filter.

1) HSPC (107.4 mg), DSPE (9.0 mg), and cholesterol (35.3 mg) were weighed and placed in an eggplant flask, and a chloroform/methanol solution (1/1, v/v) was added and dissolved so that the lipid concentration was 20 mg/mL.

2) The chloroform/methanol was evaporated with a rotary evaporator, followed by vacuum-drying.

3) A 0.1N sodium hydroxide solution (>pH: 12.0) was added so that the lipid concentration was 10 mg/mL. The mixture was redispersed by vortexing, and subjected to ultrasonic treatment for 30 minutes in total using a VS-100III produced by AS ONE Corporation by repeating a cycle of 28 kHz output for 60 seconds, 45 kHz output for 60 seconds, and 100 kHz output for 3 seconds. After the ultrasonic treatment, the particle size was confirmed.

4) To exchange the liposome external solution, stirred ultrafiltration (cutoff molecular weight: 300,000 Da) was performed. The liposome external solution was a 10 mM phosphate buffer (pH: 8.0) (liposome solution). For ultrafiltration, a stirred cell (8000 series, a 50-mL cell): Model 8050 5122 produced by Merck & Co., Inc. and BioMax PBMK 04310 produced by Merck & Co., Inc. were used. After the preparation of empty liposomes, lipid quantification was performed.

2. Formulation Example 2 (Bangham Method) Preparation of Liposome

1) HSPC (102.0 mg), DSPE (8.5 mg), and cholesterol (33.5 mg) were weighed and placed in an eggplant flask, and a chloroform/methanol solution (1/1, v/v) was added and dissolved so that the lipid concentration was 20 mg/mL.

2) The chloroform/methanol was evaporated with a rotary evaporator, followed by vacuum-drying. Four eggplant flasks each containing 30 mg of the lipids in total were thus obtained.

3) Compound (A) (170.6 mg) was weighed, and 4.5 mL of a 0.1N sodium hydroxide solution was added thereto. The mixture was dissolved by vortexing, and 2.6 ml of 10 mM phosphate buffer (pH: 8.0) was added thereto to thus prepare a solution of 24 mg/mL (compound (A) solution).

4) The compound (A) solution was added to the vacuum-dried lipid film (three concentration conditions), followed by stirring at 37° C. for 1 hour. Since each eggplant flask contained 30 mg of the lipids, the amount of each solution was adjusted with PBS to 3 mL to achieve a 1/10 mixing ratio: 3.0 mg of compound (A) and 30 mg of the lipids; a 2/10 mixing ratio: 6 mg of compound (A) and 30 mg of the lipids; or a 4/10 mixing ratio: 12 mg of compound (A) and 30 mg of the lipids.

5) Treatment was performed for 60 minutes in total using a VS-100III, produced by AS ONE Corporation, by repeating a cycle of 28 kHz output for 60 seconds, 45 kHz output for 60 seconds, and 100 kHz output for 3 seconds.

6) Ultrasonic treatment was performed for 60 minutes.

7) Free compound (A) was removed by ultrafiltration (cutoff molecular weight: 300,000 Da) using a stirred cell (8000 series, a 10-mL cell): Model 8010 5121 produced by Merck & Co., Inc., and BioMax PBMK 02510 produced by Merck & Co., Inc.

The external solution was a 10 mM phosphate buffer (pH: 7.4).

Figure 2:
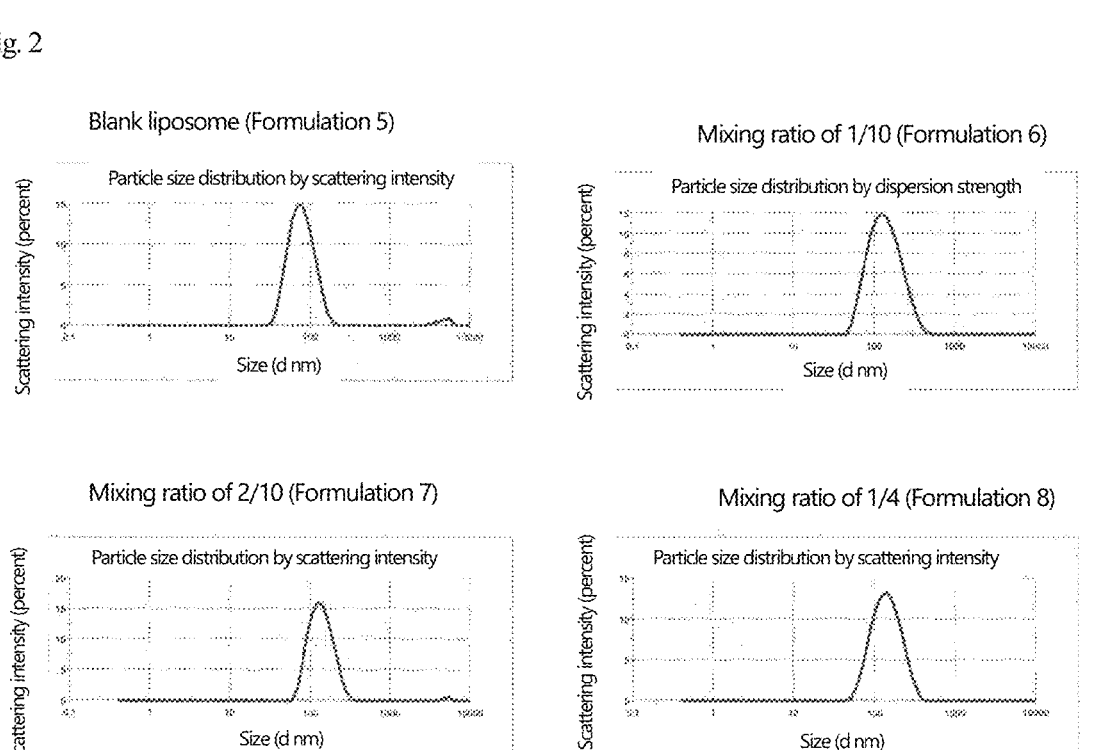
FIG. 2 is diagrams showing the average particle size distribution of Formulations 5 to 8.

As a result, liposomal formulations having four different properties shown in Table 3 below were obtained. FIG. 2 is diagrams showing the average particle size distribution of these formulations.

5) Ultrasonic treatment was performed at 28 kHz for 1 minute using a VS-100III produced by AS ONE Corporation so that the lipids on the wall of the eggplant flask were dispersed.

6) At 60° C., heating and stirring were performed for 30 minutes.

7) An equivalent amount of 10 mM phosphate buffer (pH: 8.0) was added, and extruder treatment was performed (60° C., 400 nm, 200 nm). The extruder was performed with a Lipex Thermobarrel Extruder (100 mL) produced by Northern Lipids, and with Nuclepore membranes produced by GE Healthcare (400 nm: Product No. 111107; 200 nm: Product No. 111106).

8) Free compound (A) was removed by ultrafiltration (cutoff molecular weight: 300,000 Da) using a stirred cell

TABLE 3

| | | Average particle size (Z-Ave. nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formulation 5 | Blank liposome | 75 | 0.172 | −23 | 8.12 | — | — | — |
| Formulation 6 | Mixing ratio of 1/10 | 123 | 0.162 | −30 | 6.47 | 0.07 | 0.011 | 1.1 |
| Formulation 7 | Mixing ratio of 2/10 | 132 | 0.146 | −32 | 6.76 | 0.08 | 0.012 | 1.2 |
| Formulation 8 | Mixing ratio of 4/10 | 129 | 0.142 | −32 | 6.66 | 0.21 | 0.032 | 3.2 |

\* Content = calculated from the concentration of compound (A) per mg of lipid.
\* Physical property testing was performed after filtration through a 0.22 μm filter.

3. Formulation Example 3 (Extruder Method) Preparation of Liposome

1) HSPC (255.0 mg), DSPE (21.3 mg), and cholesterol (83.0 mg) were weighed and placed in an eggplant flask, and a chloroform/methanol solution (1/1, v/v) was added and dissolved so that the lipid concentration was 20 mg/mL.

2) The chloroform/methanol was evaporated with a rotary evaporator, followed by vacuum drying.

(8000 series, a 50-mL cell): Model 8050 5122 produced by Merck & Co., Inc., and BioMax PBMK 04310 produced by Merck & Co., Inc.

The external solution was a 10 mM phosphate buffer (pH: 7.4).

Figure 3:
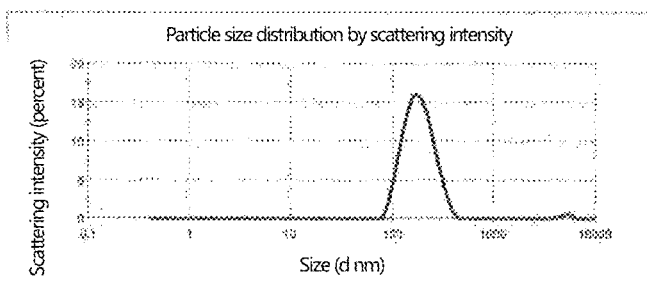
FIG. 3 is a diagram showing the average particle size distribution of Formulation 9.

As a result, a liposomal formulation having the properties shown in Table 4 below was obtained. FIG. 3 is a diagram showing the average particle size distribution of this formulation.

TABLE 4

| | | Average particle size (Z-Ave. nm) | PDI | Zeta potential (mV) | Lipid concentration (mg/mL) | Concentration of compound (A) (mg/mL) | Compound (A)/Lipid (mg/mL) | Content (%) |
|---|---|---|---|---|---|---|---|---|
| Formulation 9 | Mixing ratio of 4/10 | 175 | 0.147 | −11 | 5.12 | 0.153 | 0.030 | 3.0 |

\* Content = calculated from the concentration of compound (A) per mg of lipid.
\* Physical property testing was performed after filtration through a 0.22 μm filter.

3) Compound (A) (143 mg) was weighed, and 3.76 mL of a 0.1N sodium hydroxide solution was added thereto. The mixture was dissolved by vortexing, and 2.2 mL of a 10 mM phosphate buffer (pH: 8.0) was added thereto to thus prepare a solution of 24 mg/mL (compound (A) solution).

4) The compound (A) solution was added to the lipid film, and a 10 mM phosphate buffer (pH: 8.0) was added to increase the volume to 36 mL (compound (A): 140 mg, the lipids: 360 mg).

4. Formulation Example 4 (Lipid-Compound Film Method) Preparation of Liposome 1) Lipids (HSPC: 21.2 mg, DSPE: 1.8 mg, and cholesterol: 7.0 mg) and compound (A) (6.0 mg) were weighed and placed in an eggplant flask. At this time, the amounts were adjusted so that compound A) was present in an amount of 2 mg per 10 mg of the lipids.

2) A chloroform/methanol solution (1/1, v/v) was added and dissolved so that the total weight of the lipids and compound (A) was 20 mg/mL.

3) The chloroform/methanol was evaporated with a rotary evaporator, followed by vacuum-drying.

4) 10 mM phosphate buffer (pH 8.0) was added to the resulting product so that the lipid concentration was 10 mg/mL.

5) Ultrasonic treatment was performed at 28 kHz using a VS-100III produced by AS ONE Corporation to separate the lipids and compound (A) from the wall of the eggplant flask, and the mixture was stirred at 60° C. for 30 minutes.

6) An equivalent amount of 10 mM phosphate buffer (pH: 8.0) was added thereto, and extruder treatment was performed (60° C., 400 nm, 200 nm). More specifically, the extruder was performed with a Lipex Thermobarrel Extruder (100 mL) produced by Northern Lipids, and with Nuclepore membranes produced by GE Healthcare (400 nm: Product No. 111107; and 200 nm: Product No. 111106).

7) Free compound (A) was removed by ultrafiltration (cutoff molecular weight: 300,000 Da) using a stirred cell (8000 series, a 10-mL cell): Model 8010 5121 produced by Merck & Co., Inc., and BioMax PBMK 02510 produced by Merck & Co., Inc. The external solution was a 10 mM phosphate buffer (pH: 7.4).

Figure 4:
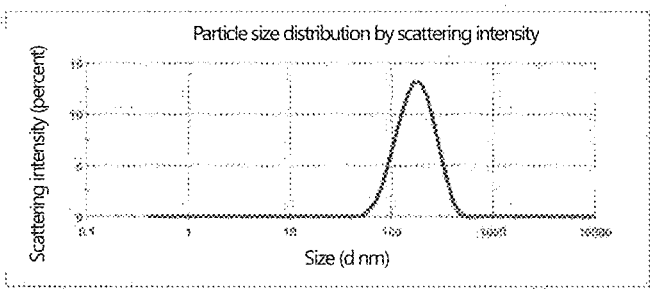
FIG. 4 is a diagram showing the average particle size distribution of Formulation 10.

As a result, a liposomal formulation having the properties shown in Table 5 below was obtained. FIG. 4 is a diagram showing the average particle size distribution of this formulation.

3) Ultrasonic treatment was performed for 30 minutes in total using a VS-100III produced by AS ONE Corporation by repeating a cycle of 28 kHz output for 60 seconds, 45 kHz output for 60 seconds, and 100 kHz output for 3 seconds. Thereafter, the particle size was confirmed.

4) To exchange the liposome external solution, stirred ultrafiltration (cutoff molecular weight: 300,000 Da) was performed. The liposome external solution was 10 mM phosphate buffer (pH: 8.0) (liposome solution).

The ultrafiltration was performed using a stirred cell (8000 series, a 50-mL cell): Model 8050 5122 produced by Merck & Co., Inc., and BioMax PBMK 04310 produced by Merck & Co., Inc. After the preparation of empty liposomes, lipid quantification was performed.

5) Compound (A) (56.5 mg) was weighed, and 1.41 mL of a 0.1N sodium hydroxide solution was added thereto. The mixture was dissolved by vortexing, and 5.65 mL of 10 mM phosphate buffer (pH: 8.0) was added thereto to thus prepare a solution of 8 mg/mL (compound (A) solution)

6) The compound (A) solution was added to the liposome solution (three concentration conditions), and the mixture was stirred at 60° C. for 1 hour. The three concentration conditions (solution volume: 4 mL) were a 1/10 mixing ratio: 4.0 mg of compound (A) and 40.0 mg of the lipids; a 2/10 mixing ratio: 8.0 mg of compound (A) and 40.0 mg of

TABLE 5

| | | Average particle size (Z-Ave. nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formu-lation 10 | Mixing ratio of 2/10 | 158 | 0.132 | −13 | 4.73 | 0.07 | 0.015 | 1.5 |

* Content = calculated from the concentration of compound (A) per mg of lipid.
* Physical property testing was performed after filtration through a 0.22 μm filter.

5. Production of PEG-Treated Stealth Liposomal Formulation (1) Formulation Example 5 (Remote Loading Method) Preparation of Liposome 1) HSPC (107.5 mg), MPEG2000-DSPE (35.0 mg), and cholesterol (35.5 mg) were weighed and placed in an eggplant flask, and a chloroform/methanol solution (1:1, v/v) was added and dissolved so that the lipid concentration was 30 mg/mL.

2) The chloroform/methanol was evaporated with a rotary evaporator, followed by vacuum-drying. Then, a 0.1N sodium hydroxide solution (>pH: 12.0) was added so that the lipid concentration was 10 mg/mL, and the mixture was redispersed by vortexing.

the lipids; and a 4/10 mixing ratio: 16.0 mg of compound (A) and 40.0 mg of the lipids.

7) Free compound (A) was removed by stirred ultrafiltration (cutoff molecular weight: 300,000 Da). Ultrafiltration was performed by using a stirred cell (8000 series, a 10-mL cell): Model 8010 5121 produced by Merck & Co., Inc., and BioMax PBMK 02510 produced by Merck & Co., Inc. The external solution was a 10 mM phosphate buffer (pH: 7.4).

Figure 5:
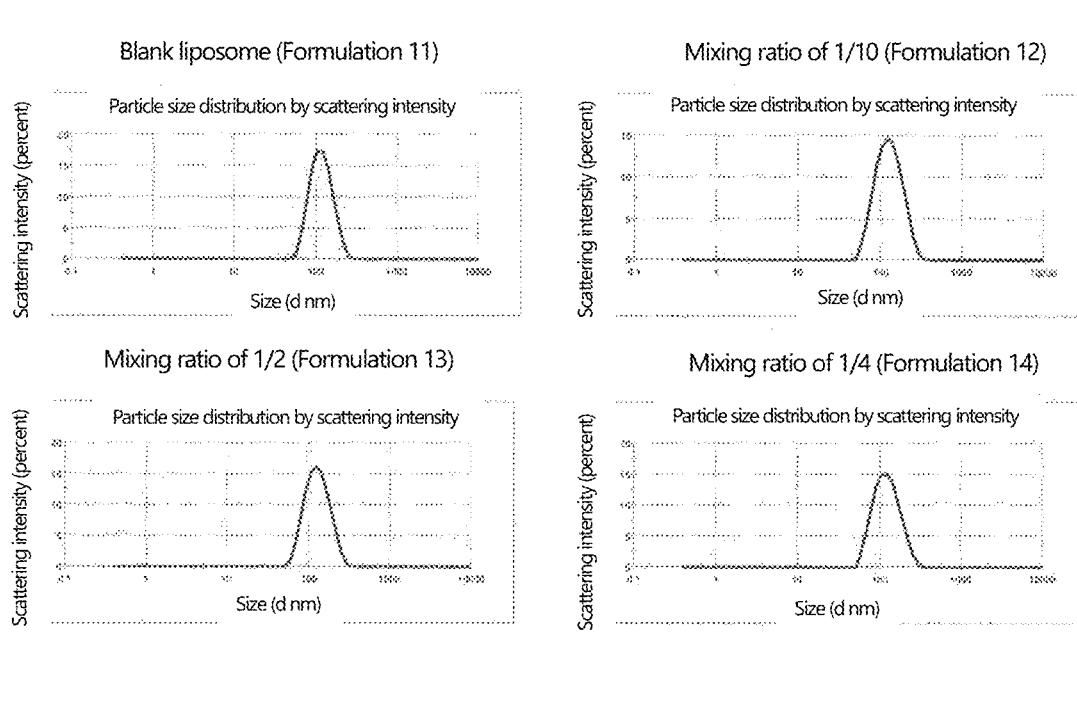
FIG. 5 is diagrams showing the average particle size distribution of Formulations 11 to 14.

As a result, liposomal formulations having four different properties shown in Table 6 below were obtained. FIG. 5 is diagrams showing the average particle size distribution of these formulations.

TABLE 6

| | | Average particle size (Z-Ave. nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formu-lation 11 | Blank liposome | 114 | 0.139 | −23 | 5.94 | — | — | — |
| Formu-lation 12 | Mixing ratio of 1/10 | 119 | 0.113 | −32 | 6.11 | 0.08 | 0.01 | 1.3 |
| Formu-lation 13 | Mixing ratio of 2/10 | 120 | 0.096 | −33 | 6.58 | 0.09 | 0.01 | 1.4 |

TABLE 6-continued

| | | Average particle size (Z-Ave. nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formu-lation 14 | Mixing ratio of 4/10 | 116 | 0.131 | −30 | 6.58 | 0.13 | 0.02 | 2.0 |

\* Content = calculated from the concentration of compound (A) per mg of lipid.
\* Physical property testing was performed after filtration through a 0.22 μm filter.

(2) Formulation Example 6 (Bangham Method) Preparation of Liposome

1) HSPC (87.0 mg), MPEG2000-DSPE (28.3 mg), and cholesterol (29.0 mg) were weighed and placed in an egg-plant flask, and a chloroform/methanol solution (1:1, v/v) was added and dissolved so that the lipid concentration was 30 mg/mL.

Merck & Co., Inc., and BioMax PBMK 02510 produced by Merck & Co., Inc. The external solution was a 10 mM phosphate buffer (pH: 7.4).

Figure 6:
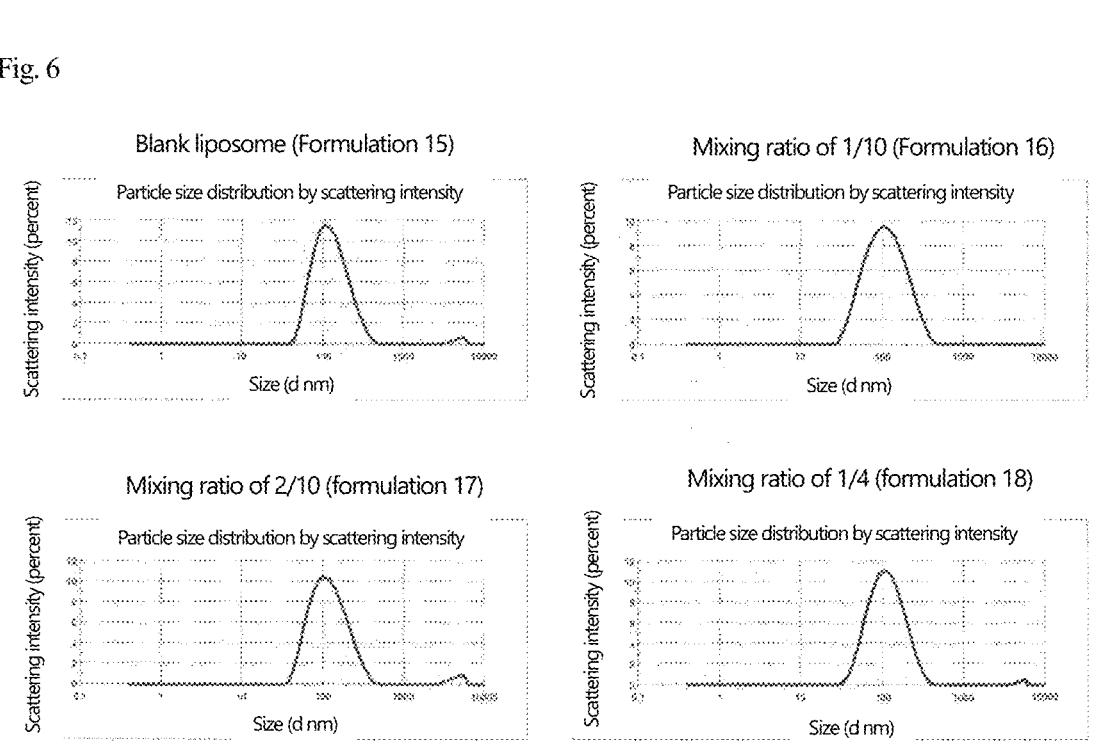
FIG. 6 is diagrams showing the average particle size distribution of Formulations 15 to 18.

As a result, liposomal formulations having four different properties shown in Table 7 below were obtained. FIG. 6 is diagrams showing the average particle size distribution of these formulations.

TABLE 7

| | | Average particle size (Z-Ave. nm) | PDI | Zeta potential (mV) | Lipid concen-tration (mg/mL) | Concentration of compound (A) (mg/mL) | Compound (A)/lipid (mg/mL) | Content (%) |
|---|---|---|---|---|---|---|---|---|
| Formu-lation 15 | Blank liposome | 115 | 0.205 | −48 | 7.58 | — | — | — |
| Formu-lation 16 | Mixing ratio of 1/10 | 95 | 0.213 | −45 | 8.57 | 0.07 | 0.009 | 0.9 |
| Formu-lation 17 | Mixing ratio of 2/10 | 110 | 0.243 | −48 | 6.93 | 0.17 | 0.024 | 2.4 |
| Formu-lation 18 | Mixing ratio of 4/10 | 102 | 0.221 | −43 | 7.77 | 0.27 | 0.035 | 3.5 |

\* Content = calculated from the concentration of compound (A) per mg of lipid.
\* Physical property testing was performed after filtration through a 0.22 μm filter.

2) The chloroform/methanol was evaporated with a rotary evaporator, followed by vacuum drying. Four eggplant flasks each containing 10 mg of the lipids in total were thus obtained.

3) Compound (A) (164 mg) was weighed, and 4.3 mL of a 0.1N sodium hydroxide solution was added thereto. The mixture was dissolved by vortexing, and 2.53 mL of 10 mM phosphate buffer (pH: 8.0) was added thereto to thus prepare a solution of 24 mg/mL (compound (A) solution).

4) The compound (A) solution was added to the vacuum-dried lipid film (three concentration conditions), followed by stirring at 37° C. for 1 hour.

5) The three concentration conditions (solution volume: 4 mL) were a 1/10 mixing ratio: 1.0 mg of compound (A) and 10.0 mg of the lipids; a 2/10 mixing ratio: 2.0 mg of compound (A) and 10.0 mg of the lipids; and a 4/10 mixing ratio: 4.0 mg of compound (A) and 10.0 mg of the lipids.

6) Ultrasonic treatment was performed for 60 minutes in total using a VS-100III produced by AS ONE Corporation by repeating a cycle of 28 kHz output for 60 seconds, 45 kHz output for 60 seconds, and 100 kHz output for 3 seconds.

7) Free compound (A) was removed by ultrafiltration (cutoff molecular weight: 300,000 Da) using a stirred cell (8000 series, a 10-mL cell): Model 8010 5121 produced by (3) Formulation Example 7 (Extruder Method) Preparation of Liposome 1) HSPC (215.0 mg), MPEG2000-DSPE (70.0 mg), and cholesterol (71.0 mg) were weighed and placed in an egg-plant flask, and a chloroform/methanol solution (1:1, v/v) was added and dissolved so that the lipid concentration was 30 mg/mL.

2) The chloroform/methanol solution was evaporated with a rotary evaporator, followed by vacuum-drying.

3) Compound (A) (142.7 mg) was weighed, and 3.8 mL of a 0.1N sodium hydroxide solution was added thereto. The mixture was dissolved by vortexing, and 2.19 mL of 10 mM phosphate buffer (pH: 8.0) was added thereto to thus prepare a solution of 24 mg/mL (compound (A) solution).

4) The compound (A) solution was added to the lipid film, and 10 mM phosphate buffer (pH: 8.0) was added thereto to increase the volume to 35.6 mL (compound (A): 142.4 mg, the lipids: 356.0 mg).

5) Ultrasonic treatment was performed for 1 minute and for 30 minutes in total using a VS-100III produced by AS ONE Corporation by repeating a cycle of 28 kHz output for 60 seconds, 45 kHz output for 60 seconds, and 100 kHz output for 3 seconds to separate the lipids from the wall of the eggplant flask, and the resulting product was stirred at 60° C. for 30 minutes.

6) An equivalent amount of 10 mM phosphate buffer (pH: 8.0) was added thereto, and extruder treatment was performed (60° C., 400 nm, 200 nm). The extruder was performed with a Lipex Thermobarrel Extruder (100 mL) produced by Northern Lipids, and with Nuclepore membranes produced by GE Healthcare (400 nm: Product No. 111107; 200 nm: Product No. 111106).

7) Free compound (A) was removed by ultrafiltration (cutoff molecular weight: 300,000 Da) using a stirred cell (8000 series, a 50-mL cell): Model 8050 5122 produced by Merck & Co., Inc., and BioMax PBMK 04310 produced by Merck & Co., Inc. The external solution was a 10 mM phosphate buffer (pH: 7.4).

Figure 7:
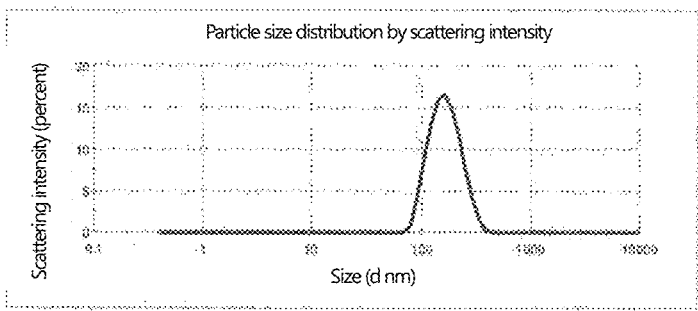
FIG. 7 is a diagram showing the average particle size distribution of Formulation 19.

As a result, a liposomal formulation having the properties shown in Table 8 below was obtained. FIG. 7 shows is diagrams showing the average particle size distribution of this formulation.

TABLE 8

|  |  | Average particle size (Z-Ave. nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formulation 19 | Mixing ratio of 4/10 | 158 | 0.114 | −35 | 5.03 | 0.128 | 0.025 | 2.5 |

\* Content = calculated from the concentration of compound (A) per mg of lipid.
\* Physical property testing was performed after filtration through a 0.22 μm filter.

(4) Formulation Example 8 (Lipid-Compound Film Method) Preparation of Liposome

1) HSPC (18.0 mg), MPEG2000-DSPE (6.0 mg), cholesterol (6.0 mg), and compound (A) (6.0 mg) were weighed and placed in an eggplant flask. At this time, the amounts were adjusted so that compound (A) was present in an amount of 2 mg per 10 mg of the lipids. Then, a chloroform/methanol solution (1/1, v/v) was added and dissolved so that the total weight of the lipids and compound (A) was 30 mg/mL.

2) The chloroform/methanol was evaporated with a rotary evaporator, followed by vacuum-drying.

3) 10 mM phosphate buffer (pH 8.0) was added to the resulting product so that the lipid concentration was 10 mg/mL.

4) Ultrasonic treatment was performed at 28 kHz using a VS-100III produced by AS ONE Corporation to separate the lipids and compound (A) from the wall of the eggplant flask, and the mixture was stirred at 60° C. for 30 minutes.

5) An equivalent amount of 10 mM phosphate buffer (pH: 8.0) was added thereto, and extruder treatment was performed (60° C., 400 nm, 200 nm). The extruder was performed with a Lipex Thermobarrel Extruder (100 mL) produced by Northern Lipids and with Nuclepore membranes produced by GE Healthcare (400 nm: Product No. 111107; 200 nm: Product No. 111106).

6) Free compound (A) was removed by ultrafiltration (cutoff molecular weight: 300,000 Da) using a stirred cell (8000 series, a 10-mL cell): Model 8010 5121 produced by Merck & Co., Inc., and BioMax PBMK 02510 produced by Merck & Co., Inc. The external solution was a 10 mM phosphate buffer (pH: 7.4).

Figure 8:
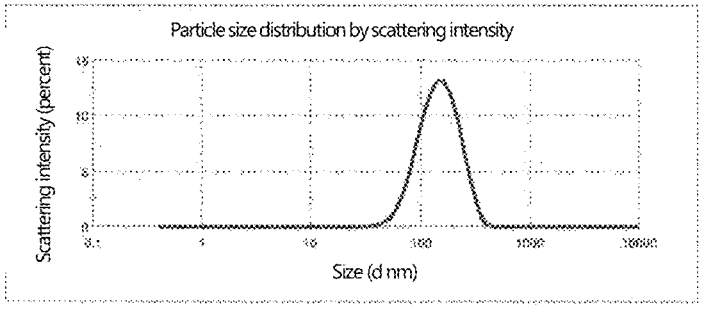
FIG. 8 is a diagram showing the average particle size distribution of Formulation 20.

As a result, Liposomal Formulation 20 having the properties shown in Table 9 below was obtained. FIG. 8 is a diagram showing the average particle size distribution of this formulation.

TABLE 9

| | | Average particle size (Z-Ave. nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formulation 20 | Mixing ratio of 2/10 | 135 | 0.136 | −30 | 11.30 | 0.06 | 0.005 | 0.5 |

\* Content = calculated from the concentration of compound (A) per mg of lipid.
\* Physical property testing was performed after filtration through a 0.22 μm filter.

6. Method for Quantifying Compound (A)

1) Compound (A) (5 mg) was weighed and placed in a test tube, and a 0.1N sodium hydroxide solution (0.125 mL) was added. The resulting mixture was dissolved by vortexing.

2) Purified water (4.875 mL) was added thereto to thus prepare a compound (A) solution of 1 mg/mL.

3) A calibration curve was prepared by measuring the absorbance at wavelength of 265 nm with respect to 6 different compound (A) concentrations of 0.0 mg/mL to 0.50 mg/mL.

4) Compound (A) solutions of known concentrations (0.1 mg/mL, 0.2 mg/mL, and 0.4 mg/mL) were prepared, and sample concentrations were obtained from the calibration curve.

5) The compound (A) solutions of known concentrations (0.1 mg/mL, 0.2 mg/mL, and 0.4 mg/mL) were each added to blank liposome (lipid concentration: 4.7 mg/mL), and the compound (A) concentrations were measured.

6) The recovery rates were calculated from the measurement results of the known concentration solutions, and the measurement results of the known concentration solutions to which liposome was added.

Figure 9:
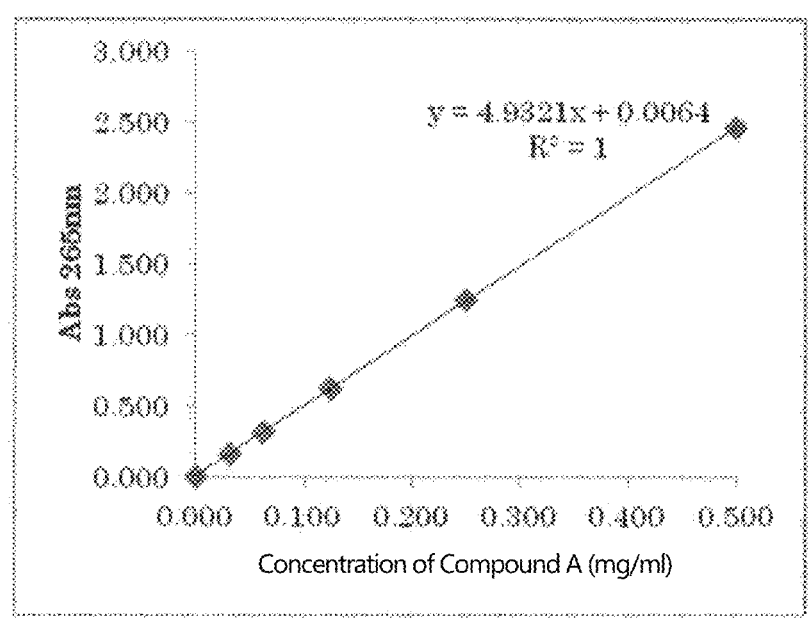
FIG. 9 is a graph showing the results of quantification of compound (A).

Table 10 and FIG. 9 show the measurement results.

TABLE 10

| Standard Curve Compound A (mg/mL) | Chloroform/methanol solution Absorbance 265 nm | | | |
|---|---|---|---|---|
| | ① | ② | ③ | Average |
| 0.000 | 0.129 | 0.130 | 0.127 | 0.000 |
| 0.031 | 0.293 | 0.291 | 0.291 | 0.163 |
| 0.063 | 0.435 | 0.450 | 0.450 | 0.316 |
| 0.125 | 0.736 | 0.761 | 0.761 | 0.624 |
| 0.250 | 1.360 | 1.374 | 1.381 | 1.243 |
| 0.500 | 2.567 | 2.587 | 2.642 | 2.470 |

| Slope | 4.9321 |
|---|---|
| Intercept | 0.0064 |

| | ① | ② | ③ | Average | Concentration (mg/ml) | Recovery rate (%) | Recovery rate (−Liposome) |
|---|---|---|---|---|---|---|---|
| Single drug: 0.1 mg/ml | 0.588 | 0.597 | 0.613 | 0.503 | 0.101 | 101 | |
| Single drug: 0.2 mg/ml | 0.966 | 0.925 | 0.998 | 0.867 | 0.174 | 87 | |
| Single drug: 0.4 mg/ml | 1.887 | 1.911 | 1.922 | 1.810 | 0.366 | 91 | |
| A) Liposome: 0.0 mg | 0.146 | 0.146 | 0.148 | 0.050 | 0.009 | | |
| A) Liposome: 0.1 mg | 0.591 | 0.600 | 0.604 | 0.502 | 0.200 | 100 | 91 |
| A) Liposome: 0.2 mg | 1.058 | 1.056 | 1.054 | 0.960 | 0.193 | 111 | 106 |
| A) Liposome: 0.4 mg | 1.881 | 1.922 | 1.936 | 1.817 | 0.367 | 100 | 98 |
| B) Liposome: 0.0 mg | 0.141 | 0.141 | 0.144 | 0.046 | 0.008 | | |
| B) Liposome: 0.1 mg | 0.580 | 0.591 | 0.581 | 0.488 | 0.098 | 97 | 89 |
| B) Liposome: 0.2 mg | 1.000 | 1.027 | 1.011 | 0.916 | 0.284 | 106 | 101 |
| B) Liposome: 0.4 mg | 1.845 | 1.866 | 1.889 | 1.770 | 0.358 | 98 | 98 |

The results confirmed that no effect was caused by the lipids formed into liposomes; thus, compound (A) was quantified by using an absorbance method.

7. Mass Production of Nanosphere of Stealth Liposome of Compound (A) by Bangham Method (1) A PEG-treated compound (A)-encapsulated liposome was prepared in large quantities by the Bangham method, and the properties were tested.

Production Method (i) HSPC (5.524 g), cholesterol (1.8419 g), and MPEG2000-DSPE (1.7978 g) were weighed and placed in an eggplant flask, a chloroform/methanol (1/1, v/v) solution was added so that the lipid concentration was 30 mg/mL, and the mixture was dissolved by stirring at 37° C.

(ii) The solvent was distilled off with an evaporator in a nitrogen atmosphere, followed by vacuum-drying. Fifteen 100-ml eggplant flasks each containing 600 mg of the lipids and one 100-ml eggplant flask containing 300 mg of the lipids were thus prepared.

(iii) Compound (A) was weighed, and a 0.1N sodium hydroxide solution was added thereto to produce a solution having a compound (A) concentration of 40 mg/mL. 10 mM phosphate buffer (pH: 8.0) was added to the solution so that the compound (A) concentration was 24 mg/mL.

(iv) The solution obtained in (iii) was added to the lipid film; and 10 mM phosphate buffer (pH: 8.0) was added thereto so that the lipid concentration was 10 mg/mL, followed by stirring at 37° C. for 1 hour. Then, 22.2 mg of compound (A) was added to the eggplant flasks each containing 600 mg of the lipids, and 11.1 mg of compound (A) was added to the flask containing 300 mg of the lipids.

(V) Ultrasonic treatment was performed for each of the eggplant flasks for 60 minutes in total using a VS-100III produced by AS ONE Corporation by repeating a cycle of 28 kHz output for 60 seconds, 45 kHz output for 60 seconds, and 100 kHz output for 3 seconds.

(vi) A stirred cell (8000 series, a 400-mL cell): Model 8400 5124 produced by Merck & Co., Inc., and BioMax PBMK 07610 produced by Merck & Co., Inc. were used. Since the solution amount was 930 mL in total, three cells were used for ultrafiltration (cutoff molecular weight: 300,000 Da) to replace the outer aqueous phase with 10 mM phosphate buffer (pH 7.4), and unencapsulated compound (A) was removed.

Figure 10:
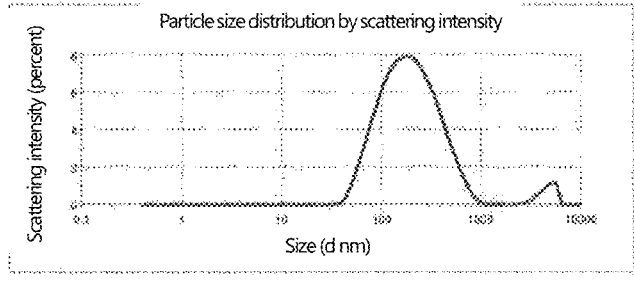
FIG. 10 is a diagram showing the average particle size distribution of Formulation 21.

As a result, a liposomal formulation having the properties shown in Table 11 below was obtained. FIG. 10 is a diagram showing the average particle size distribution of this formulation.

The following general test was conducted using part of the produced PEG-treated compound (A)-encapsulated liposome.

(2) FIG. 11 is transmission electron microscope images of Formulation 21.

Analysis method: Morphological observation

Photographing device: Hitachi H-7600 at 100 kV

Sample Production Method

Dispersion: 400-mesh grid with carbon support membrane

Staining: Negative staining (phosphotungstic acid)

FIG. 11 shows electron micrographs.

(3) Part of the produced PEG-treated compound (A)-encapsulated liposome was subjected to HPLC analysis to confirm the presence or absence of decomposition products.

Analysis and quantification of compound (A) by HPLC

Apparatus: Agilent 1290 Infinity LC series

Column: Shiseido Capcell Pak C18 UG120, 5 μm, 4.6× 150 mm

Mobile phase: 1% acetic acid/$H_2O$: 1% acetic acid/acetonitrile=60:40

Flow rate: 1 ml/min

Detection wavelength: 265 nm

Column temperature: 25° C.

Sample Preparation Method

Sample 1: Compound (A) was dissolved in a 1M sodium hydroxide solution so that compound A was 1 mg/mL. The resulting product was allowed to stand at 40° C. overnight (oxide production sample).

Sample 2: Compound (A) was added to a 0.1N sodium hydroxide solution-10 mM phosphate buffer (pH: 8.0) (buffer for encapsulation) so that compound (A) was 0.5 mg/mL (control sample)

Sample 3: Sample 2 was subjected to two-fold dilution with physiological saline to prepare a solution of 0.25 mg/mL. The solution was allowed to stand at 37° C. overnight (compound control sample).

Sample 4: PEG-treated empty liposomes were diluted 10-fold with physiological saline. The resulting product was allowed to stand at 37° C. overnight, followed by ultrafiltration (lipid control sample).

Sample 5: The PEG-treated compound (A)-encapsulated liposome was diluted 10-fold with physiological saline. The resulting product was allowed to stand at 37° C. overnight, followed by ultrafiltration (liposome sample).

The above 5 samples were analyzed by HPLC to confirm the presence or absence of oxides of compound (A), and the presence or absence of oxides of compound (A) of the PEG-treated compound (A)-encapsulated liposome in an environment at a temperature of 37° C.

FIG. 12 charts of HPLC measurement of Samples 1 to 5.

8. Production of PEG-Treated Compound (B)-Encapsulated Stealth Liposome by Bangham Method

TABLE 11

| | | Average particle size (Z-Ave. nm) | PDI | Zeta potential (mV) | Lipid concentration (mg/mL) | Concentration of compound (A) (mg/mL) | Compound (A)/lipid (mg/mL) | Content (%) |
|---|---|---|---|---|---|---|---|---|
| Formulation 21 | Large-scale preparation | 163 | 0.265 | −58 | 72.2 | 2.03 | 0.028 | 2.8 |

* Content = calculated from the concentration of compound (A) per mg of lipid.
* Physical property testing was performed after filtration through a 0.22 μm filter.

(1) Production of Liposome (i) HSPC (36.0 mg), cholesterol (12.0 mg), and MPEG2000-DSPE (12.0 mg) were weighed and placed in an eggplant flask, a chloroform/methanol (1/1, v/v) solution was added so that the lipid concentration was 30 mg/mL, and the mixture was dissolved by stirring at 37° C.

(ii) The solvent was distilled off with an evaporator in a nitrogen atmosphere, followed by vacuum-drying.

(iii) Compound (B) was added to and dissolved in 10 mM phosphate buffer (pH: 8.0) so that compound (B) was 20 mg/mL.

(iv) The compound (B) solution was added to the lipid film to achieve 1/10 (drug/lipid, w/w %), and 10 mM phosphate buffer (pH: 8.0) was added so that the lipid concentration was 10 mg/mL (compound (B): 6.0 mg, the lipids: 60.0 mg).

(v) The resulting product was vortexed for about 20 seconds, followed by stirring at 37° C. for 1 hour.

(vi) Ultrasonic treatment was performed for 90 minutes in total using a VS-100III produced by AS ONE Corporation by repeating a cycle of 28 kHz output for 60 seconds, 45 kHz output for 60 seconds, and 100 kHz output for 3 seconds.

(vii) A stirred cell (8000 series, a 10-mL cell): Model 8010 5121 produced by Merck & Co., Inc., and BioMax PBMK 02510 produced by Merck & Co., Inc. were used. The amount was 6 mL at the time of start and 4 mL at the time of collection, and 1.5-fold concentration was performed. Since the drug encapsulation amount was low, ultrafiltration (cutoff molecular weight: 300,000 Da) was performed to replace the outer aqueous phase with 10 mM phosphate buffer (pH 7.4), and unencapsulated compound (B) was removed.

Figure 13:
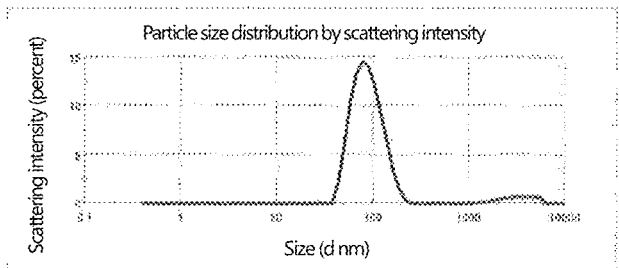
FIG. 13 is a diagram showing the average particle size distribution of Formulation 22.

As a result, a liposomal formulation having the properties shown in Table 12 below was obtained. FIG. 13 is a diagram showing the average particle size distribution of this formulation.

(iii) The sample of each concentration was diluted 10-fold with a chloroform/methanol (1/1, v/v) solution, and the absorption spectrum was measured at 220 to 700 nm using UV2700.

Figure 15:
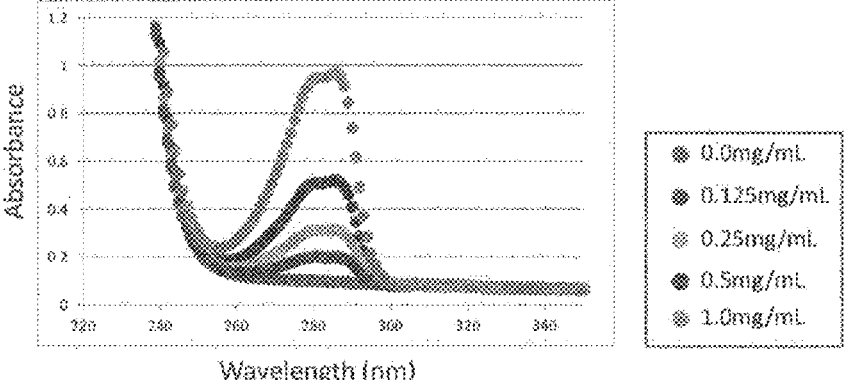
FIG. 15 is an absorption spectrum of a solution of compound (B).

The absorption spectrum of compound (B) was measured. As a result, the maximum absorption wavelength was 285 nm. It was confirmed that the quantification of compound (B) could be measured by the absorbance method (absorbance: 285 nm). FIG. 15 is a graph showing changes in the UV absorption spectrum.

9. Production of PEG-Treated Compound (C)-Encapsulated Stealth Liposome by Bangham Method (1) Liposome Production Method (i) HSPC (60.0 mg), cholesterol (12.0 mg), and MPEG2000-DSPE (12.0 mg) were weighed and placed in an eggplant flask, a chloroform/methanol (1/1, v/v) solution was added so that the lipid concentration was 30 mg/mL, and the mixture was dissolved by stirring at 37° C.

(ii) The solvent was distilled off with an evaporator in a nitrogen atmosphere, followed by vacuum-drying.

(iii) Compound (C) was dissolved in DMSO so that compound (C) was 20 mg/mL, and 10 mM phosphate buffer (pH: 8.0) was added so that compound (C) was 10 mg/mL.

(iv) The compound (C) solution was added to the lipid film to achieve 1/10 (drug/lipid, w/w %), and the mixture was stirred at 37° C. for 1 hour (compound (C): 6.0 mg, the lipids: 60.0 mg).

(v) Ultrasonic treatment was performed for 90 minutes in total using a VS-100III, produced by AS ONE Corporation by repeating a cycle of 28 kHz output for 60 seconds, 45 kHz output for 60 seconds, and 100 kHz output for 3 seconds.

TABLE 12

| | | Average particle size (Z-Ave. nm) | PDI | Zeta potential (mV) | Lipid concentration (mg/mL) | Concentration of compound (B) (mg/mL) | Compound (B)/lipid (mg/mL) | Content (%) |
|---|---|---|---|---|---|---|---|---|
| Formulation 22 | Mixing ratio of 1/10 | 87 | 0.199 | −32 | 12.19 | 0.101 | 0.008 | 0.8 |

\* Content = calculated from the concentration of compound (A) per mg of lipid.

\* Physical property testing was performed after filtration through a 0.22 μm filter.

Accordingly, a PEG-treated compound (B)-encapsulated liposome was produced.

Figure 14:
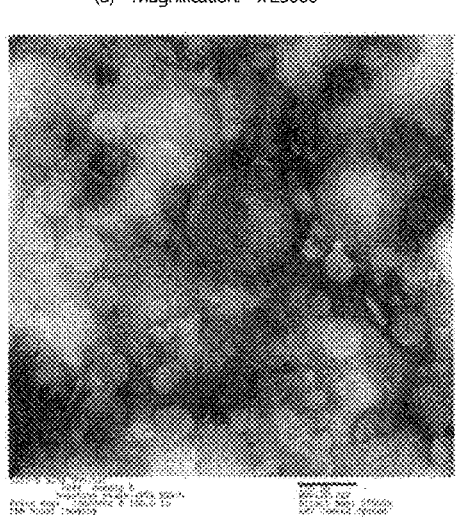
FIG. 14 is transmission electron microscope images of Formulation 22.

(2) FIG. 14 is transmission electron microscope images of Formulation 22.

(3) Analysis of Method of Quantifying Compound (B) Absorption Spectrum Confirmation Method (i) Compound (B) was added to and dissolved in 10 mM phosphate buffer (pH: 8.0) so that compound (B) was 20 mg/mL.

(ii) The product obtained in (i) was subjected to two-fold, four-serial dilutions with purified water.

(vi) Ultrafiltration (cutoff molecular weight: 300,000 Da) was performed using a stirred cell (8000 series, a 10-mL cell): Model 8010 5121 produced by Merck & Co., Inc., and BioMax PBMK 02510 produced by Merck & Co., Inc. to replace the outer aqueous phase with 10 mM phosphate buffer (pH 7.4), and unencapsulated compound (C) was removed.

Figure 16:
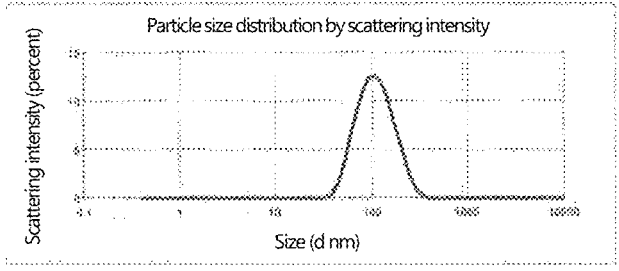
FIG. 16 is a diagram showing the average particle size distribution of Formulation 23.

(2) As a result, a liposome having the properties shown in Table 13 was obtained. FIG. 16 is a diagram showing the average particle size distribution.

TABLE 13

| | | Average particle size (Z-Ave. nm) | PDI | Zeta potential (mV) | Lipid concentration (mg/mL) | Concentration of compound (C) (mg/mL) | Compound (C)/lipid (mg/mL) | Content (%) |
|---|---|---|---|---|---|---|---|---|
| Formulation 23 | Mixing ratio of 1/10 | 97 | 0.158 | −34 | 17.27 | 1.02 | 0.059 | 5.9 |

\* Content = calculated from the concentration of compound (A) per mg of lipid
\* Physical property testing was performed after filtration through a 0.22 μm filter.

Accordingly, a PEG-treated compound (C)-encapsulated liposome was prepared.

Figure 17:
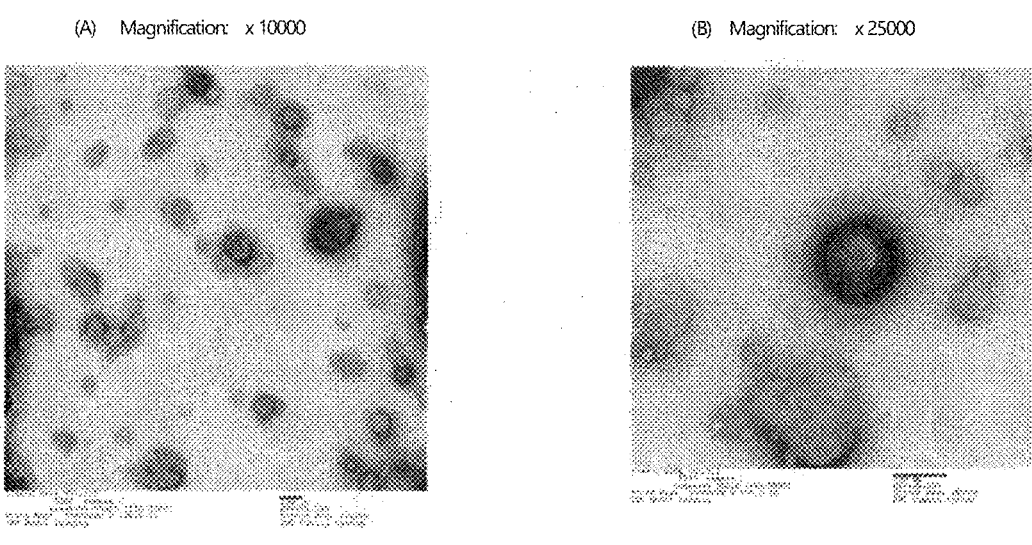
FIG. 17 is transmission electron microscope images of Formulation 23.

(3) FIG. 17 is transmission electron microscope images of Formulation 23.

(4) Analysis of Method of Quantifying Compound (C) Absorption Spectrum Confirmation Method (i) Compound (C) was added to and dissolved in DMSO so that compound (C) was 20 mg/mL.

(ii) An equivalent amount of 10 mM phosphate buffer (pH: 8.0) was added to the product obtained in (i) to produce a 50% DMSO solution having a compound (C) concentration of 10 mg/mL.

(iii) The product obtained in (ii) was subjected to two-fold, three-serial dilution with purified water.

(vi) The sample of each concentration was diluted 10-fold with a chloroform/methanol (1/1, v/v) solution, and the absorption spectrum was measured at 220 to 700 nm using UV2700.

Figure 18:
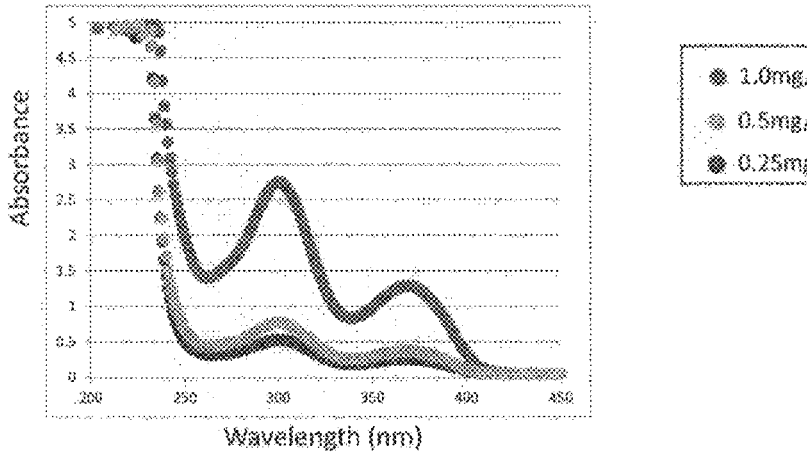
FIG. 18 is an absorption spectrum of compound (C).

The absorption spectrum of compound (C) was measured; the absorption peaks were detected at 300 nm and 368 nm. It was confirmed that the quantification of compound (C) could be performed by the absorbance method (wavelength: 300 nm). FIG. 18 is a graph showing changes in the UV absorption spectrum of compound (C).

10. Production of Stealth Liposomal Formulation of Compound (A) (ONO-1301) by Direct Dispersion Improving Method 1) Production Method (i) The two types of lipids and compound (A) were weighed as shown in Table 14 below, and dissolved in 20 g of t-butanol at 70° C.

TABLE 14

| Lipid or API | Composition 1 (Formulation 24) | Composition 2 (Formulation 25) |
|---|---|---|
| DEPC | 1.88 g | 1.80 g |
| MPEG2000-DSPE | 0.12 g | 0.20 g |
| Compound (A) | 100 mg | 100 mg |

(ii) The liquid obtained by dissolution in (i) was instantly frozen in dry ice/acetone.

(iii) After freezing, the resulting product was freeze-dried for about 17 hours with a freeze-dryer.

(iv) 440 mL of PBS(−) was added to the obtained powder, and the mixture was placed in a warm bath at 50° C. and dispersed by a sonicator until no lumps were present (at this time, the ONO-1301 concentration was 2.5 mg/mL).

(v) A polycarbonate filter with a pore size of 400 nm and a drain disc were attached, and sizing was performed at about 50 kg/cm² with an extruder in which the jacket was watered with warm water at 50° C.

(vi) In the same manner as (v), sizing was performed with a 200-nm filter (3 Pass) to thus obtain a translucent liposome solution.

2) Ultrafiltration

Ultrafiltration (ultrafiltration membrane: PBMK04310, Merck Millipore, cutoff molecular weight: 300,000 Da) was performed using PBS(−) (10-fold dilution of SIGMA D1408) to remove unencapsulated compounds.

Ultrafiltration was performed using a stirred cell, 8000 series: Model 8050, product No. 5122, produced by Merck & Co., Inc. For the membrane, BioMax PBMK 04310,300 kDa, produced by Merck & Co., Inc., was used.

After the filtration, sterilization and filtration with a 0.22-μm filter was performed in a clean bench.

3) Confirmation of Properties

The liposome solution was subjected to ultrafiltration (cutoff molecular weight: 300,000 Da) with PBS(−): Dulbecco's phosphate buffered saline (without Ca and Mg), and the resulting product was used as a sample after ultrafiltration. Additionally, the presence or absence of oxides of ONO-1301 was confirmed by HPLC.

As shown in Table 15, the results showed no significant change in each physical property before and after the ultrafiltration. Additionally, as shown in FIGS. 19 and 20, no peaks of ONO-1301 decomposition products were observed in the particle size distribution or the HPLC analysis results. The yield of compound (A) was 88%.

4) Stability Test

After ultrafiltration (Formulation 25), the stability was analyzed after storage at 4° C. for 9 months using PBS(−): Dulbecco's phosphate buffered saline (without Ca and Mg); the results confirmed no change in the particle size distribution, content, and other physical properties; thus, the formulation was confirmed to be stable.

TABLE 15

| | | Average particle size (Z-Ave. nm) | PDI | Zeta potential (mV) | Lipid concentration (mg/mL) | Compound of the invention (mg/mL) | Compound of the invention/ lipid (mg/mL) | Content (%) |
|---|---|---|---|---|---|---|---|---|
| Formulation 24 | Before ultrafiltration | 91.4 | 0.16 | −3.4 | 41.8 | 2.5 | 0.060 | 6.0 |

TABLE 15-continued

| | | Average particle size (Z-Ave. nm) | PDI | Zeta potential (mV) | Lipid concentration (mg/mL) | Compound of the invention (mg/mL) | Compound of the invention/ lipid (mg/mL) | Content (%) |
|---|---|---|---|---|---|---|---|---|
| Formulation 25 | After ultrafiltration | 86.8 | 0.14 | −2.1 | 40.1 | 2.2 | 0.055 | 5.5 |

5) Confirmation of Decomposition Product (HPLC Analysis)

The HPLC measurement results confirmed that no decomposition products of compound (A) were present under the conditions of this production.

11. Production of Stealth Liposomal Formulations of Compound (B), Compound (D), and Compound (E) by Direct Dispersion Improving Method Liposome Production Method (i) DEPC (Nippon Fine Chemical Co., Ltd.) (0.188 g) and MPEG2000-DSPE (Nippon Fine Chemical Co., Ltd.) (0.012 g), and compound (B, D, or E) (0.01 g) were weighed and placed in a glass vial.

(ii) 2.0 g of t-butanol was added to the product obtained in (i), and the mixture was dissolved by stirring while heating at 37° C.

(iii) The resulting product was instantly frozen in ethanol-dry ice.

(iv) Freeze-drying was performed for 17 hours.

(v) PBS(−) (Dulbecco's phosphate buffered saline (without Ca and Mg)) (20 mL) was added to the lipid/compound powder obtained after freeze-drying.

(vi) After the resulting product was vortexed lightly, ultrasonic treatment was performed for 30 minutes while heating at 37° C.

(vii) Extruder treatment was performed while heating at 37° C. For the apparatus, a LIPEX extruder (100 mL) was used. After treatment was performed once with a polycarbonate filter with a pore size of 400 nm, treatment was performed three times with a polycarbonate filter with a pore size of 200 nm (treatment pressure: about 5 MPa). The extruder used was a Lipex Thermobarrel Extruder (100 mL) produced by Northern Lipids, and the membranes used were Nuclepore membranes produced by GE Healthcare (400 nm: Product No. 111107; 200 nm: Product No. 111106).

(viii) Ultrafiltration (ultrafiltration membrane: PBMK04310, Merck Millipore, cutoff molecular weight: 300,000 Da) was performed using PBS(−) (10-fold dilution of SIGMA D1408), and unencapsulated compounds were removed. The ultrafiltration was performed until the ultrafiltration waste liquid became 140 mL, which was 7 times the liposome amount (20 mL); and the resulting product in the final amount of 20 mL was collected.

The ultrafiltration was performed using a stirred cell, 8000 series: Model 8050, product No. 5122, produced by Merck & Co., Inc. For the membrane, BioMax PBMK 04310, 300 kDa, produced by Merck & Co., Inc., was used. The liposome solution was introduced into the stirred cell, the apparatus was set, and feeding of the solution was performed by nitrogen gas pressurization (0.4 MPa) until 140 mL of waste liquid was discharged.

(ix) Sterilization and filtration were performed with a 0.22-μm filter in a clean bench.

(x) A physical property test was performed. In the physical property test, the average particle size measurement, zeta potential measurement, lipid quantification (Wako Pure Chemical Industries, Phospholipid C-Test Wako), and absorbance measurement (Abs 680 nm) were performed.

Figure 21:
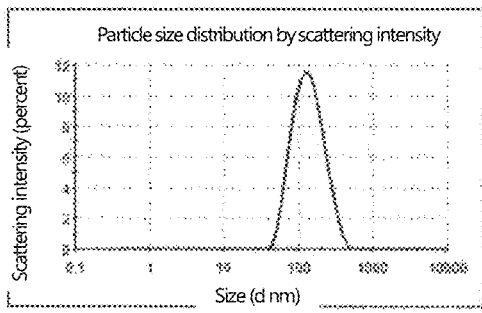
FIG. 21 shows the particle size distribution of liposomes having compound (B) encapsulated therein (Formulation 26).
Figure 22:
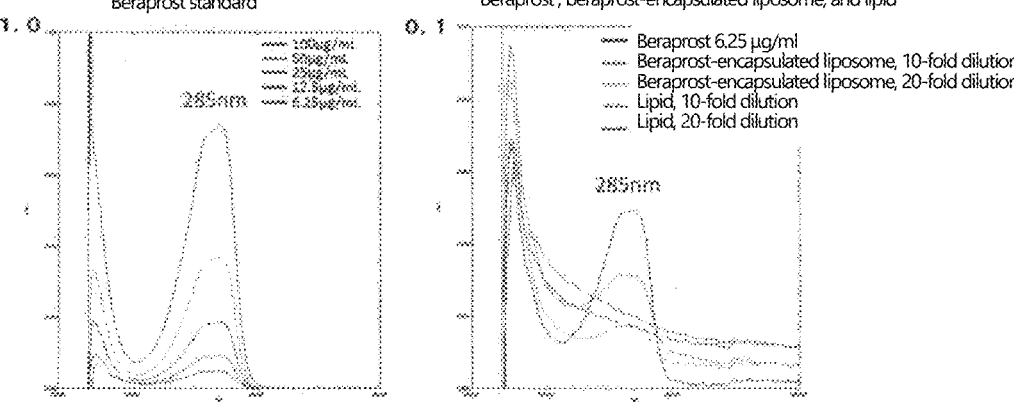
FIG. 22 shows UV absorption spectra of compound (B), and liposomes having compound (B) encapsulated therein.

Test Results (1) Production of Compound (B) (Formulation 26)-Encapsulated Liposome The compound (B)-encapsulated liposome had the physical properties shown in Table 16 and FIG. 21. As shown in FIG. 22, UV absorption derived from compound (B) was observed in the UV absorption spectrum of the compound (B)-encapsulated liposome. Table 16 below shows the properties (the particle size, PdI value, and zeta potential) of the obtained liposome. FIG. 21 shows the liposome particle size distribution of Formulation 26.

FIG. 22 shows UV absorption spectra of compound (B) (Beriplast) and liposomes containing the compound (B).

TABLE 16

| Lipid (mg/mL) | Encapsulated amount (mg/mL) | Average particle size (nm) | PdI | Zeta potential (mV) |
|---|---|---|---|---|
| 6.2 | 0.017 or less | 122 | 0.190 | −19 |

(2) Production of Compound (D) (Formulation 27)-Encapsulated Stealth Liposome

Figure 23:
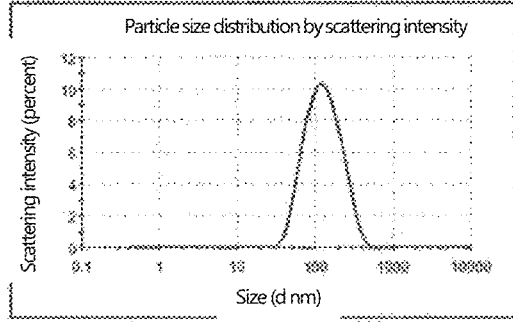
FIG. 23 shows the particle size distribution of liposomes having compound (D) encapsulated therein (Formulation 27).

The amount of encapsulated compound (D) was 0.249 mg/mL according to UV quantification. The obtained liposome had the properties shown in Table 17 below, i.e., the particle size, PdI value, and zeta potential. FIG. 23 shows the liposome particle size distribution of Formulation 27.

Figure 24:
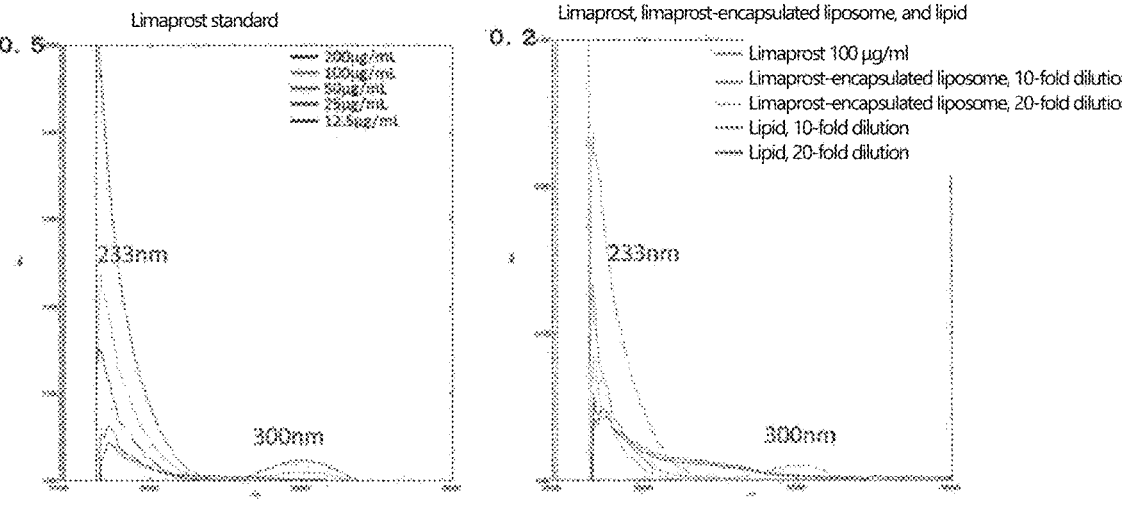
FIG. 24 is UV absorption spectra of compound (D), and liposomes having compound (D) encapsulated therein (Formulation 27).

The absorption spectrum of FIG. 24 shows quantitativity at UV absorption of 233 nm. FIG. 24 is UV absorption spectra of compound (D) (Limaprost) and liposomes containing Limaprost.

TABLE 17

| Formulation 27: | | | | |
|---|---|---|---|---|
| Lipid (mg/mL) | Encapsulated amount (mg/mL) | Average particle size (nm) | PdI | Zeta potential (mV) |
| 6.0 | 0.249 | 110 | 0.200 | −19 |

(3) Production of Compound (E) (Formulation 28)-Encapsulated Stealth Liposome

Figure 25:
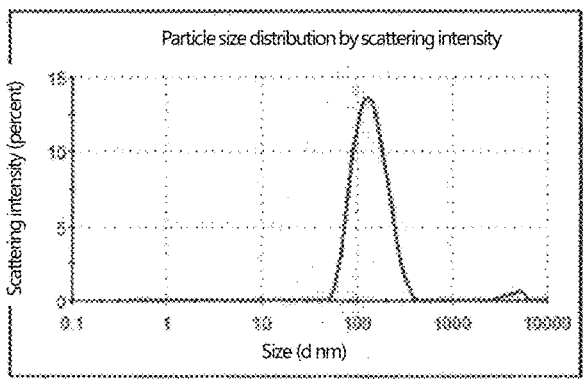
FIG. 25 is a diagram showing the average particle size distribution of liposomes having compound (E) encapsulated therein (Formulation 28).
Figure 26:
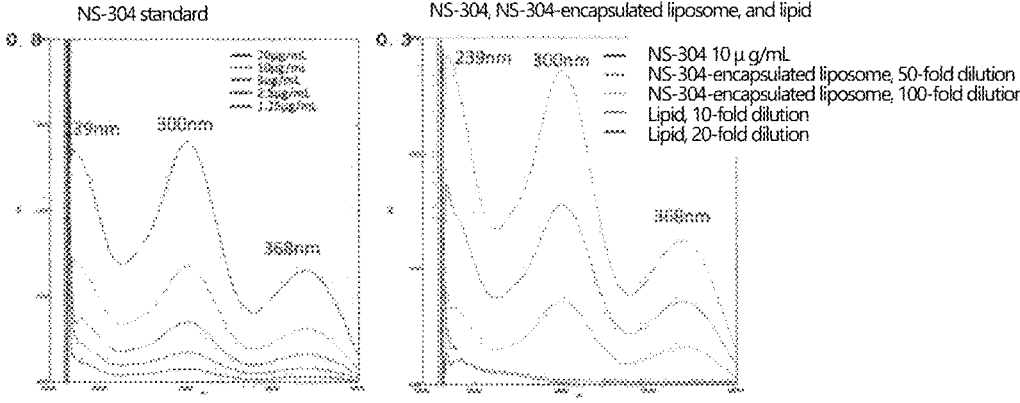
FIG. 26 is absorption spectra of compound (E) and liposomes having compound (E) encapsulated therein (Formulation 28).

A compound (E)-encapsulated liposome had the physical properties shown in Table 18 and FIG. 25. The amount of encapsulated compound (E) was 0.305 mg/mL according to UV quantification. The table below shows the particle size, PdI value, and zeta potential. The absorption spectra of FIG. 26 shows quantitativity at UV absorption of 300 nm.

TABLE 18

| Formulation 28: | | | | |
| --- | --- | --- | --- | --- |
| Lipid (mg/mL) | Encapsulated amount (mg/mL) | Average particle size (nm) | PdI | Zeta potential (mV) |
| 5.9 | 0.305 | 131 | 0.171 | −36 |

11. Various Pharmacodynamic and Pharmacological Tests using Compound (A) Stealth Liposomes of Formulations 21 and 25

1) Analysis of Effect of Intermittent Intravenous Administration of Formulation 21 (ONO-1301Lipo) on Rat Monocrotaline-Induced Pulmonary Hypertension Model The produced Formulation 21 (ONO-1301Lipo formulation) as a test substance was intermittently administered intravenously once weekly to a rat monocrotaline (MCT)-induced severe heart failure (pulmonary hypertension) model from day 7 of the MCT administration, and the survival rate was compared with a group in which compound (A) (ONO-1301) was repeatedly orally administered; a group in which compound (A) was intermittently administered intravenously once weekly; and, as a positive control, a group in which an ET-1 antagonist (bosentan) was orally administered. In the control group, physiological saline (vehicle) was administered once weekly by intravenous administration.

For animals, Slc: Wistar male rats, 5 weeks old at the start of the test, and 66.4 to 90.8 g at arrival (Japan SLC, Inc.) were used. Monocrotaline (hereinafter referred to as "MCT"), lot No.: SLBG1999V (Sigma-Aldrich Corporation), was administered once subcutaneously at the back of the rats at a dose of 60 mg/kg. Six days after the MCT administration, the animals were divided into groups according to the weight stratification assignment method (Table 19).

TABLE 19

| Group | Administered substance/ dose/frequency of administration | Route of administration | Number of cases |
| --- | --- | --- | --- |
| 1 | Physiological saline/week | Intravenous injection | 20 |
| 2 | Compound (A) (ONO-1301), 3 mg/kg × twice/day | Oral administration | 10 |
| 3 | Bosentan, 50 mg/kg × twice/day | Oral administration | 10 |
| 4 | Formulation 21.1 mg/kg/week* | Intravenous injection | 10 |
| 5 | Compound (A) (ONO-1301), 1 mg/kg/week | Intravenous injection | 10 |

*The dose is in terms of compound (A) (ONO-1301).

Figure 27:
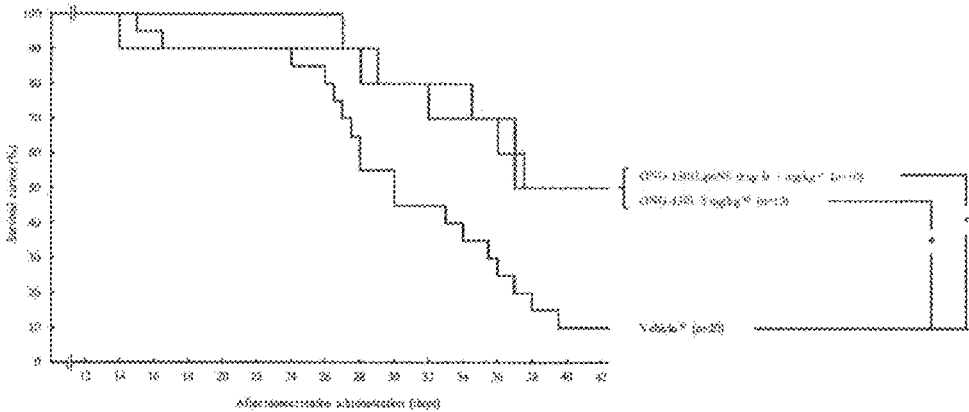
FIG. 27 shows 42-day survival curves of a group receiving ONO-1301 by repeated oral administration, and a group receiving Formulation 21 (ONO-1301LipoNS formulation) by intermittent intravenous administration.

FIG. 27 shows changes in the survival rates of Group 1, Group 2, and Group 4 until 42 days after the preparation of the severe heart failure model. Table 20 shows the survival rates of all of the groups after 42 days.

In Group 1, one death was observed 15 days after the preparation of the severe heart failure model by subcutaneous administration of MCT at 60 mg/kg. Thereafter, 17 deaths were observed by day 42, and the final survival rate was 10% (number of animals alive: 2/20).

In the group in which compound (A) was repeatedly orally administered at 3 mg/kg twice daily (Group 2), one death was observed 14 days after the preparation of the severe heart failure model. Thereafter, 4 more deaths were observed by day 42, and the final survival rate was 50%

(number of animals alive: 5/10), showing a significant life-prolonging effect compared with the control group (Group 1) ($p < 0.05$).

In the group in which bosentan was repeatedly orally administered at 50 mg/kg twice daily (Group 3), one death was observed 20 days after the preparation of the severe heart failure model. Thereafter, another 6 deaths were observed by day 42, and the final survival rate was 30% (number of animals alive: 3/10), showing no significant life-prolonging effect compared with the control group (Group 1).

Bosentan, which is an ET-1 antagonist, used in the positive control, has been clinically used as a therapeutic agent for pulmonary hypertension, and the efficacy thereof has been confirmed in the same rat MCT-induced heart failure model (Circ. J. 2013; 77:2127-2133). However, these results are based on repeated oral administration immediately after the MCT administration. This time, a significant life-prolonging effect could not be observed in the administration started 7 days after the MCT administration (Group 3).

In the group in which Formulation 21 (ONO-1301Lipo) was intermittently administered intravenously at 1 mg/kg once weekly (Group 4), one death was observed 27 days after the preparation of the severe heart failure model. Thereafter, 4 deaths were observed by day 42, and the final survival rate was 50% (number of animals alive: 5/10), showing a significant life-prolonging effect compared with the control group (Group 1) ($p < 0.05$).

In the group in which compound (A) was intermittently administered intravenously at 1 mg/kg once weekly (Group 6), two deaths were observed about 30 minutes after the administration 28 days after the preparation of the severe heart failure model. Thereafter, 6 deaths were observed by day 42, and the final survival rate was 20% (number of animals alive: 2/10), showing no significant life-prolonging effect compared with the control group (Group 1).

TABLE 20

| Group | Administered substance, dose, frequency of administration | Route of administration | Number of cases | Survival rate (%) |
| --- | --- | --- | --- | --- |
| 1 | Physiological saline | Intravenous injection | 20 | 10 |
| 2 | Compound (A) (ONO-1301); 3 mg/kg × twice/day | Oral administration | 10 | 50* |
| 3 | Bosentan; 50 mg/kg × twice/day | Oral administration | 10 | 30 |
| 4 | Formulation 21; 1 mg/kg/week | Intravenous injection | 10 | 50* |
| 5 | Compound (A) (ONO-1301); 1 mg/kg/week | Intravenous injection | 10 | 20 |

The total test substance amount of compound (A) administered from 7 days to 41 days after the MCT administration (35 days in total) was calculated per animal.

As a result, the amount was 210 mg/kg/animal (3 mg/kg× twice/day×35 days) in Group 2, 3500 mg/kg/animal (50 mg/kg×twice/day×35 days) in Group 3, and 5 mg/kg/animal (1 mg/kg/week×5 times) in Group 4 and Group 5. Group 4 showed an effect similar to that of Group 2 at a 5/210 (1/42) dose amount of Group 2.

As a disease site-specific DDS liposomal formulation, a novel ONO-1301 liposomal formulation (Formulation 21; ONO-1301Lipo) was produced to analyze the development of a therapeutic method for developing a more versatile, disease site-specific (DDS) therapeutic agent for a severe heart failure, by intermittent intravenous administration.

The DDS effect was confirmed by comparing the survival rates in the MCT-induced severe heart failure model by the intermittent intravenous administration of Formulation 21.

Bosentan, which is an ET-1 antagonist, and used as the positive control substance, has been clinically used as a therapeutic agent for pulmonary hypertension; and the efficacy thereof has been confirmed in the MCT-induced heart failure model. However, these results are based on repeated oral administration immediately after the MCT administration. This time, a significant life-prolonging effect could not be observed in the administration treatment 7 days after the MCT administration. In contrast, the final survival rate of the group in which compound (A) was repeatedly administered at 3 mg/kg twice daily (Group 2) was 50%, which showed a significant life-prolonging effect compared with the control group (Group 1). Additionally, the final survival rate of the group in which Formulation 21 (ONO-1301Lipo) was intermittently administered intravenously at 1 mg/kg once weekly (Group 4) was 50%, which also showed a life-prolonging effect comparable with Compound (A) (Group 2).

The group in which Formulation 21 was intermittently administered intravenously at 1 mg/kg/week (Group 4) showed a life-prolonging effect similar to that of the group in which compound (A) was repeatedly orally administered at 3 mg/kg twice daily (Group 2), with the total dose amount of Group 4 being 1/42 of that of Group 2; thus, Group 4 was confirmed to exhibit a DDS effect as a liposomal formulation.

In contrast, the group in which the ONO-1301 drug substance was intermittently administered intravenously at 1 mg/kg/week (Group 5) showed no effect (Table 20).

The above results revealed that the repeated oral administration of compound (A) (ONO-1301) and the intermittent intravenous administration of Formulation 21 showed a significant life-prolonging effect by therapeutic administration to the severe heart failure model after the onset of heart failure (7 days after the MCT administration). Further, a similar life-prolonging effect was exhibited at a total dose amount of 1/42, showing a DDS effect as a stealth liposomal formulation.

2) Analysis of DDS Effect of Formulation 25 (ONO-1301Lipo) on BLM Pulmonary Fibrosis Model Mice by Various Administration Methods 1. Method C57BL/6NCr female mice (7 weeks old) were anesthetized with sodium pentobarbital, and then intratracheally (intrapulmonary) administered with 20 μL of a bleomycin hydrochloride aqueous solution (BLM) twice (40 μL in total per animal). In a normal group (Normal), vehicle (physiological saline) was similarly intratracheally administered.

From 6 days to 28 days after the BLM administration, the test substance was administered to compare the survival rates. As the test substances, compound (A) (ONO-1301) was repeatedly orally administration twice daily, compound (A) (ONO-1301) was intravenously administered once weekly, and compound (A) (ONO-1301) was intratracheally administered once weekly. Further, Formulation 25 (ONO-1301Lipo) was intravenously administered once weekly, and Formulation 25 (ONO-1301Lipo) was intratracheally administered once weekly to analyze the DDS effect of Formulation 25 (ONO-1301Lipo) by comparing the survival rates.

2. Table 21 shows the test group constitution.

TABLE 21

| Group | Test group | Dose | Route of administration | Number of animals |
|---|---|---|---|---|
| 1 | Control (vehicle) | 0.5% CMC-Na aqueous solution × twice/day | Oral administration | 10 |
| 2 | Compound (A) (ONO-1301) | 3 mg/kg × twice/day | Oral administration | 10 |
| 3 | Compound (A) (ONO-1301) | 3 mg/kg × once/week | Intravenous administration | 10 |
| 4 | Formulation 25 (ONO-1301LipoNS) | 1 mg/kg × once/week* | Intravenous administration | 10 |
| 5 | Formulation 25 (ONO-1301LipoNS) | 3 mg/kg × once/week* | Intravenous administration | 10 |
| 6 | Compound (A) (ONO-1301) | 1 mg/kg × once/week | Intratracheal administration | 10 |
| 7 | Formulation 25 (ONO-1301LipoNS) | 0.3 mg/kg × once/week* | Intratracheal administration | 10 |
| 8 | Formulation 25 (ONO-1301LipoNS) | 1 mg/kg × once/week* | Intratracheal administration | 10 |
| 9 | Normal | Physiological saline × once/week | Intratracheal administration | 5 |

*The dose is in terms of compound (A) (ONO-1301).

3. Test Substance Administration

1) Oral administration: Administration of vehicle (0.5% CMC-Na aqueous solution) and compound (A) (Groups 1 and 2)

From 6 days after the preparation of the lung injury model, the vehicle and compound (A) (3 mg/kg) were repeatedly orally administered twice daily for 23 days (the administration interval between morning and afternoon was 8 hours or more).

Dose amount: 5 mL/kg×twice/day

Administration method: Gavage oral administration using a disposable polypropylene syringe and a mouse stomach tube 2) Intravenous administration: Administration of compound (A) and Formulation 25 (Groups 3, 4, and 5)

The administration was performed 6 days after the preparation of the lung injury model; after that, tail vein intravenous administration was performed once weekly (4 times in total, i.e., 6, 13, 20, and 27 or 28 days after the preparation of the model).

Dose amount: 1.5 ml/kg

Administration method: Intravenous administration using a glass syringe and a disposable injection needle 30G 3) Intratracheal administration: Administration of compound (A) and Formulation 25 (Groups 6, 7, 8, and 9)

The administration was performed 6 days after the preparation of the lung injury model; after that, intratracheal administration was performed once weekly (4 times in total, i.e., 6, 13, 20, and 27 or 28 days after the preparation of the model). In normal Group 9 (Normal), physiological saline was administered in a similar manner.

Dose amount: 0.5 ml/kg

Administration method: After anesthesia with pentobarbital (30 to 35 mg/kg, i.p.), intratracheal (intrapulmonary) administration was performed.

4. Results

Figure 28:
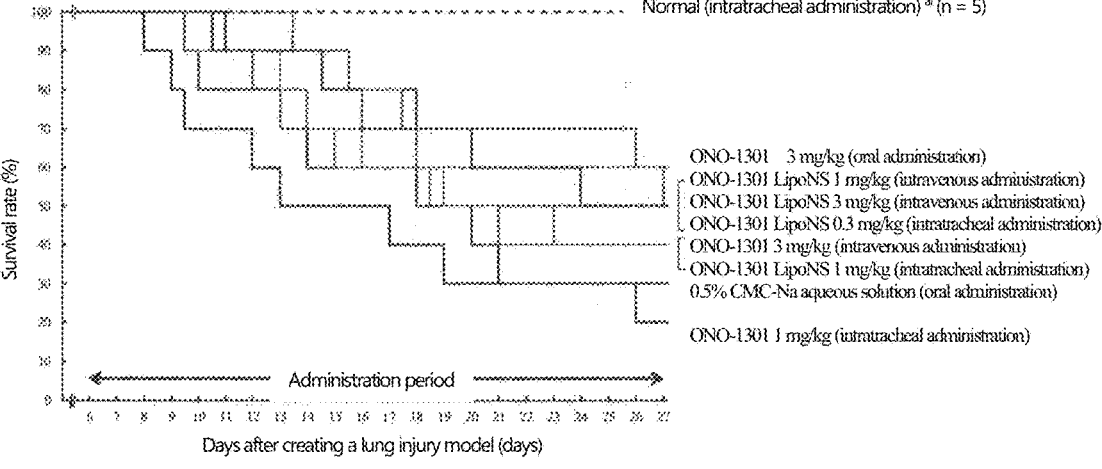
FIG. 28 is a graph showing the survival rates of all groups.
Figure 29:
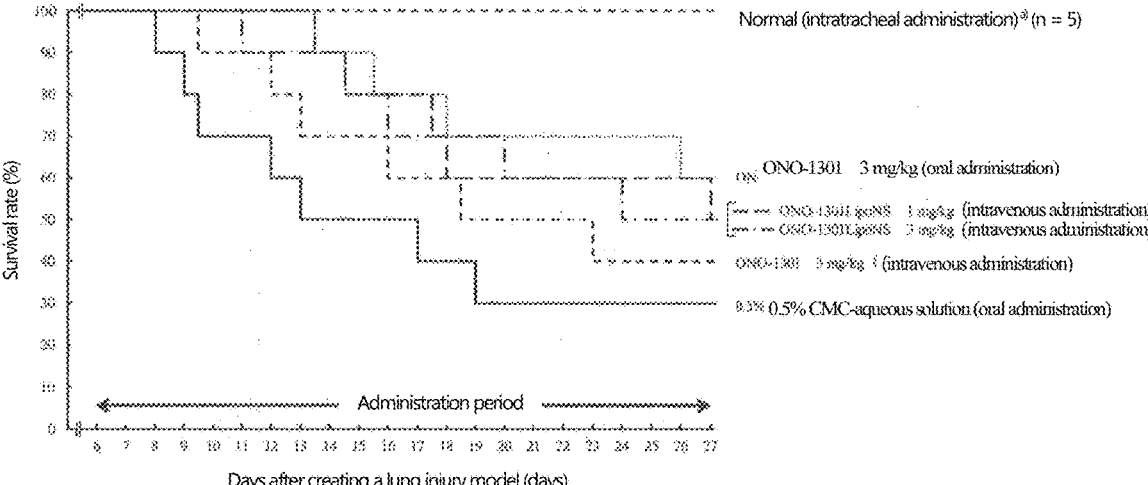
FIG. 29 is a graph showing a comparison with intermittent intravenous administration of Formulation 25 (ONO-1301Lipo).

1) FIGS. 28 to 30 show the results of the survival rates.

In the normal group, no deaths were observed. In contrast, the group in which the vehicle was orally administered to the lung injury model showed a survival rate of 30%. The group in which compound (A) was orally administered at 3 mg/kg showed a survival rate of 60%, thus achieving a life-prolonging effect compared with the vehicle administration group. The group in which compound (A) was intravenously administered at 3 mg/kg showed a survival rate of 40%. The groups in which Formulation 25 was intravenously administered at 1 mg/kg or 3 mg/kg both showed a survival rate of 50%. The group in which compound (A) was intratracheally administered at 1 mg/kg showed a survival rate of 20%. The groups in which Formulation 25 was intratracheally administered at 0.3 mg/kg and 1 mg/kg respectively showed survival rates of 50% and 40%, which are higher than that of the vehicle administration group or the group in which compound (A) was intratracheal administered at 1 mg/kg.

2) Comparison of Survival Rates (1) FIG. 29: Comparison with intermittent intravenous administration of Formulation 25 (ONO-1301Lipo)

In Group 2, the total dose amount of compound (A) (ONO-1301) (3 mg/kg×twice×22 days) was 132 mg/kg.

Further, the total dose amount of intravenous administration of compound (A) (ONO-1301) at 3 mg/kg once weekly (Group 3) was 12 mg/kg, and the total dose amount of intravenous administration of Formulation 25 at 1 mg/kg once weekly (Group 4) was 4 mg/kg. The total dose amount of intravenous administration of Formulations 25 at 3 mg/kg once weekly (Group 5) was 12 mg/kg.

The survival rate in the vehicle group (Group 1) was 30%. In comparison with the group in which compound (A) (ONO-1301) was orally administered (Group 2: 60%), the survival rates of Group 4 (dose amount: $1/33$ of the total dose amount of Group 2) and Group 5 (dose amount: $1/11$ of the total dose amount of Group 2) were slightly lower than that of Group 2, and both showed the same value (50%). In contrast, the group in which the compound (A) (ONO-1301) drug substance was intravenously administered at 3 mg/kg once weekly (Group 5) showed an even lower survival rate (40%) at a dose amount $1/11$ that of Group 2.

These results revealed that the intravenous administration of Formulation 25 once weekly (Groups 4 and 5) to the lung injury model showed a prolonging effect on the survival rate, compared with intravenous administration of the compound (A) (ONO-1301) drug substance once weekly (Group 3). Further, Groups 4 and 5 showed a slightly lower survival rate than that of the group in which the compound (A) (ONO-1301) drug substance was repeatedly orally administered twice daily (Group 2), although the total dose amounts of Groups 4 and 5 were as low as $1/11$ to $1/33$ that of Group 2. These results suggested that the intravenous administration of Formulation 25 exhibited a DDS effect specific to the lung disease site.

(2) FIG. 30: Comparison with intermittent intratracheal administration of Formulation 25 (ONO-1301Lipo)

In Group 2, the total dose amount of compound (A) (ONO-1301) (3 mg/kg×twice×22 days) was 132 mg/kg.

The total dose amount of intratracheal administration of compound (A) (ONO-1301) at 1 mg/kg once weekly (Group 6) was 4 mg/kg, and the total dose amount of intratracheal administration of Formulation 25 at 0.3 mg/kg once weekly (Group 7) was 1.2 mg/kg. The total dose amount of intratracheal administration of Formulation 25 at 1 mg/kg once weekly (Group 8) was 4 mg/kg.

The survival rate in the vehicle administration group (Group 1) was 30%. In comparison with the group in which compound (A) (ONO-1301) was orally administered (Group 2: 60%), Group 7 (dose amount: 1/110 of the total dose amount of Group 2) and Group 8 (dose amount: 1/33 of the total dose of Group 2) showed survival rates of 50% and 40%, respectively.

In contrast, the group in which the compound (A) (ONO-1301) drug substance was intravenously administered at 1 mg/kg once weekly (Group 6) showed an even lower survival rate (20%) at a dose amount of $1/33$ that of Group 2.

These results revealed that intratracheal administration of Formulation 25 once weekly (Group 7 and Group 8) to the lung injury model showed a prolonging effect on the survival rate, compared with the intratracheal administration of the compound (A) (ONO-1301) drug substance once weekly (Group 6). Further, Group 7 and Group 8 showed a slightly lower survival rate than that of the group of repeated oral administration of the compound (A) (ONO-1301) drug substance twice daily (Group 2), although the total dose amounts of Group 7 and Group 8 were as low as $1/110$ to $1/33$ that of Group 2. These results suggested that the intratracheal administration of Formulation 25 exhibited a DDS effect specific to the lung disease site. Further, intratracheal administration of Formulation 25 at 0.3 mg/kg once weekly showed the same survival rate (50%) as those of the intravenous administration of Formulation 25 at 1 mg/kg or 3 mg/kg once weekly. This suggested that intratracheal administration exhibits a DDS effect greater than that of the intravenous administration.

Based on the above results, the survival rates of the groups in which Formulation 25 was intermittently administered intravenously once weekly (Groups 4 and 5) and the groups in which Formulation 25 was intermittently administered intratracheally once weekly (Groups 7 and 8) were compared with that of the vehicle administration group (Group 1), using the bleomycin-induced lung injury model mice from day 6 of the bleomycin administration. As a positive control, a group in which compound (A) (ONO-1301) was repeatedly orally administered twice daily (Group 2) was created. Further, a group in which compound (A) (ONO-1301) was intermittently administered intravenously once weekly (Group 3) and a group in which compound (A) (ONO-1301) was intermittently administered intratracheally (Group 6) were created to compare the DDS effect as ONO-1301 liposomal formulations.

In the test, the group in which compound (A) (ONO-1301) was repeatedly orally administered at 3 mg/kg twice daily from day 6 of the bleomycin administration showed a prolonged survival rate, suggesting a therapeutic effect.

The intravenous administration of Formulation 25 once weekly (Groups 4 and 5) showed a prolonging effect on the survival rate, compared with intravenous administration of the compound (A) (ONO-1301) drug substance once weekly (Group 3). Further, Groups 4 and 5 showed a slightly lower survival rate than that of the group of repeated oral administration of the compound (A) (ONO-1301) drug substance twice daily (Group 2), although the total dose amounts of Groups 4 and 5 were as low as $1/11$ to $1/33$ that of Group 2. These results suggested that intravenous administration of Formulation 25 showed a DDS effect specific to the lung disease site.

The group in which Formulation 25 was intratracheally administered once weekly (Groups 7 and 8) showed a prolonging effect on the survival rate, compared with the group in which the compound (A) (ONO-1301) drug substance was intratracheally administered once weekly (Group 6). Further, Groups 7 and 8 showed a slightly lower survival rate than that of the group in which the compound (A) (ONO-1301) drug substance was repeatedly orally administered twice daily (Group 2), although the total dose amount was as low as $1/110$ to $1/33$ that of Group 2. These results suggested that intratracheal administration of Formulation 25 showed a DDS effect specific to the lung disease site.

Further, intratracheal administration of Formulation 25 at 0.3 mg/kg once weekly showed the same survival rate (50%) as those of intravenous administration of Formulation 25 at 1 mg/kg or 3 mg/kg once weekly, suggesting that the intratracheal administration achieves a greater DDS effect, i.e., about 10 times that of the intravenous administration.

3) Analysis of Effect of Formulation 25 (ONO-1301Lipo) on Spontaneous Dilated Cardiomyopathy (J2N-k) Hamsters (1) Test System Improvement in the DDS cardiac function in the spontaneous dilated cardiomyopathy (J2N-k) hamster model by intermittent intravenous administration of Formulation 25 and compound (A) (ONO-1301) once every two weeks was evaluated by comparing the left ventricular ejection fraction (hereinafter referred to as "EF %"), left ventricular fractional shortening (hereinafter referred to as "% FS"), and histological evaluation, based on echocardiography, taken as indices. As a positive control, a group in which compound (A) (ONO-1301) was repeatedly orally administered twice daily was created.

As a test substance, Formulation 25 was used by suspending and diluting with physiological saline. Compound (A) (ONO-1301) as a control was used by dissolving in an equivalent amount of aqueous NaOH, and diluting with physiological saline. For groups of oral administration of compound (A) (ONO-1301), administration was performed as a suspension in a 0.5% CMC-Na aqueous solution.

The spontaneous dilated cardiomyopathy (J2N-k) male hamsters, 20 weeks old at the start of administration, Japan SLC, Inc., were administered with the test substances for 8 weeks, and used for comparison.

(2) Table 22 shows the group constitution.

TABLE 22

| Group | Route of administration | Number of animals |
|---|---|---|
| Group 1; Control (physiological saline) | Once/2 weeks Intravenous administration | 4 |
| Group 2; Formulation 25 *3 mg/kg (ONO-1301Lipo) | Once/2 weeks Intravenous administration | 5 |
| Group 3; Compound (A) (ONO-1301): 3 mg/kg | Once/2 weeks Intravenous administration | 4 |
| Group 4; Compound (A) (ONO-1301): 3 mg/kg | Twice/day Repeated oral administration | 5 |

*The dose is in terms of compound (A) (ONO-1301).

Liquid dose: 5 ml/kg (3) Echocardiography

Animals arrived at the age of 18 weeks were subjected to a 2-week quarantine/acclimation period, and then to the test at the time of grouping (test start date) at the age of 20 weeks. Thereafter, tests were conducted 4 and 8 weeks after the test start date, and dissection was performed 8 weeks after the test start date.

(4) Dissection and Treatment of Removed Tissue

The final echocardiography was performed 8 weeks after the start of administration. Thereafter, dissection was performed.

Dissection was performed as follows. After all of the blood was collected from the abdominal aorta, and the hamsters were euthanized under isoflurane anesthesia, the heart and lungs were removed and weighed. After the weights thereof were measured, the removed parts, including the left and right ventricles, were divided into three parts; i.e., apical, middle, and basal parts, at intervals of about 2 mm along the short axis.

For the three divided tissues, the short-axis sections including the right and left ventricles of the middle part were immersed in 4% paraformaldehyde (for general pathological examination), and stored.

(5) Measurement of Left Ventricular Wall Thickness and Area in Short-Axis Sections of Removed Heart When removed, the heart, including the left and right ventricles, was divided into three parts; i.e., apical, middle, and basal parts, at intervals of about 2 mm along the short axis. Among them, one section of the middle part was photographed, and the wall thickness at the anterior, lateral, posterior, and septum parts, and the left ventricular area were measured using image-editing software. For the wall thickness of the left ventricle, image-editing software was used, the number of pixels in the scale area of 1 $mm^2$ on the photograph was obtained, and the outer diameter and inner diameter of the entire left ventricle wall were traced to obtain each number of pixels to thus calculate the left ventricular area by ((the number of pixels of the outer diameter−the number of pixels of the inner diameter)/1 $mm^2$). Thereafter, the wall thickness of each portion was measured.

FIG. 31 shows the measurement method. The section was divided into three parts; i.e., apical, middle, and basal areas, at intervals of about 2 mm. Thereafter, using one section on the middle side, the wall thickness at the anterior, lateral, posterior, and septum parts, and the left ventricular area were measured. For the wall thickness of the left ventricle, image-editing software was used, the number of pixels in the scale area of 1 $mm^2$ on the photograph was obtained, and the outer diameter and inner diameter of the entire left ventricle wall were traced to obtain each number of pixels to thus calculate the left ventricular wall area by ((the number of pixels of the outer diameter−the number of pixels of the inner diameter)/1 $mm^2$). Thereafter, the wall thickness of each portion was measured.

(6) Test Results

Table 23 shows the measurement results of EF % values and % FS values determined by echocardiography.

TABLE 23

| Drugs | N | EF % | | | % FS | | |
|---|---|---|---|---|---|---|---|
| | | Pre | 4 W | 8 W | Pre | 4 W | 8 W |
| Group 1; Control | 4 | 42.5 ± 3.2 | 33.6 ± 12.3 | 31.5 ± 3.5[a] | 17.8 ± 1.4 | 13.3 ± 6.1 | 12.6 ± 1.6[a] |
| Group 4; Compound (A) (ONO-1301): 3.0 mg/kg, p.o. | 5 | 43.0 ± 7.8 | 40.4 ± 14.9 | 40.3 ± 9.2* | 18.2 ± 3.9 | 17.2 ± 7.2 | 17.1 ± 4.5* |
| Group 3; compound (A) (ONO-1301): 3.0 mg/kg, intravenous administration | 4 | 38.8 ± 4.3 | 35.7 ± 7.4 | 30.8 ± 2.9[a] | 16.0 ± 2.1 | 16.1 ± 3.1 | 12.3 ± 1.3[a] |

TABLE 23-continued

| Drugs | N | EF % Pre | 4 W | 8 W | % FS Pre | 4 W | 8 W |
|---|---|---|---|---|---|---|---|
| Group 2; formulation 25: 3.0 mg/kg i.v. | 5 | 40.5 ± 5.1 | 44.5 ± 9.9 | 39.6 ± 4.1* | 16.9 ± 2.6 | 18.5 ± 4.9 | 16.5 ± 2.1** |

Data shown: the mean ± standard deviation
*p < 0.05,
**p < 0.01 (significantly different from the control value by Student's t-test)
$^a$p < 0.01 (significantly different from the pre-value by Student's t-test)

Echocardiography was performed at the time of grouping, and at week 4 and week 8 after the start of administration. The measurement was performed 3 times for each individual, and the average value of the measured data was referred to as the measurement results.

In the control group (Group 1), the EF % values at the time of grouping, and at week 4 and week 8 were 42.5±3.2%, 33.6±12.3%, and 31.5±3.5%, respectively. The EF % value at week 8 showed a significant decrease (p<0.05) compared with the EF % value at the time of grouping. The % FS values at the time of grouping and at week 4 and week 8 were 17.8±1.4%, 13.3±6.1%, and 12.6±1.6%, respectively. Similar to the EF % value, the EF % value at week 8 showed a significant decrease (p<0.01) compared with the % FS value at the time of grouping.

The EF % values of the group of repeat oral administration of compound (A) (ONO-1301) at 3.0 mg/kg×twice/day (Group 4) at the time of grouping and at week 4 and week 8 were 43.0±7.8%, 40.4±14.9%, and 40.3±9.2%, respectively. Compared with the value at the time of grouping, the values at week 4 and week 8 showed no significant decrease in cardiac function. The EF % value at week 8 was higher than that of the control group, showing a significant difference (p<0.05). The % FS values at the time of grouping and at week 4 and week 8 were 18.2±3.9%, 17.2±7.2%, and 17.1±4.5%, respectively, which were similar to the EF % values.

The EF % values of the group of intravenous administration of compound (A) (ONO-1301) at 3.0 mg/kg (Group 3) at the time of grouping and at week 4 and week 8 were 38.8±4.3%, 35.7±7.4%, and 30.8±2.9%, respectively. The decrease at week 4 was slower than that of the control group; however, the decrease at week 8 was similar to that of the control group. The EF % value at week 8 showed a significant decrease (p<0.01) from the value at the time of grouping. The % FS values at the time of grouping and at week 4 and week 8 were 16.0±2.1%, 16.1±3.1%, and 12.3±1.3%, respectively. These results were similar to the EF % values, showing no efficacy.

In contrast, the EF % value of the group of intravenous administration of Formulation 25 (ONO-1301Lipo) at 3.0 mg/kg (Group 2) at the time of grouping and at week 4 and week 8 were 40.5±5.1%, 44.5±9.9%, and 39.6±4.1%, respectively. Although the difference was not significant, a slight increase was observed at week 4. At week 8, the decrease was suppressed in a manner similar to that of the group of oral administration of compound (A) (ONO-1301) at 3.0 mg/kg, and the value was significantly higher (p<0.05) compared with that of the control group. The % FS values at the time of grouping and at week 4 and week 8 were 16.9±2.6%, 18.5±4.9%, and 16.5±2.1%, respectively; thus, the change was similar to that of the EF % values. The value at week 8 showed a significant effect (p<0.01) compared with that of the control group (Group 1), and this effect was similar to that of the group of repeat oral administration of compound (A) (ONO-1301) (Group 4).

2. Measurement Results of the Wall Thickness of Removed Heart (Evaluation on the Short-Axis Section of the Middle Part)

Table 24 shows the wall thickness measurement results.

As shown in Table 24, the wall thicknesses of the apical, lateral, posterior, and septum of the middle section in the control group (Group 1) were 0.8±0.1 mm, 1.1±0.2 mm, 1.1±0.2 mm, and 1.0±0.2 mm, respectively.

In the group of oral administration of compound (A) (ONO-1301) at 3.0 mg/kg (Group 4), the wall thicknesses of the apical, lateral, posterior, and septum of the middle section were 1.4±0.5 mm, 1.5±0.2 mm, 1.2±0.4 mm, and 1.5±0.3 mm, respectively. Thus, the thicknesses of the apical, lateral, and septum were significantly higher (p<0.05) than those of the control group.

In the group of intravenous administration of compound (A) (ONO-1301) at 3.0 mg/kg (Group 3), these values were 1.1±0.6 mm, 1.2±0.3 mm, 1.2±0.2 mm, and 1.0±0.3 mm, respectively. These measurement results were similar to those of the control group.

In contrast, in the group of intravenous administration of Formulation 25 (ONO-1301Lipo) at 3.0 mg/kg (Group 2), these values were 1.7±0.4 mm**, 1.5±0.1 mm*, 1.5±0.6 mm$^†$, and 1.2±0.3 mm, respectively. These values were significantly higher and showed a tendency to achieve higher values in the apical (p<0.01), lateral (p<0.05), and posterior (0.05<p<0.1), compared with those of the control group.

TABLE 24

| Drugs | N | Body weight (g) Before drug administration | Body weight at dissection | Left ventricle wall thickness (mm) Anterior | Lateral | Posterior | Septum |
|---|---|---|---|---|---|---|---|
| Group 1: Control | 4 | 120.2 ± 7.3 | 129.4 ± 6.7 | 0.8 ± 0.1 | 1.1 ± 0.2 | 1.1 ± 0.2 | 1.0 ± 0.2 |
| Group 4: compound (A) (ONO-1301): 3.0 mg/kg, p.o. | 5 | 118.8 ± 9.6 | 128.6 ± 3.0 | 1.4 ± 0.5* | 1.5 ± 0.2* | 1.2 ± 0.4 | 1.5 ± 0.3* |

TABLE 24-continued

| Drugs | N | Body weight (g) | | Left ventricle wall thickness (mm) | | | |
|---|---|---|---|---|---|---|---|
| | | Before drug administration | Body weight at dissection | Anterior | Lateral | Posterior | Septum |
| Group 3: compound (A) (ONO-1301): 3.0 mg/kg, intravenous administration | 4 | 128.7 ± 10.4 | 144.4 ± 13.3 | 1.1 ± 0.6 | 1.2 ± 0.3 | 1.2 ± 0.2 | 1.0 + 0.3 |
| Group 2; Formulation 25: 3.0 mg/kg, intravenous administration | 5 | 119.6 ± 10.5 | 138.8 ± 12.4 | 1.7 ± 0.4** | 1.5 ± 0.1* | 1.5 ± 0.6$^\dagger$ | 1.2 ± 0.3 |

Data shown: the mean ± standard deviation
$^\dagger 0.05 < p < 0.1$,
$*p < 0.05$,
$**p < 0.01$ (significantly different from the control value by Student's t-test)

3. Measurement Results of the Left Ventricular Wall Area of Removed Heart (Evaluation on the Short-Axis Section of the Middle Part)

Table 25 shows the left ventricular area measurement results.

As shown in Table 25, the measurement results of the left ventricular wall area of the control group (Group 1), the group of oral administration of compound (A) (ONO-1301) at 3.0 mg/kg (Group 4), the group of intravenous administration of compound (A) (ONO-1301) at 3.0 mg/kg (Group 3), and the group of intravenous administration of Formulation 25 (ONO-1301Lipo) at 3.0 mg/kg (Group 2) were $23.4 \pm 5.4$ mm$^2$, $26.4 \pm 4.3$ mm$^2$, $23.9 \pm 4.5$ mm$^2$, and $29.5 \pm 6.4$ mm$^2$, respectively. These measurement results showed no significant difference; however, reflecting the wall thickness measurement results, there was a tendency that the control group (Group 1) and the group of intravenous administration of compound (A) (ONO-1301) at 3.0 mg/kg (Group 3) showed lower values, while the group of oral administration of compound (A) (ONO-1301) at 3.0 mg/kg (Group 4) and the group of intravenous administration of Formulation 25 (ONO-1301Lipo) at 3.0 mg/kg (Group 4) showed higher values.

TABLE 25

| Drugs | N | Left ventricular area (Middle part) (mm$^2$) |
|---|---|---|
| Group 1: Control | 4 | 23.4 ± 5.4 |
| Group 4: Compound (A) (ONO-1301): 3.0 mg/kg, p.o. | 5 | 26.4 ± 4.3 |
| Group 3: Compound (A) (ONO-1301): 3.0 mg/kg, i.v. | 4 | 23.9 ± 4.5 |
| Group 2; Formulation 25; 3.0 mg/kg, i.v. | 5 | 29.5 ± 6.4$^\dagger$ |

Data shown: the mean ± standard deviation
$0.05 < p < 0.1$ (significantly different from the control value by Student's t-test)

As described above, the cardiac function improvement effect of Formulation 25 (ONO-1301Lipo) was analyzed using spontaneous dilated cardiomyopathy (J2N-k) hamsters. The test was initiated after the onset of the pathological condition, and at the age of 20 weeks when the cardiac function considerably decreased. The test substance was administered until week 28, and the change in the cardiac function was analyzed.

In the cardiac function evaluation using EF % and % FS values determined by echocardiography as indices, the group in which compound (A) (ONO-1301) was repeatedly orally administered at 3.0 mg/kg×twice/day (Group 4) and the group in which Formulation 25 (ONO-1301Lipo) was intermittently administered intravenously at 3.0 mg/kg 4 times in total (at the time of grouping; and at week 2, week 4, and week 6) (Group 2) showed an effect in terms of suppressing a decrease in the cardiac function, compared with the control group (Group 1) and the group of intravenous administration of compound (A) (ONO-1301) at 3.0 mg/kg (Group 3). In the measurement results of the left ventricle wall thickness, the control group (Group 1) and the group of intravenous administration of compound (A) (ONO-1301) at 3.0 mg/kg (Group 3) showed low values, which suggested the progress of thinning. In contrast, the group of repeat oral administration of compound (A) (ONO-1301) at 3.0 mg/kg (Group 4) and the group of Formulation 25 (ONO-1301Lipo) at 3.0 mg/kg (Group 2) showed higher values, suggesting the suppression of the progress of thinning, compared with the control group (Group 1) and the group of intravenous administration of compound (A) (ONO-1301) at 3.0 mg/kg (Group 3). This is assumed to reflect the results of EF % and % FS values determined by echocardiography.

The above results suggested that the group of repeat oral administration of compound (A) (ONO-1301) at 3.0 mg/kg× twice/day (Group 4) and the group of intermittent intravenous administration of Formulation 25 (ONO-1301LipoNS) at 3.0 mg/kg once every 2 weeks (Group 2) suppressed a decrease in the cardiac function in the spontaneous dilated cardiomyopathy (J2N-k) hamsters.

The total dose amount of the repeat oral administration of compound (A) (ONO-1301) at 3 mg/kg×twice×56 days was 336 mg/kg, while the total dose amount of the intravenous administration of Formulations 25 (ONO-1301Lipo) at 3 mg/kg×4 times was 12 mg/kg; both of these showed a similar efficacy. The intermittent intravenous administration of compound (A) (ONO-1301) at 3 mg/kg once every 2 weeks showed no effect. Accordingly, the intermittent intravenous administration of Formulation 25 (ONO-1301Lipo) once every 2 weeks showed the effect at a dose of ⅛ of that of the repeat oral administration of compound (A) (ONO-1301). This confirmed the DDS effect of intravenous administration of Formulation 25 (ONO-1301Lipo).

Tables 26 and 27 show the body weight change at the time of grouping and at the time of dissection, and the weights of heart and lung at the time of dissection. No change was observed in any of these.

TABLE 26

| | | Body weight (g) | |
| Drugs | N | Before drug administration | Body weight at dissection |
| --- | --- | --- | --- |
| Control | 4 | 120.2 ± 7.3 | 129.4 ± 6.7 |
| compound (A) (ONO-1301): 3.0 mg/kg, p.o. | 5 | 118.8 ± 9.6 | 128.6 ± 3.0 |
| Compound (A) (ONO-1301): 3.0 mg/kg, i.v. | 4 | 128.7 ± 10.4 | 144.4 ± 13.3 |
| Formulation 25: 3.0 mg/kg, i.v. | 5 | 119.6 ± 10.5 | 138.8 ± 12.4 |

Data shown: the mean ± standard deviation

TABLE 27

| Drugs | N | Body weight (g) Body weight at dissection | Real tissue weight (g) Heart | Lung | Tissue weight per 100 g of the body weight (g) Heart | Lung |
| --- | --- | --- | --- | --- | --- | --- |
| Control | 4 | 129.4 ± 6.7 | 0.4674 ± 0.0666 | 0.5640 ± 0.0949 | 0.3602 ± 0.0340 | 0.4346 ± 0.0548 |
| Compound (A) (ONO-1301): 3.0 mg/kg, p.o. | 5 | 128.6 ± 3.0 | 0.4379 ± 0.0136 | 0.5202 ± 0.0336 | 0.3404 ± 0.0032 | 0.4043 ± 0.0203 |
| Compound (A) (ONO-1301): 3.0 mg/kg, i.v. | 4 | 144.4 ± 13.3 | 0.5028 ± 0.0631 | 0.5740 ± 0.0527 | 0.3475 ± 0.0165 | 0.3998 ± 0.0470 |
| Formulation 25: 3.0 mg/kg, i.v. | 5 | 138.8 ± 12.4 | 0.4797 ± 0.0673 | 0.5645 ± 0.0625 | 0.3446 ± 0.0222 | 0.4068 ± 0.0276 |

Data shown: the mean ± standard deviation

4) Analysis of Effect of Single Intravenous Administration of Formulation 25 (ONO-1301LipoNS) on Rat Model of Ischemia by Complete Coronary Artery Ligation An improvement in the cardiac function against ischemic heart disease and an effect of preventing death from heart failure by intermittent intravenous administration of Formulation 25 (ONO-1301Lipo) or compound (A) (ONO-1301) were analyzed by using the left ventricular ejection fraction (hereinafter referred to as "EF %"), left ventricular fractional shortening (hereinafter referred to as "% FS"), and histological evaluation, based on echocardiography, as indices.

(1) Preparation of Myocardial Ischemia Model

Male Sprague-Dawley rats (CLEA Japan, Inc., 6 weeks old when arrived) were anesthetized with a liquid mixture of 0.5 mg/kg of midazolam (Dormicum Injection 10 mg, Astellas Pharma Inc.) and 2 mg/kg of xylazine (Celactal 2% injection, Bayer Japan Ltd.). Thereafter, the animal tail veins were secured, and Propofol (1% Diprivan Injection; AstraZeneca K.K.) was continuously infused at 6 to 10 mg/kg/hr with a syringe pump (Terufusion TE-3310N; Terumo Corporation) to maintain deep anesthesia. Thereafter, a tracheal cannula (a cut-down catheter with an outside diameter of 2.0 mm, produced by JMS Co., Ltd.) was inserted and indwelled, and a respirator (for small animals; Shinano Seisakusho) was connected to maintain breathing at a stroke volume of 1 mL/100 g/stroke (±1 mL) and a stroke rate of 70 times/min (±10 times). Thereafter, the animals were fixed in a recumbent position from a dorsal fixed position so that the left chest faced upward, and the epidermis and muscle layer between the third to fourth or fourth to fifth ribs were incised with a surgical knife. After confirming that the knife reached the thoracic cavity, the intercostal space was widened with a rib spreader, and a state in which the anterior descending branch (hereinafter referred to as "LAD") from the left atrial appendage was directly visible at the front was secured.

Thereafter, the translucent thin pericardium was removed with tweezers to expose the myocardium. Thereafter, the LAD located at the margin of the left atrial appendage was pierced and secured with a nylon thread with a 6-0 or 7-0 needle at a depth of 2 to 3 mm using a microneedle holder, and the LAD was completely ligated. Thereafter, the muscle layer and epidermis were sutured and closed with a 4-0 or 5-0 nylon thread. After the chest was closed, 50 mg of cefamedin was subcutaneously administered to the treatment site, and the treatment was terminated.

(2) Table 28 shows the group constitution.

TABLE 28

| Group | Route of administration | Number of animals |
| --- | --- | --- |
| Group 1: Normal | — | 3 |
| Group 2: Control (Physiological saline) | Intravenous administration | 5 |
| Group 3: Formulation 25 (ONO-1301Lipo): 0.3 mg/kg | Intravenous administration | 5 |
| Group 4: Formulation 25 (ONO-1301Lipo): 1.0 mg/kg | Intravenous administration | 5 |
| Group 5: Formulation 25 (ONO-1301Lipo): 3.0 mg/kg | Intravenous administration | 5 |
| Group 6: Compound (A) (ONO-1301): 3.0 mg/kg | Intravenous administration | 5 |

1) Liquid dose: 5 mL/kg
2) Single intravenous administration to the tail 24 hours after infarction (3) Echocardiography Echocardiography was performed to confirm the cardiac function improving effect of the test substances using the left ventricular ejection fraction (hereinafter referred to as "EF %") as an index.

The test was performed 23 hours after the preparation of the model (test for grouping), the animals whose EF % value decreased by 25% or more of that of normal animals were selected, grouping was performed, and a solution for administration of the test substances was administered by tail vein intravenous administration 24 hours after the preparation of the model. Thereafter, echocardiography was performed 7 and 14 days after the test substance administration.

(4) Dissection and Treatment of Removed Tissue

Dissection was performed after the completion of the echocardiography at day 14 after the administration of the test substance. For dissection, all of the blood was collected from the abdominal aorta, and the rats were euthanized under isoflurane anesthesia; thereafter, the heart was removed and weighed. After measuring the heart weight, the infarct area, including the left and right ventricles, was divided into three parts along the short axis.

(5) Test Results (1) Measurement Results of EF % Value Determined by Echocardiography Tables 29 and 30 show the echocardiography results.

As shown in Table 29, the EF % value in the normal animals was 85.0±1.9% (n=4). The EF % value of each group 23 hours after the complete LAD ligation and before the test substance administration was such that the control group was 52.8±6.8% (n=5), and the groups of administration of Formulation 25 (ONO-1301Lipo) at 0.3 mg/kg, 1.0 mg/kg, and 3.0 mg/kg were 55.1±2.4% (n=5), 55.0±4.1% (n=5), and 54.7±5.2% (n=5), respectively. The group of administration of compound (A) (ONO-1301) at 3 mg/kg was 56.7±5.5% (n=5).

The EF % values of all of the groups before the test substance administration showed a significant decrease (p<0.01) compared with the EF % value of the normal animals; no significant difference was observed among the groups.

As shown in Table 29, the change in the EF % value of each group at day 7 and day 14 after the administration were as follows. In the control group, the EF % value was 52.8±6.8% (n=5) before the administration; and decreased in a time-dependent manner to 48.9±4.0% and 39.0±5.2%, respectively. The EF % value 2 weeks later showed a significant decrease (p<0.05) compared with that before the administration.

In the 0.3 mg/kg administration group of Formulation 25 (ONO-1301LipoNS), the EF % value was 55.1±2.4% (n=5) before the administration; and the values at day 7 and day 14 were 50.7±6.2% and 42.0±6.2%, respectively, showing similar changes to those of the control group. Similar to the control group, the EF % value of this group at day 14 also showed a significant decrease (p<0.05) compared with that before the administration.

In the 1.0 mg/kg administration group, the EF % value was 55.0±4.1% (n=5) before the administration; and the values at day 7 and day 14 were 53.6±7.5% and 54.7±8.2%, respectively; which were similar to the EF % value before the administration. The EF % value at day 14 showed a significant increase (p<0.05) compared with that of the control group.

In the 3.0 mg/kg administration group, the EF % value was 54.7±5.2% (n=5) before the administration, and increased to 62.4±8.7% and 58.2±13.2%, respectively. The increase in the EF % value showed a peak on day 7 after the administration compared with the EF % value before the administration, indicating an improvement in the cardiac function. The EF % values at day 7 and day 14 after the test substance administration showed a significant suppression of a decrease (p<0.05 and p<0.01, respectively) compared with those of the control group.

In the group of administration of compound (A) (ONO-1301) at 3.0 mg/kg, the EF % value of was 56.7±5.5% (n=5) before the administration, and changed to 54.6±8.8% and 53.2±7.1%, respectively, showing a tendency of a decrease from the EF % value before the administration, although the difference was not significant. However, a comparison with those of the control group at day 7 and day 14 revealed no significant difference in both day 7 and day 14.

4. Measurement Results of % FS Value Determined by Echocardiography

As shown in Table 29, the % FS value in the normal animals was 49.4±2.4% (n=4). The % FS value of each group 23 hours after the complete LAD ligation and before the test substance administration was such that the control group was 23.9±3.7% (n=5); and the groups of administration of Formulation 25 (ONO-1301Lipo) at 0.3 mg/kg, 1.0 mg/kg, and 3.0 mg/kg were 25.0±1.7% (n=5), 25.8±2.4% (n=5), and 25.0±3.0% (n=5), respectively. The % FS value of the group of administration of compound (A) (ONO-1301) at 3 mg/kg was 26.5±3.7% (n=5). Usually, the normal % FS value is clinically said to be 28% or more. Although the difference was slight, the % FS values of all of the groups were lower than this value.

The % FS values of all of the groups before the test substance administration showed a significant decrease (p<0.01) compared with the EF % value of the normal animals; no significant difference was observed among the groups.

As shown in Table 30, the change in the % FS value of each group at day 7 and day 14 after the administration were as follows. In the control group, the % FS value was 23.9±3.7% before the administration (n=5); and decreased in a time-dependent manner to 21.8±2.2% and 16.7±2.7%, respectively. Similar to the EF % value, the % FS value 2 weeks later showed a significant decrease (p<0.05) compared with that before the administration.

In the 0.3 mg/kg administration group of Formulation 25 (ONO-1301Lipo), the % FS value was 25.0±1.7% (n=5) before the administration; and the values at day 7 and day 14 were 22.9±3.4% and 18.4±3.2%, respectively, showing similar changes to those of the control group. Similar to the control group, the % FS value at day 14 also showed a significant decrease (p<0.05) compared with that before the administration.

In the 1.0 mg/kg administration group, the % FS value was 25.8±2.4% (n=5) before the administration; and the values at day 7 and day 14 were 24.8±4.2% and 25.4±5.0%, respectively, which were similar to the FS % value before the administration.

In the 3.0 mg/kg administration group, the % FS value was 25.0±3.0% (n=5) before the administration, and increased to 30.1±5.4% and 27.9±8.5%, respectively. The increase in the % FS value showed a peak on day 7 after the administration compared with the % FS value before the administration. The % FS values at day 7 and day 14 after the test substance administration both showed a significant increase (p<0.05) compared with those of the control group.

In the group of administration of compound (A) (ONO-1301) at 3.0 mg/kg, the % FS value was 26.5±3.7% (n=5) before the administration, and changed to 25.4±5.6% and 24.5±4.4%, respectively, showing a tendency of a decrease from the % FS value before the administration, although the difference was not significant. However, a comparison with those of the control group at day 7 and day 14 revealed no significant difference in both day 7 and day 14.

As described above, the measurement results showed correlation between the EF % and % FS values, which are used as indices of the evaluation of the cardiac function, in each group; and the single intravenous administration of Formulation 25 (ONO-1301LipoNS) at 1.0 mg/kg or 3.0 mg/kg showed a cardiac function improving effect.

TABLE 29

| Drugs | N | EF % | % FS |
|---|---|---|---|
| Group 1: Normal | 4 | 85.0 ± 1.9 | 49.4 ± 2.4 |
| Group 2: Control | 5 | 52.8 ± 6.8** | 23.9 ± 3.7** |
| Group 3: Formulation 25: 0.3 mg/kg | 5 | 55.1 ± 2.4** | 25.0 ± 1.7** |
| Group 4: Formulation 25: 1.0 mg/kg | 5 | 55.0 ± 4.1** | 25.8 ± 2.4** |
| Group 5: Formulation 25: 3.0 mg/kg | 5 | 54.7 ± 5.2** | 25.0 ± 3.0** |
| Group 6: Compound (A) (ONO-1301): 3.0 mg/kg | 5 | 56.7 ± 5.5** | 26.5 ± 3.7** |

Data shown: the mean ± standard deviation

**$p < 0.01$ (significantly different from the normal value by Dunnett's test)

TABLE 30

| Drugs | N | EF % | | | % FS | | |
|---|---|---|---|---|---|---|---|
| | | Pre | 1 W | 2 W | Pre | 1 W | 2 W |
| Group 2: Control | 5 | 52.8 ± 6.8 | 48.9 ± 4.0 | 39.0 ± 5.2$^a$ | 23.9 ± 3.7 | 21.8 ± 2.2 | 16.7 ± 2.7$^a$ |
| Group 3: Formulation 25: 0.3 mg/kg | 5 | 55.1 ± 2.4 | 50.7 ± 6.2 | 42.0 ± 6.2$^a$ | 25.0 ± 1.7 | 22.9 ± 3.4 | 18.4 ± 3.2$^a$ |
| Group 4: Formulation 25: 1.0 mg/kg | 5 | 55.0 ± 4.1 | 53.6 ± 7.5 | 54.7 ± 8.2* | 25.8 ± 2.4 | 24.8 ± 4.2 | 25.4 ± 5.0 |
| Group 5: Formulation 25: 3.0 mg/kg | 5 | 54.7 ± 5.2 | 62.4 ± 8.7* | 58.2 ± 13.2** | 25.0 ± 3.0 | 30.1 ± 5.4* | 27.9 ± 8.5* |
| Group 6: Compound (A) (ONO-1301): 3.0 mg/kg | 5 | 56.7 ± 5.5 | 54.6 ± 8.8 | 53.2 ± 7.1 | 26.5 ± 3.7 | 25.4 ± 5.6 | 24.5 ± 4.4 |

Data shown: the mean ± standard deviation

*$p < 0.05$,

**$p < 0.01$ (significantly different from the control value by Dunnett's test)

$^a$$p < 0.05$ (significantly different from the pre-value by t-test)

TABLE 31

| Drugs | N | Body weight (g) | | | | |
|---|---|---|---|---|---|---|
| | | Before preparation of AMI | Before drug administration | At dissection | Total weight of isolated heart (g) | Heart weight per 100 g of body weight (g) |
| Group 2: Control | 5 | 334.3 ± 19.3 | 315.2 ± 15.2 | 407.6 ± 14.8 | 1.3997 ± 0.0876 | 0.3431 ± 0.0219 |
| Group 3: Formulation 25: 0.3 mg/kg | 5 | 331.2 ± 19.7 | 317.7 ± 16.2 | 408.2 ± 23.2 | 1.3191 ± 0.1493 | 0.3236 ± 0.0362 |
| Group 4: Formulation 25: 1.0 mg/kg | 5 | 340.2 ± 18.7 | 320.8 ± 21.5 | 412.4 ± 13.4 | 1.3179 ± 0.0655 | 0.3199 ± 0.0206 |
| Group 5: Formulation 25: 3.0 mg/kg | 5 | 329.2 ± 16.1 | 315.3 ± 14.2 | 409.8 ± 9.1 | 1.3426 ± 0.1025 | 0.3277 ± 0.0255 |
| Group 6: compound (A) (ONO-1301): 3.0 mg/kg | 5 | 339.7 ± 13.6 | 325.1 ± 22.3 | 406.7 ± 37.4 | 1.3312 ± 0.1827 | 0.3267 ± 0.0235 |

Infarct Area Evaluation Method

For the sections, the apical portion was removed, and the middle area was sectioned into two parts at an interval of about 2 mm. Thereafter, the infarct area of the two sections on the apical and basal sides was measured. The infarct area was evaluated based on the ratio of the infarct area to the entire left ventricular area, and the ratio of the length of the normal area or the infarct area to the left ventricular outer diameter.

FIG. 32 shows an infarct area evaluation method. For the sections, the apical portion was removed, and the middle area was sectioned into two parts at an interval of about 2 mm. Thereafter, the infarct area of the two sections on the apical and basal sides was measured. The infarct area was evaluated based on the ratio of the infarct area to the entire left ventricular area, and the ratios of the length of the normal area or the infarct area to the left ventricular outer diameter.

The results revealed that the group of administration of Formulation 25 at 3 mg/kg showed a significant decrease in the ratio of the infarct area relative to the entire left ventricle area, and the ratio of the infarct area in the left ventricular outer diameter area (Table 32 and Table 33).

The results confirmed that Formulation 25 reduced the infarct area, indicating that an effect was exhibited. In contrast, the administration of compound (A) (ONO-1301) at 3 mg/kg showed no effect. These results suggested that Formulation 25 exhibited a DDS effect.

TABLE 32

| Drugs | N | Left ventricular area (mm$^2$) | | | Left ventricular area (mm$^2$) | | |
|---|---|---|---|---|---|---|---|
| | | Normal region | Infarct region | Infarct rate (%) | Normal region | Infarct region | Infarct rate (%) |
| Group 2: Control | 5 | 35.7 ± 6.13 | 17.8 ± 3.22 | 34 ± 7.3 | 41.1 ± 6.80 | 13.3 ± 2.45 | 25 ± 5.2 |
| Group 3: Formulation 25: 0.3 mg/kg | 5 | 36.7 ± 1.43 | 23.4 ± 8.54 | 38 ± 8.7 | 41.8 ± 10.70 | 18.9 ± 4.56 | 31 ± 5.7 |
| Group 4: Formulation 25: 1.0 mg/kg | 5 | 34.6 ± 7.73 | 15.9 ± 2.12 | 32 ± 6.4 | 42.0 ± 9.04 | 17.6 ± 2.65 | 30 ± 6.4 |
| Group 5: Formulation 25: 3.0 mg/kg | 5 | 41.0 ± 4.88 | 6.5 ± 4.83 | 13 ± 9.8** | 49.7 ± 7.72 | 8.1 ± 3.72 | 14 ± 6.4* |
| Group 6: Compound A: 3.0 mg/kg | 5 | 31.1 ± 2.83 | 18.1 ± 5.18 | 36 ± 8.0 | 41.0 ± 8.03 | 14.6 ± 3.23 | 26 ± 2.2 |

Data shown in the table: the mean ± standard deviation
*$p < 0.05$;
**$p < 0.01$ (Dunnett's test)

TABLE 33

| Drugs | N | Left ventricular outer diameter (cm) | | | Left ventricular outer diameter (cm) | | |
|---|---|---|---|---|---|---|---|
| | | Normal region | Infarct region | Infarct rate (%) | Normal region | Infarct region | Infarct rate (%) |
| Group 2: Control | 5 | 1.9 ± 0.36 | 1.4 ± 0.18 | 42 ± 4.9 | 2.5 ± 0.23 | 1.2 ± 0.20 | 32 ± 5.2 |
| Group 3: Formulation 25: 0.3 mg/kg | 5 | 1.6 ± 0.34 | 1.5 ± 0.53 | 47 ± 14.9 | 2.3 ± 0.06 | 1.3 ± 0.19 | 36 ± 3.3 |
| Group 4: Formulation 25: 1.0 mg/kg | 5 | 1.9 ± 0.53 | 1.1 ± 0.24 | 37 ± 12.2 | 2.3 ± 0.39 | 1.2 ± 0.31 | 34 ± 9.5 |
| Group 5: Formulation 25: 3.0 mg/kg | 5 | 2.4 ± 0.16 | 0.6 ± 0.28 | 20 ± 7.7** | 2.7 ± 0.16 | 0.7 ± 0.21 | 19 ± 5.3* |
| Group 6: Compound A: 3.0 mg/kg | 5 | 1.7 ± 0.41 | 1.5 ± 0.15 | 46 ± 7.5 | 2.3 ± 0.41 | 1.2 ± 0.37 | 34 ± 10.2 |

Data shown in the table: the mean ± standard deviation
*$p < 0.05$;
**$p < 0.01$ (Dunnett's test)

The single intravenous administration of Formulation 25 (ONO-1301Lipo) suppressed the onset of the pathological condition in the rat heart ischemia model in a dose-correlated manner. Further, the administration of Formulation 25 at 3 mg/kg showed an improving effect over the Pre. Although the single intravenous administration of the compound (A) (ONO-1301) drug substance at 3 mg/kg showed a suppression effect similar to that of Formulation 25 at 1 mg/kg, no effect was observed in terms of reducing the infarct area.

These results confirmed that Formulation 25 exhibited a DDS effect.

What is claimed is:

1. A method for treating an ischemic organ disorder comprising administering a pharmaceutical composition into a subject, wherein the pharmaceutical composition comprises a stealth liposome having a prostaglandin I2 receptor agonist encapsulated therein, wherein the stealth liposome has an average particle size of 50 to 200 nm, and comprises 5 to 50 parts by weight of a phospholipid and 0.05 to 5 parts by weight of PEG-modified phosphoethanolamine, per part by weight of the prostaglandin I2 receptor agonist.

2. The method according to claim 1, wherein the prostaglandin I2 receptor agonist includes at least a compound represented by formula (I):

wherein is

-continued (ii)

$$CH{=}CH{-}(CH_2)_q{-}$$
$$(CH_2)_e$$

, (iii)

$$(CH_2)_p{-}$$
a
b
$$(CH_2)_f$$

or (iv)

$$CH{-}(CH_2)_r{-}$$
a
b
$$(CH_2)_f$$

in which e represents an integer of 3 to 5, f represents an integer of 1 to 3, p represents an integer of 1 to 4, q represents 1 or 2, and r represents an integer of 1 to 3;

$R^1$ represents a hydrogen atom or a $C_{1-4}$ alkyl group;

$R^2$ represents (i) a hydrogen atom, (ii) a $C_{1-8}$ alkyl group, (iii) a phenyl group or a $C_{4-7}$ cycloalkyl group, (iv) a 4- to 7-membered monocyclic ring containing one nitrogen atom, (v) a $C_{1-4}$ alkyl group substituted with a benzene ring or a $C_{4-7}$ cycloalkyl group, or (vi) a $C_{1-4}$ alkyl group substituted with a 4- to 7-membered monocyclic ring containing one nitrogen atom; and $R^3$ represents (i) a $C_{1-8}$ alkyl group, (ii) a phenyl group or a $C_{4-7}$ cycloalkyl group, (iii) a 4- to 7-membered monocyclic ring containing one nitrogen atom, (iv) a $C_{1-4}$ alkyl group substituted with a benzene ring or a $C_{4-7}$ cycloalkyl group, or (v) a $C_{1-4}$ alkyl group substituted with a 4- to 7-membered monocyclic ring containing one nitrogen atom; provided that when

B
D is a group represented by (iii) or (iv), $-(C-(CH_2)_p-$ and $=CH-(CH_2)_s-$ are bound to position a or b on the ring, and cyclic structures in $R^2$ and $R^3$ are optionally substituted with one to three $C_{1-4}$ alkyl groups, $C_{1-4}$ alkoxy groups, halogen atoms, nitro groups, or trihalomethyl groups; or a salt thereof.

3. The method according to claim 1, wherein the prostaglandin I2 receptor agonist includes at least the following compound (A):

(A) ({5-[2-({[(1E)-phenyl(pyridin-3-yl)methylene] amino}oxy)ethyl]-7,8-dihydronaphthalen-1-yl}oxy) acetic acid (ONO-1301) represented by formula (II):

(II)

or a salt of compound (A).

4. The method according to claim 1, wherein the prostaglandin I2 receptor agonist includes at least one of the following compounds (B) to (E):

(B) sodium (±)-(1R,2R,3aS,8bS)-2,3,3a,8b-tetrahydro-2-hydroxy-1-[(E)-(3S,4RS)-3-hydroxy-4-methyl-1-octen-6-ynyl]-1H-cyclopenta[b]benzofuran-5-butanoate (beraprost), or a derivative thereof that is a carbacyclic PGI2 derivative, (C) [4-[(5,6-diphenylpyrazinyl) (1-methylethyl)amino] butoxy]-acetic acid (MRE-269), (D) (2E)-7-{(1R,2R,3R)-3-hydroxy-2-[(1E,3S,5S)-3-hydroxy-5-methylnon-1-en-1-yl]-5-oxycyclopentyl}hept-2-enoic acid (limaprost), ornoprostil, enprostil, or misoprostol; or a derivative of any of these compounds that is a PEF derivative, and (E) 2-{4-[(5,6-diphenylpyrazin-2-yl) (propan-2-yl) amino]butoxy}-N-(methanesulfonyl) acetamide (NS-304; selexipag);

or a salt of any of compounds (B) to (E).

5. The method according to claim 1, wherein the prostaglandin I2 receptor agonist includes at least one member selected from the group consisting of ONO-1301, beraprost, limaprost, and NS-304.

6. The method according to claim 1, wherein the stealth liposome is obtainable by using at least a prostaglandin I2 receptor agonist and a phospholipid by the Bangham method, hydration dispersion method, reverse phase evaporation method, ethanol injection method, ethanol dilution method, homogenization method, mechanochemical method, direct dispersion method, extruder method, French press method, remote loading method, dehydration-rehydration method, freeze-thaw method, ultrasonic method, or lipid-compound film method; or an improved method of any of these methods.

7. The method according to claim 1,
wherein the stealth liposome comprises 0.05 to 5 parts by weight of MPEG2000-DSPE per part by weight of the prostaglandin I2 receptor agonist;
the prostaglandin I2 receptor agonist includes at least one member selected from the group consisting of ONO-1301, beraprost, limaprost, and NS-304; and
the stealth liposome releases the prostaglandin I2 receptor agonist over a period of 3 hours to 4 weeks.

8. The method according to claim 1, wherein the stealth liposome comprises
a prostaglandin I2 receptor agonist,
a phospholipid,
a PEG-modified phosphoethanolamine, and
a water-miscible organic solvent, and
does not comprise a sterol;

the liposome is obtainable by a production method comprising the following steps (1) to (8):

(1) mixing the prostaglandin I2 receptor agonist, the phospholipid, and the PEG-modified phosphoethanolamine in the solvent in amounts such that at least 5 mg of the phospholipid and at least 0.05 mg of the PEG-modified phosphoethanolamine are present per mg of the prostaglandin I2 receptor agonist, (2) heating the mixture obtained in step (1) to prepare a melt, (3) instantly freezing the melt obtained in step (2), (4) freeze-drying the frozen product obtained in step (3) to remove the solvent, (5) heating the freeze-dried product obtained in step (4) to disperse the heated product in an aqueous phosphate buffer solution, (6) sizing the dispersion obtained in step (5) with an extruder, (7) ultrafiltrating the dispersion obtained in step (6) to remove unencapsulated material, and (8) adding a sugar to the dispersion obtained in step (7) and freeze-drying the dispersion; and the liposome contains at least 0.001 mg of the prostaglandin I2 receptor agonist per 1.0 mg of the phospholipid, and has an average particle size of 50 to 200 nm.

9. The method according to claim 1, wherein the composition is for intravenous administration, intracoronary administration, inhalation, intramuscular administration, subcutaneous administration, oral administration, transmucosal administration, transdermal administration, or an internal organ, and is in the form of an injectable formulation, an oral preparation, an inhalant, a nebulizer, an ointment, a patch, or a spray.

10. The method according to claim 1, wherein a single intravenous dose of the composition is 0.001 to 100 mg in terms of the prostaglandin I2 receptor agonist.

11. The method according to claim 2, wherein the stealth liposome is obtainable by using at least a prostaglandin I2 receptor agonist and a phospholipid by the Bangham method, hydration dispersion method, reverse phase evaporation method, ethanol injection method, ethanol dilution method, homogenization method, mechanochemical method, direct dispersion method, extruder method, French press method, remote loading method, dehydration-rehydration method, freeze-thaw method, ultrasonic method, or lipid-compound film method; or an improved method of any of these methods.

12. The method according to claim 3, wherein the stealth liposome is obtainable by using at least a prostaglandin I2 receptor agonist and a phospholipid by the Bangham method, hydration dispersion method, reverse phase evaporation method, ethanol injection method, ethanol dilution method, homogenization method, mechanochemical method, direct dispersion method, extruder method, French press method, remote loading method, dehydration-rehydration method, freeze-thaw method, ultrasonic method, or lipid-compound film method; or an improved method of any of these methods.

13. The method according to claim 4, wherein the stealth liposome is obtainable by using at least a prostaglandin I2 receptor agonist and a phospholipid by the Bangham method, hydration dispersion method, reverse phase evaporation method, ethanol injection method, ethanol dilution method, homogenization method, mechanochemical method, direct dispersion method, extruder method, French press method, remote loading method, dehydration-rehydration method, freeze-thaw method, ultrasonic method, or lipid-compound film method; or an improved method of any of these methods.

14. The method according to claim 5, wherein the stealth liposome is obtainable by using at least a prostaglandin I2 receptor agonist and a phospholipid by the Bangham method, hydration dispersion method, reverse phase evaporation method, ethanol injection method, ethanol dilution method, homogenization method, mechanochemical method, direct dispersion method, extruder method, French press method, remote loading method, dehydration-rehydration method, freeze-thaw method, ultrasonic method, or lipid-compound film method; or an improved method of any of these methods.

* * * * *